(12) United States Patent
Gorenstein et al.

(10) Patent No.: US 9,567,579 B2
(45) Date of Patent: *Feb. 14, 2017

(54) STRUCTURE BASED AND COMBINATORIALLY SELECTED OLIGONUCLEOSIDE PHOSPHOROTHIOATE AND PHOSPHORODITHIOATE APTAMER TARGETING AP-1 TRANSCRIPTION FACTORS

(75) Inventors: David G. Gorenstein, Houston, TX (US); Bruce A. Luxon, Galveston, TX (US); James Leary, Galveston, TX (US); Xianbin Yang, Webster, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 257 days.

This patent is subject to a terminal disclaimer.

(21) Appl. No.: 13/014,597

(22) Filed: Jan. 26, 2011

(65) Prior Publication Data
US 2011/0212843 A1 Sep. 1, 2011

Related U.S. Application Data

(62) Division of application No. 10/851,864, filed on May 20, 2004, now Pat. No. 7,910,523.

(60) Provisional application No. 60/472,890, filed on May 23, 2003.

(51) Int. Cl.
*G01N 33/68* (2006.01)
*C12N 15/10* (2006.01)

(52) U.S. Cl.
CPC ....... *C12N 15/1048* (2013.01); *C12N 15/1034* (2013.01); *G01N 33/6818* (2013.01); *G01N 33/6848* (2013.01); *G01N 33/6851* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,949,064 A | 4/1976 | Bornstein et al. |
| 4,174,384 A | 11/1979 | Ullman et al. |
| 4,578,770 A | 3/1986 | Mitani |
| 4,596,792 A | 6/1986 | Vyas |

(Continued)

FOREIGN PATENT DOCUMENTS

| | | |
|---|---|---|
| EP | 0 568 925 A2 | 11/1993 |
| EP | 0 855 184 A1 | 7/1998 |

(Continued)

OTHER PUBLICATIONS

Maskos et al (1992 Nucleic Acids Research 20:1679-84).*

(Continued)

*Primary Examiner* — Christopher M Gross
(74) *Attorney, Agent, or Firm* — Edwin S. Flores; Chalker Flores, LLP

(57) ABSTRACT

The present invention includes composition and methods for making and using a combinatorial library to identify modified thioaptamers that bind to, and affect the immune response of a host animal, transcription factors such as IL-6, NF-κB, AP-1 and the like. Composition and methods are also provided for the treatment of viral infections, as well as, vaccines and vaccine adjuvants are provided that modify host immune responses.

14 Claims, 7 Drawing Sheets

(56) References Cited

U.S. PATENT DOCUMENTS

| | | | |
|---|---|---|---|
| 4,599,230 A | 7/1986 | Milich et al. | |
| 4,599,231 A | 7/1986 | Milich et al. | |
| 4,601,903 A | 7/1986 | Frasch | |
| 4,608,251 A | 8/1986 | Mia | |
| 5,204,884 A | 4/1993 | Leary et al. | |
| 5,218,088 A | 6/1993 | Gorenstein et al. | |
| 5,270,163 A | 12/1993 | Gold et al. | |
| 5,397,698 A | 3/1995 | Goodman et al. | |
| 5,436,327 A | 7/1995 | Southern et al. | |
| 5,475,096 A | 12/1995 | Gold et al. | |
| 5,503,978 A | 4/1996 | Schneider et al. | |
| 5,510,240 A * | 4/1996 | Lam | C07K 1/047 435/18 |
| 5,563,050 A | 10/1996 | Peyman et al. | |
| 5,576,302 A | 11/1996 | Cook et al. | |
| 5,582,981 A | 12/1996 | Toole et al. | |
| 5,587,361 A | 12/1996 | Cook et al. | |
| 5,599,797 A | 2/1997 | Cook et al. | |
| 5,602,000 A | 2/1997 | Hyman | |
| 5,607,923 A | 3/1997 | Cook et al. | |
| 5,620,963 A | 4/1997 | Cook et al. | |
| 5,635,488 A | 6/1997 | Cook et al. | |
| 5,639,603 A | 6/1997 | Dower et al. | |
| 5,639,873 A | 6/1997 | Barascut et al. | |
| 5,652,355 A | 7/1997 | Metelev et al. | |
| 5,660,985 A | 8/1997 | Pieken et al. | |
| 5,661,134 A | 8/1997 | Cook et al. | |
| 5,663,153 A | 9/1997 | Hutcherson et al. | |
| 5,668,265 A | 9/1997 | Nadeau et al. | |
| 5,670,637 A | 9/1997 | Gold et al. | |
| 5,696,249 A | 12/1997 | Gold et al. | |
| 5,705,337 A | 1/1998 | Gold et al. | |
| 5,734,041 A | 3/1998 | Just et al. | |
| 5,750,666 A | 5/1998 | Caruthers et al. | |
| 5,756,291 A | 5/1998 | Griffin et al. | |
| 5,763,595 A | 6/1998 | Gold et al. | |
| 5,770,367 A | 6/1998 | Southern et al. | |
| 5,795,721 A | 8/1998 | Rabin et al. | |
| 5,801,154 A | 9/1998 | Baracchini et al. | |
| 5,804,143 A | 9/1998 | Leary et al. | |
| 5,804,445 A | 9/1998 | Brasier | |
| 5,811,533 A | 9/1998 | Gold et al. | |
| 5,844,106 A | 12/1998 | Seela et al. | |
| 5,853,984 A | 12/1998 | Davis et al. | |
| 5,874,219 A | 2/1999 | Rava et al. | |
| 6,011,020 A | 1/2000 | Gold et al. | |
| 6,069,008 A | 5/2000 | Bennett et al. | |
| 6,120,763 A | 9/2000 | Fakhrai et al. | |
| 6,171,792 B1 | 1/2001 | Brent et al. | |
| 6,180,348 B1 | 1/2001 | Li | |
| 6,242,246 B1 | 6/2001 | Gold et al. | |
| 6,319,668 B1 | 11/2001 | Nova et al. | |
| 6,346,611 B1 | 2/2002 | Pagratis et al. | |
| 6,369,208 B1 | 4/2002 | Cole et al. | |
| 6,423,493 B1 | 7/2002 | Gorenstein et al. | |
| 6,458,543 B1 | 10/2002 | Gold et al. | |
| 6,503,715 B1 | 1/2003 | Gold et al. | |
| 6,514,948 B1 | 2/2003 | Raz et al. | |
| 6,544,776 B1 | 4/2003 | Gold et al. | |
| 6,551,795 B1 | 4/2003 | Rubenfield et al. | |
| 6,569,630 B1 | 5/2003 | Vivekananda et al. | |
| 6,610,504 B1 | 8/2003 | Yuan | |
| 6,713,616 B2 | 3/2004 | Pagratis et al. | |
| 6,716,629 B2 | 4/2004 | Hess et al. | |
| 6,725,526 B2 | 4/2004 | Lille | |
| 6,780,582 B1 | 8/2004 | Wagner et al. | |
| 6,844,165 B2 | 1/2005 | Hutchens et al. | |
| 6,867,289 B1 | 3/2005 | Gorenstein et al. | |
| 7,125,660 B2 | 10/2006 | Stanton et al. | |
| 7,338,762 B2 * | 3/2008 | Gorenstein et al. | 435/6.11 |
| 7,709,192 B2 | 5/2010 | Gold | |
| 2001/0014461 A1 | 8/2001 | Hutchens et al. | |
| 2001/0014479 A1 | 8/2001 | Hutchens et al. | |
| 2001/0034330 A1 | 10/2001 | Kensil | |
| 2003/0143732 A1 | 7/2003 | Fosnaugh et al. | |
| 2003/0144229 A1 | 7/2003 | Klinman et al. | |
| 2003/0162190 A1 | 8/2003 | Gorenstein et al. | |
| 2003/0162216 A1 | 8/2003 | Gold et al. | |
| 2003/0186906 A1 | 10/2003 | Schlingensiepen et al. | |
| 2004/0191905 A1 | 9/2004 | Stevenson et al. | |
| 2004/0242521 A1 | 12/2004 | Gorenstein et al. | |
| 2008/0255005 A1 * | 10/2008 | Gorenstein et al. | 506/38 |

FOREIGN PATENT DOCUMENTS

| | | |
|---|---|---|
| EP | 1 157 132 | 11/2001 |
| WO | 8902472 | 3/1989 |
| WO | 92/14842 A1 | 9/1992 |
| WO | 92/14843 A1 | 9/1992 |
| WO | 93/08296 A1 | 4/1993 |
| WO | 9401550 A1 | 1/1994 |
| WO | 96/19572 A1 | 6/1996 |
| WO | 9628457 | 9/1996 |
| WO | 96/41019 A1 | 12/1996 |
| WO | 99/31275 A1 | 6/1999 |
| WO | 9954506 A1 | 10/1999 |
| WO | 0024404 A1 | 5/2000 |
| WO | 00/47774 A1 | 8/2000 |
| WO | 03050290 A1 | 6/2003 |
| WO | 2004026260 A1 | 4/2004 |
| WO | 2005/003291 A2 | 1/2005 |
| WO | 2005018357 A1 | 3/2005 |
| WO | 2005037053 A1 | 3/2005 |
| WO | 2005032455 A1 | 4/2005 |

OTHER PUBLICATIONS

Somasunderam, A., et al. "Combinational Selection, Inhibition and Antiviral Activity of DNA Thioaptamers Targeting Rnase H Domain of HIV-1 Reverse Transcriptase." Biochemistry (2005) 4:10388-395.

Song, E., et al., "RNA Interference Targeting Fas Protects Mice from Fulminant Hepatitis," Nat Med, (2003), 9, 347-351.

Song, E., et al., "Sustained Small Interfering RNA-Mediated Human Immunodeficiency Virus Type 1 Inhibition in Primary Macrophages," J Virol. Jul. 2003, 77(13):7174-81.

Tonkinson, J.L., "Cellular Pharmacology and Protein Binding of Phosphoromonothioate and Phosphorodithioate Oligodeoxynucleotides: A Comparative Study," Antisense Research and Development (1994), 4:269-278.

Ueda, Takuya, et al., Phosphorothioate-Containing RNAs Show mRNA Activity in the Prokaryotic Translation Systems in Vitro., Nucleic Acids Research, (1991), vol. 19, No. 3, pp. 547-552.

Wang, et al., "Identification of Proteins Bound to a Thioaptamer Probe on a Proteomics Array," Biochemical and Biophysical Research Communications (2006), 347:586-593.

Xia, H.B. et al., "siRNA-Mediated Gene Silencing in Vitro and in Vivo," Nat Biotech, (2002), 20, 1006-1010.

Yamamoto, et al., "Ribozyme Oligonucleotides Against Transforming Growth Factor-β Inhibited Neointimal Formation After Vascular Injury in Rat Model," Circulation (2000), 102:1308-1314.

Yang, X., et al., "Construction and Selection of Bead-Bound Combinatorial Olignucleoside Phosphorothioate and Phosphoroditihioate Aptamer Libraries Designed for Rapid PCR-Based Sequencing," Nucleic Acid Research (2002), 30:132-140.

Yang, X., et al., "Immunofluorescence Assay and Flow Cytometry Selection of Bead Bound Aptamers," Nucleic Acid Research (2003), 31:1-8 (of e54).

Volk, D. E., et al., "Solution Structure and Design of Dithiophosphate Backbone Aptamers Targeting Transcription Factor NF-kappaB," Bioorganic Chemistry, (2002), 30:396-419.

Yokota, T., et al. (Taira), "Inhibition of Intracellular Hepatitis C Virus by Synthetic and Vector-Derived Small Interfering RNAs," EMBO Rep., (2003), 4(6), 602-608.

Walz, et al., "Amino Acid Sequences of Human Prothrombin Fragments 1 and 2," Proc Natl Acad Sci (1977), 74:1969-1972.

Zhang, Haidi, et al., "Single Processing Center Models for Human Dicer and Bacterial RNase III," (2004), Cell, vol. 118, pp. 57-68.

(56) References Cited

OTHER PUBLICATIONS

International Search Report and Written Opinion for PCT/US2006/019263 dated Aug. 4, 2008.
Database Geneseq, "NF-kappaB binding thymidine phosphorodithioate aptamer #1," retrieved from EBI accession No. GSN:AAA53511.
Partial Supplementary European Search Report for Application No. 04776088.9 (PCT/US2004/016246) dated Jun. 29, 2007.
Partial Supplementary European Search Report for Application No. 04809405.6 (PCT/US2004/016061) dated Jul. 3, 2007.
Pletnev, S.V., et al., "Locations of Carbohydrate Sites on Alphavirus Glycoproteins Show that E1 Forms an Icosahedral Scaffold," Cell (2001), 105(1), 127-36.
Raveh, et al., "Peptidic Determinants and Structural Model of Human NDP Kinase B (Nm23-H2) Bound to Single-Stranded DNA." Biochemistry (2001), 40:5882-5893.
Redman, J. E., et al., "Automated Mass Spectrometric Sequence Determination of Cyclic Peptide Library Members," published online Dec. 14, 2002, Journal of Combinatorial Chemistry, 5:33-40.
Semizarov, D., et al., "Specificity of Short Interfering RNA Determined Through Gene Expression Signatures," PNAS, (2003), 00(11), 6347-52.
Smith, D., "Sensitivity and specificity of photoaptamer probes," Molecular and Cellular Proteomics 2.1 (2003), 2:11-18.
Amarzguioui, M., et al., "Tolerance for mutations and chemical modifications in a siRNA Nuc Acids" (2003), Res, 31, 589-595.
Bane, et al., "DNA Affinity Capture and Protein Profiling by SELDI-TOF Mass Spectrometry: Effect of DNA Methylation," Nuceic Acids Research (2002), 30:e69.
Braasch, D.A., et al., "Antisense Inhibition of Gene Expression in Cells by Oligonucleotides Incorporating Locked Nucleic Acids: Effect of mRNA Target Sequence and Chimera Design," Nucleic Acids Res, (2002) 30(23), 5160-5167.
Braasch, et al., "RNA Interference in Mamalian Cells by Chemically-Modified RNA," Biochemistry (2003), 42:7967-7975.
Caplen, N.J., et al., "Specific Inhibition of Gene Expression by Small Double-Stranded RNAs in Invertebrate and Vertebrate Systems," PNAS, 98, (2001) 9742-9747.
Cassiday, et al., "Binding Stoichiometry of a FNA Aptamer and its Transcription Factor Target," Analytical Biochemistry (2002), 306:290-297.
Chi, J.T., "Genomewide View of Gene Silencing by Small Interfering RNAs," PNAS, (2003),100(11), 6343-6346.
Cordingley, H. C., et al., "Multifactorial screening desing and analysis of SELDI-TOF ProteinChip® array optimization experiments," BioTechniques (2003), 34:364-373 (pp. 366-367 are not present in this reference).
Dick, et al., "Aptamer-Enhanced Laser Desorption/Ionization of Affinity Mass Spectrometry," Analytical Chemistry (2004), 76:3037-3041.
Doucette, et al., "Investigation of the Applicability of a Sequential Digestion Protocol Using Trypsin and Leucine Aminopeptidase M for Protein Identification by Matrix-Assisted Laser Desorption/Ionization—Time of Flight Mass Spectrometry," Proteomics (2001), 1:987-1000.
Elbashir, et al., "RNA Interference is Mediated by 21- and 22-nucleotide RNAs," Genes and Development (2001), 15:188-200.
Elbashir, et al., "Functional Anatomy of siRNAs for Mediating Efficient RNAi in *Drosophilia melanogaster* Embryo Lysate," EMBO Journal (2001), 20:6877-6888.
Fire, et al., "Potent and Specific Genetic Interference by dsRNA in C.elegans," Nature, (1998) 391, 806.
Franz, A. H., et al., "High-Throughput One-Bead-One-Compound Approach to Peptide-Encoded Combinatorial Libraries: MALDI-MS Analysis of Single Tentagel Beads," published online Jan. 18, 2003, Journal of Combinatorial Chemisty, 5:125-137.
Gilmore, T.D., "Introduction to NF-κB: Players, Pathways, Perspectives," Oncogene (2006), 25:6680-6684.
Gitlin, L., et al., "Short Interfering RNA Confers Intracellular Antiviral Immunity in Human Cells," Nature, (2002) 418, 430-434.

Gotham, S., "Antisense and SiRNA Technologies—SMi Conference," Idrugs (2003), 6:211-214.
Hartmann, G., et al., "Mechanism and Function of a Newley Identified CpG DNA Motif in Human Primary B Cells," J Immunol (2000) 164:944-952.
Hu, W., et al., "Inhibition of Retroviral Pathogenesis by RNA Interference," Curr Biol, (2002) 12, 1301-1311.
Jackson, A.L., et al., "Expression Profiling Reveals Off-Target Gene Regulation by RNAi," Nat Biotech, (2003), 21 (6), 635-637.
Jacque, J.M., et al., "Modulation of HIV-1 Replication by RNA Interference," Nature, (2002), 418, 435-438.
Jansen, B. and U. Zangemeister-Witte, "Antisense Therapy for Cancer—The Time of Truth," Lancet Oncol, (2002), 3, 672-683.
Jayasena, S. D., "Aptamers: An Emerging Class of Molecules that Rival Antibodies in Diagnostics," Clinical Chemistry (1999), 45:1628-1650.
Jhaveri, S., et al., "In Vitro Selection of Phosphorothiolated Aptamers," Bioorganic and Medicinal Chemistry Letters (1998), 8:2285-2290.
Kawasaki, H., et al (Taira), "siRNAs Generated by Recombinant Human Dicer Include Specific and Significant but Target Site-Independent Gene Silencing in Human Cells," Nuc Acids Res, (2003), 31(3), 981-987.
King, D. et al., "Combinatorial Selection and Binding of Phosphorothioate Aptamers Targeting Human NF-kappa B RelA (p65) and p50," Biochemistry (2002), 41:9696-9706.
King, D.J., "Selection, Binding and Design of Phosphorothioate Duplex Aptamers for the Transcription Factors NF-IL6 and NP-KB," dissertation Aug. 2001.
Krieg, et al., "The role of CpG dinucleotides in DNA Vaccines," Trends in Microbiology (1998), 6:23-26.
Lam, K. S., et al., "The "One-Bead-One-Compound" Combinatorial Library Method," Chem. Rev. (1997), 97:411-448.
Lebl, M., et al., "One-Bead-One-Structure Combinatorial Libraries," Biopolymers (1995), 37:177-198.
Lescar, J., et al., "The fusion glycoprotein shell of Semliki Forest virus: an icosahedral assembly primed for fusogenic activation at endosomal pH," Cell (2001), 105(1), 137-48.
Marshall, W. S., et al., "Inhibition of Human Immunodeficiency Virus Activity by Phosphorodithioate Oligodeoxycytidine," Proc Natl Acad Sci (1992), 89:6265-6269.
Marshall, W. S., et al., "Phosphorodithioate DNA as a Potential Therapeutic Drug," Science (1993), 259:1564-1570.
Mata, J. E., et al., "A Hecxameric Phosphorothioate Oligonucleotide Telomerase Inhibitor Arrests Growth of Burkitt's Lymphoma Cells in Vitro and in Vivo," Toxicology and Applied Pharmacology (1997), 144:189-197.
McCaffrey, A.P., et al., "Inhibition of Hepatitis B Virus in Mice by RNA Interference," Nat Biotechnol, (2003), 21(6), 639-44.
Merchant, et al., "Recent Advancements in surface-enhanced laser desorption/ionization—time of flight-mass spectrometry," Electrophoresis (2000), 21:1164-1167.
Nakamura, H., et al., "How does Rnase H recognize a DNA-RNA hybrid?" PNAS (1991) 88:11535-539.
Nickens, et al., "Inhibition of HIV-1 reverse transcriptase by RNA aptamers in *Escherichia coli*," RNA (2003), 9:1029-1033.
Novina, C.D., et al., "siRNA-Directed Inibition of HIV-1 Infection," Nat Med, (2002) 8, 681-686.
Opalinska, et al., "Nucleic-Acid Therapeutics: Basic Principles and Recent Applications," Nature Reviews (2002), 1:503-514.
Parrish, S., et al., "Functional Anatomy of a dsRNA Trigger: Differential Requirement for the Two Trigger Strands in RNA Interference," (Fire research group), Mol Cell, (2001), 6, 1077-87.
Etienne, M., et al., "Analytical investigation of the chemical reactivity and stability of aminopropyl-grafted silica in aqueous medium." Talanta, May 1, 2003, vol. 59, No. 6, pp. 1173-1188.
Andreola, M.-L., et al., "DNA Aptamers Selected against the HIV-1 RNase H Display in Vitro Antiviral Activity," Biochemistry (2001), 40:10087-10094.
Antsypovich, et al. (1998) Cross-linked DNA duplexes: Exonuclease stability and interaction with the nucleic transcription factor of the κ light-chain enhancer (NF-κB).

(56) References Cited

OTHER PUBLICATIONS

Berglund, et al., "A high affinity binding site for the HIV-1 nucleocapsid protein." Nucleic Acids Research, 1997, vol. 25, No. 5, pp. 1042-1049.

Bielinska, A., et al., "Regulation of Gene Expression with Double-Stranded Phosphorothioate Oligonucleotides." Science 250, (1990), pp. 997-1000.

Boiziau, et al., "DNA Aptamers Selected Against the HIV-1 trans-Activation-responsive RNA Element Form RNA-DNA Kissing Complexes," J Biol Chem (1999), 274:12730-72737.

Braasch, D.A. et al., Novel antisense and peptide nucleic acid strategies for controlling gene expression. Biochemistry, 2002, vol. 41, pp. 4503-4510.

Elgemeie, G., "Thioguanine, Mercaptoputine: Their analogs and nucleosides as antimetabolites." Current Pharmaceutical Design, 2003, pp. 2627-2642.

European Office Action for 03816480.2 dated Dec. 15, 2009.

Gish, et al., "DNA and RNA Sequence Determination Based on Phosphorothioate ChemistryScience." 1988, 240:1520-1522.

Kanaori, et al., "Effect of phosphororothioate chiraliy on i-Motif structure and stability." Biochemistry, 2004, 43, pp. 5672-5679.

Kunsch, et al. (1992) Selection of Optimal κB/Rel DNA-Binding Motifs: Interaction of Both Subunits of NF-κB with DNA is Required for Transcriptional Activation. Molecular and Cellular Biology, Oct. 1992, vol. 12, No. 10, p. 1412-4421.

Lebruska, L.L. & Maher, I.L.J. (1999) "Selection and Characterization of an RNA Decoy for Transcription Factor NF-κB.," Biochemistry 38, 3168-3174.

PCT International Search Report and Written Opinion of the International Searching Authority, PCT/US04/16061, Jul. 10, 2006.

Sazani, et al., "Nuclear antisense effects of neutral, anionic and cationic oligonucleotide analogs." Nucleic Acids Research, 2001, 29(19):3965-3974.

Seliger, H. et al., "Synthetic Oligonucleotide Combinatorial Libraries—Tools for Studying Nucleic Acid Interactions." Nucleosides & Nucleotides, 16 :5-6, pp. 703-710, 1997.

Stec, et al. "Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside phosphorothioate)s and Chimeric PS/PO Oligonucleotides." J. Am. Chem. Soc., 1997, vol. 120, pp. 7156-7167.

Sterner, et al. "Use of Biocarrier Beads and Flow Cytometry for Single-Cells Studies of Fibronectin Gene Regulation in Dibutyrl Cyclic AMP Reverse Transformed CHO-K1 Cells." Cell Biophysics, 1988, vol. 15, pp. 159-171.

Yang, X., et al., "Aptamers containing thymidine 3'-O-phosphorodithioates: synthesis and binding to nuclear factor-κB," Bioorganic & Med. Chem. Letter, 1999, Vo. 9, 3357-3362.

Andreola, M., et al., "Towards the Selection of Phosphorothioate Aptamers: Optimizing In Vitro Selection Steps with Phosphorothioate Nucleotides," European Journal of Biochemistry, (2000), 267:5032-5040.

Koller, E., et al., "Elucidating Cell Signaling Mechanisms Using Antisense Technology," Trends Pharm Sci, Apr. 2000, vol. 21, pp. 142-148.

Miller, V.M.., et al., "Allele-specific silencing of dominant disease genes," PNAS, Jun. 10, 2003, vol. 100, No. 12, pp. 7195-7200.

NFKBIA nuclear factor of kappa light polypeptide gene enhancer in B-cells, Entrez Gene, Dec. 14, 2006, pp. 1-7.

Database Geneseq, "Biological interaction related oligonucleotide duplex 151," retrieved from EBI accession No. GSN:ADD43697, Jan. 15, 2004, 2 pages.

\* cited by examiner

STRUCTURE BASED AND COMBINATORIALLY SELECTED OLIGONUCLEOSIDE PHOSPHOROTHIOATE AND PHOSPHORODITHIOATE APTAMER TARGETING AP-1 TRANSCRIPTION FACTORS

CROSS-REFERENCE TO RELATED APPLICATIONS

This application is a divisional application and claims priority based on U.S. patent application Ser. No. 10/851,864, filed May 20, 2004, which claims priority to U.S. Provisional Application Ser. No. 60/472,890, filed May 23, 2003, the contents of each of which are incorporated by reference herein in their entireties.

STATEMENT OF FEDERALLY FUNDED RESEARCH

This work was supported by the following United States Government grants DARPA (9624-107 FP), NIH (AI27744) and NIEHS (ES06676). The government has certain rights in the invention. Without limiting the scope of the invention, its background is described in connection with oligonucleotide agents and with methods for the isolation and generation thereof.

TECHNICAL FIELD OF THE INVENTION

The present invention relates in general to the field of thioaptamers, and more particularly, the use of thioaptamers for screening, including high-throughput screening, of primary or secondary target molecules by using thioated aptamers bound to a substrate with specific targeting to the AP-1 family of transcription factors and for the treatment of viral infections, as well as, vaccines and vaccine adjuvants that modify host immune responses.

BACKGROUND OF THE INVENTION

Virtually all organisms have nuclease enzymes that degrade rapidly foreign DNA as an important in vivo defense mechanism. The use, therefore, of normal oligonucleotides as diagnostic or therapeutic agents in the presence of most bodily fluids or tissue samples is generally precluded. It has been shown, however, that phosphoromonothioate or phosphorodithioate modifications of the DNA backbone in oligonucleotides can impart both nuclease resistance and enhance the affinity for target molecules, such as for example the transcriptional activating protein NF-κB.

Recent world events have heightened the awareness of possible bioterrorist threats. Hemorrhagic fever viruses (category A bioweapon agents) have reportedly been weaponized by the former Soviet Union and the United States (Borio et al., 2002; Hawley & Eitzen, 2001). Despite the awareness of the potential of Viral Hemorrhagic Fever viruses (Lassa, Junin), Encephalitic viruses (West Nile, VEE) and other agents both as bioweapons and as emerging viral diseases, few therapeutic options are available to those infected. Apart from supportive therapy, the only drug for treating Arenavirus infections is Ribavirin and it is only partially effective (McCormick et al, 1986a; Shulman, 1984; Enria et al., 1987) while there are no efficacious drugs to treat victims of West Nile infections (Peterson and Marfin, 2002). There is an urgent need to expand the current therapeutic armamentarium, which is hindered, at least in part, by a lack of in-depth knowledge concerning the mechanisms of Arenaviral pathogenesis (Peters & Zaki, 2002).

Arenavirus pathogenesis stems from host immune response dysregulation and endothelial dysfunction (Peters & Zaki, 2002; Ignatyev et al., 2000; McCormick & Fisher-Hoch, 2002; Walker et al., 1982; McCormick et al., 1986b; Marta et al., 1999). West Nile pathogenesis is associated with the inability of host immune response to limit virus replication to levels below that required for viral invasion of the CNS (Solomon and Vaughn, 2002).

Lassa fever, a human arenavirus hemorrhagic fever virus endemic in West Africa, affects up to 300,000 people annually and is responsible for up to 3000 deaths (McCormick, et al., 1987). Lassa Fever virus is difficult to study due to its hazardous nature (a BSL4 agent) Junin Virus is the causative agent of Argentine hemorrhagic fever (AHF). The annual incidence varies between 100-4000 cases/yr. AHF has a case fatality rate of 15-30% and is also a BSL4 agent. A well-established animal model that resembles Lassa Fever, using the non-pathogenic New World Arenavirus, Pichinde virus (Jahrling et al., 1981) has been used to study this class of pathogens. Serial passage of Pichinde virus in guinea pigs was used to develop a virulent variant that produces a disease in guinea pigs that mimics human Lassa Fever in many important respects including: viremia correlates with disease outcome (Johnson et al., 1987; Aronson et al., 1994), a relative paucity of pathologic findings in lethally infected animals (Walker, et al., 1982; Connolly, et al., 1993), terminal vascular leak syndrome (Katz & Starr, 1990) and distribution of viral antigens within the host (Connolly et al., 1993; Shieh et al., 1997; Aronson, unpublished data). Macrophage responses to the attenuated Pichinde virus, P2, with the virulent Pichinde variant, P18 as well as reassortants of the two variants (Zhang et al., 1999; Zhang et al., 2001; Fennewald et al., 2002) may be used to compare and modify the immune response to viral infection.

West Nile virus (Category B virus) is a mosquito-borne flavivirus that is a neuropathogen in humans, equines and avians (Solomon and Vaughn, 2002; Petersen and Marfin, 2002). Humans become infected by the bite of an infected mosquito. The viruses are then thought to replicate in the skin before being transported to the local lymph nodes. West Nile may then spread via the blood to other organs including the liver, spleen, heart and kidney and eventually the brain. West Nile virus may spread to the CNS via either hematogenous spread or via the olfactory mucosa where there is no blood-brain barrier. West Nile is an emerging pathogen in the US, spreading across the country since it was first identified in New York in 1999. As of Oct. 3, 2002, the CDC has reported 2530 cases of West Nile virus infection with 125 deaths in 32 states. West Nile is also responsible for major outbreaks in other countries including Tunisia, Romania, Algeria, Russia and Israel among others. Case fatality rates range from 4-29%. Age is a risk factor in the development of severe West Nile disease with many patients exhibiting substantial morbidity. Presently, treatment for West Nile is limited to supportive intervention. There is no evidence that either interferon or Ribavirin treatment is efficacious (Petersen and Marf1in, 2002).

Arenavirus Hemorrhagic Fevers, such as Lassa fever, Junin, Argentine hemorrhagic fever, Bolivian hemorrhagic fever and Venezuelan hemorrhagic fever, have several features in common with sepsis and the systemic inflammatory response syndrome, including fulminant clinical course, fever, shock, capillary leak syndrome, decreased myocardial contractility, abnormalities of coagulation and platelet function, and elevated serum levels of TNFα (Aronson et al., 1994; Cummins, 1990). Arenaviruses are non-cytopathic viruses with a tropism for macrophages and other reticuloendothelial cells (Cummins, 1990; Peters et al., 1987); the pathogenesis of these diseases is believed to involve excessive production of pro-inflammatory cytokines (Aronson et al., 1995; Peters et al., 1987). Unpublished data (Bausch et al., CDC) show cytokines to be massively activated in human Lassa fever, and also confirm that Lassa virus can directly induce cytokine secretion by infecting human macrophages in vitro (Mahanty et al., CDC, unpublished). Alternatively, there is evidence that a swift elaboration of pro-inflammatory cytokines and early engagement of the (innate) immune response may help protect of the infected host from lethal disease in various hemorrhagic fever syndromes (Peters et al., 1987).

Endotoxic shock results from an innate, anaphylactic response to bacterial lipopolysaccharide (LPS). The NF-κB transcription factor, in conjunction with other cellular transcription factors, plays a critical role in gene activation, especially in acute phase and inflammatory responses (Baeuerele, 1998; Barnes and Karin, 1997), and in particular endotoxic shock, a complex pathophysiological state which is considered to be an exaggerated or dysregulated systemic acute inflammatory response syndrome initiated by the binding of bacterial LPS complexed with lipopolysaccharide binding protein (LBP) to the CD14 receptor on macrophages. A series of intracellular signaling events, in which NF-κB activation figures importantly leads to enhanced transcription of proinflammatory mediators, including TNFα, IL-1 and inducible nitric oxide synthase, ultimately promoting vasodilatation, capillary leakiness, and myocardial suppression (Murphy et al., 1998). In well-established mouse endotoxemia models, rapid transient increases in NF-κB DNA-binding activity can be detected in the nuclei of macrophages and other cell types (Boher, et al., 1997); similar observations have been made in human sepsis (Velasco et al., 1997).

The AP-1 transcription factor family include the dimeric basic region leucine zipper proteins that belong to the Jun (c-Jun, JunB, JunD), Fos (c-Fos, FosB, Fra-1, Fra-2) Maf (c-Maf, MafB, MafA, MafG/F/K, Nrl) and ATF/CREB (CREB, CREBP-2, ATF1, ATF2, LRF1/ATF3, ATF4, ATFa, ATF6, B-ATF, JDP1, JDP2) subfamilies which recognize either 12-O-tetradecanoylphorbol-13-acetate (TPA) response elements (5'-TGAG/CTCA-3') or cAMP response elements (CRE, 5'-TGACGTCA-3') (Chinenov and Kerppola, 2001; Shaulian and Karin, 2002). These transcription factor binding sites are elements in the promoters and enhancers of numerous mammalian genes including IL-2, IL-3, IL-4, IL-5, IFNβ, TNFα and GM-CSF (Chineov and Kerppola, 2001). The c-Jun protein is the most potent transcription factor. The c-Fos proteins, which cannot homodimerize can form heterodimers with c-Jun and thereby enhance their DNA binding activities. The c-Fos, and FosB proteins contain transactivation domains, however, Fra1, Fra2 and some splice variants of FosB do not. CREB and ATF1 can form homodimers and heterodimers but do not combine with other ATF proteins. ATF2, ATFa, CREBP-2, ATF3, ATF4 and ATF6 combine both with themselves and with specific Jun and/or Fos family members. C-Fos and Fra1 can heterodimerize with ATF4, but not with ATF2 and ATF3.

There are numerous other possible homodimers and heterodimers possible among this large group of BZIP proteins. Jun, Fos and ATF family members can also bind to DNA upon association with certain Maf, C/EBP and non-bZIP member factors like NF-κB, NFAT and Smad. This can direct AP-1 components to promoter sequences that only slightly resemble consensus AP-1 and ATF motifs. This variation in dimer partner and DNA binding site specificity is assumed to provide AP1 subunits with a high level of flexibility in gene regulation. The regulation of AP-1 family of transcription factor activity is complex but briefly regulation occurs through: 1) changes in jun and fos gene transcription and mRNA turnover, 2) Fos and Jun protein turnover, 3) post-translational modifications of both Fos, Jun other family proteins that modulate their activities, and 4) interactions with other transcription factors (Shaulian and Karin, 2001,2002). AP-1 activity is induced by growth factors, cytokines, neurotransmitters, polypeptide hormones, cell/matrix interactions, bacterial and viral infections and a variety of environmental stresses. These activators stimulate a series of signaling events that involve a variety of protein kinases including MAPKs, ERKs and JNKs. Members of the Fos and Jun protein families participate in the regulation of a variety of cellular processes including cell proliferation, differentiation, apoptosis, oncogenesis, inflammation, and immunity (Chinenov and Kerppola, 2001).

SUMMARY OF THE INVENTION

The present invention demonstrates the use of "Thioaptamers™" to prevent Arenavirus and Flavivirus induced perturbations of the host response that lead to disease. Furthermore, the present invention provides for novel therapeutic interventions for the treatment of hemorrhagic fevers, encephalitic viruses and other viral infections, resulting from their use as bioweapons or as emerging diseases. For example, modified thioaptamers were used to demonstrate modulation of NF-κB and AP-1 to increase the survival of Arenavirus infected guinea pigs and mice infected with West Nile virus in a well-established model system. The present invention was also used to protect against viral infection with a neuropathologic viral infection. The modified thioaptamers of the invention were created and used to protect mice challenged with West Nile virus in a well-established model system.

The present invention is based on the recognition that thiomodified aptamers may be designed, isolated and used to manipulate transcription factors such as NFκB and AP-1 to interdict the pathogenetic sequence, or even boost early protective innate immune responses (FIG. 1). To demonstrate the feasibility of using the modified thioaptamers disclosed herein at physiological concentrations, animal model systems were used that models both severe fatal disease and self-limited infection with mild disease. For example, a well-recognized and widely used guinea pig model for Lassa Fever uses the New World arenavirus Pichinde (PIC) (Peters et al., 1987) was used and adapted to study pathogenesis by comparing an attenuated variant of PIC (P2) and a closely related virulent variant derived by serial guinea pig passage (P18) (Jahrling et al., 1981).

The present invention also uses the modified thio-aptamers to manipulate NF-κB levels in vivo. For example, the modified thioaptamers of the present invention were used to modify toxic shock via IκBα overexpression increased mouse survival after high dose LPS challenge. The modified thioaptamers of the present invention may be used to target the five NF-κB/Rel family proteins, which combine to form 15 homo- and heterodimers. By targeting target one or more of the five NF-κB/Rel family members, the present invention is used to modify one or more of the signaling pathways that regulate a specific signaling function upon translocation across the cell nuclear membrane and binding to a gene's promoter region.

While it is recognized that the AP-1 and NF-κB transcription factor families both play key roles in the immune response and both represent appropriate targets for therapies for viral infections, it has not been possible to modify in a physiologic manner their activities. The present invention allows for the modification of transcription factor activities using modified thioaptamers that act under physiological conditions and at physiological levels to regulate transcriptional activation. Such regulation may be used to modify responses to diseases involving pathogenic or disfunctional inflammatory responses such as cancer, heart disease, inflammatory bowel disease, rheumatoid arthritis and lupus.

The present invention was used to modulate induction of CREB, a transcription factor regulated by cyclic AMP (cAMP) signaling. The modified thioaptamers were used to modulate CREB activity and were demonstrated to modify virulent and attenuated Arenavirus infection. The CREB protein is also a member of the AP-1 family of transcription factors whose targeting by XBY-S2 has provided protection for animals infected with arenavirus and flavivirus. cAMP is a ubiquitous second messenger (Antoni et al., 2000) synthesized in cells by adenylyl cyclases in response to many extra-cellular stimuli. Most cellular effects of cAMP are mediated through the activation of cAMP dependent protein kinases (PKA) (Sassone, 1995). PKA phosphorylation of substrates in all cellular compartments regulates a large array of cellular processes (Feliciello et al., 2001). Cyclic AMP induces changes in gene expression that modulate macrophage apoptosis (von Knethen & Brüne, 2000) and could contribute to pathogenic inflammatory conditions and sepsis. There is also evidence for functional cross talk between cAMP signaling and the Jak/STAT pathway (Meloche et al., 2000). Agents that increase intracellular concentrations of cAMP inhibit IL-6 induced STAT activation in monocytes and interferon-β stimulated phosphorylation of Jak1, Tyk2, STAT1 and STAT2 in myeloma cells. Therefore, the modulation of the Jak/STAT pathway by cAMP is likely to play an important role in the regulation of immune and inflammatory responses, which may be regulated using the modified thiopatamers of the present invention.

The present invention provides a number of advantages due to the use of modified thioaptamers and combinatorial selection methods. The present invention provides very high affinity—nM to sum-nM (≥monoclonal IgMs and >non-substituted aptamers), target-specific aptamers, demonstrating single protein target binding within cellular extracts. The modified thioaptamers have greater resistance to cellular or serum nuclease degradation than normal backbone aptamers, or proteases towards antibodies. Due to the increased nuclease resistance, the aptamers disclosed herein may be packaged to have indefinite shelf-life, ease of storage as lyophilized powders at room temperatures, unlike unmodified RNA or antibodies and are relatively inexpensive to produce. Furthermore, the methods and compositions disclosed herein allow for high reproducibility in quality control, unlike diasteromeric mixtures for non-stereospecifically produced monothiophosphate aptamers, or protein production of antibodies. Finally, the use of bead-based thioaptamer libraries or library of libraries provides large combinatorial libraries readily selected by multicolor flow cytometry at very high speeds ($10^8$/hr).

In one embodiment, the present invention is a system and method for identifying both thioaptamer sequences and binding one or more proteins that include the steps of, incubating a thioaptamer library with a sample suspected of including one or more proteins, e.g., target proteins. The proteins that bind the thioaptamers are selected from the one or more thioaptamers of the library to which protein has bound, the proteins are identified using mass spectrometry and/or the thioaptamer is sequenced using, e.g., a method that includes PCR amplifying the aptamer followed by, cloning and sequencing. The thioaptamers may be on beads, e.g., as part of a one-bead, one-thioaptamer library and may be sequenced, e.g., directly on the beads.

The system and method may also include the step of separating the protein into fragments prior to separation by liquid chromatography followed by mass spectrometry. In an alternative method, the step of identifying the protein by mass spectrometry (MS) may be, e.g., time-of-flight (TOF) MS. In one example, prior to the step of identifying the protein, the protein may be extracted and then separated by liquid chromatography. The identification of the protein may be by surface enhanced laser desorption ionization (SELDI) or matrix assisted laser desorption ionization (MALDI) prior to MS. The thioaptamers may be attached to beads or a substrate, e.g., a semiconductor substrate. Semiconductor substrates may be used as arrays that permit detection of protein:thioaptamer binding and may further include detectors that are integral with the substrate (e.g., capacitance coupled devices) or even surface metal for surface plasmon resonance (SPR) detection. The thioaptamer library may even be a microarray on a substrate that does not include an integral detected, e.g., a glass slide on which a thioaptamer library has been disposed using, e.g., photolithography or digital optical chemistry. The location of protein binding on such a microarray may be detected using well known protein detection methods, e.g., fluorescence. The protein for use with the invention may be protein from a crude extract or even partially purified or isolated, e.g., one or more proteins isolated from a gel.

The system and method disclosed herein may further include the use of binding the thioaptamers to beads and sorting the beads to isolate and identify proteins that have specifically bound to the thioaptamers. For example, when using a thioaptamer library of beads, the beads may be sorted based on protein binding, e.g., based on fluorescence labeling of the aptamer and/or the protein using a flow-cytometer. The protein may be from a cell extract, which may even be a cell extract from a virally infected or diseased cell. Generally, the thioaptamers are attached to beads and the beads are substantially protein-free. When using a one-bead, one-thioaptamer (ODN) library or even a library of libraries the thioaptamers may be one or more beads that include an [S]-ODN and/or [$S_2$]-ODN combinatorial libraries. The ODNs may be single or double stranded and may include thio-modifications to one or both of the strands In one embodiment of the present invention the thioaptamer library includes, or is designed to include, sequence motifs for high affinity with cellular proteins selected from proteins that are members of, e.g., the AP-1, RBP-Jκ, NF-κB, NF IL-6, CREB and GRE protein families, and combinations thereof. In operation, the system and method may also include the step of comparing a first and a second incubation of one or more beads to a first and a second sample, respectively, wherein differences in binding are used to detect proteins that expressed differentially, e.g., proteins from a virally-infected (or diseased) cell or even a cancer cell. In an alternative embodiment, the method may also include the steps of binding the one or more thioaptamers to one or more beads, incubating the one or more thioaptamer beads with a cell extract from a cell wherein proteins from the cell extract are labeled with a first dye; incubating the one or more thioaptamers beads with a cell extract from a diseased-cell wherein proteins from the diseased-cell extract are labeled with a second dye, incubating the one or more thioaptamers beads with a cell extract from a diseased-cell pre-treated with thioaptamers or other drugs, wherein the proteins of the diseased-cell but drug-treated, are labeled with a third dye; and performing a three-color flow cytometry that measured the relative levels of the first, second and third dyes.

Another embodiment of the present invention is a complex combinatorial library that includes one or more concatenated thio-modified aptamers, wherein at least a portion of each of the aptamers is partially thio-modified. The one or more concatenated thioaptamers may be bound to a substrate, e.g., one or more beads, a semiconductor, a surface plasmon resonance surface (e.g., gold), a multi-well plate and the like. The concatenated aptamer may include two or more concatenated thio-modified aptamers, wherein one or more of the aptamers is partially thio-modified. In one example, the two or more concatenated thioaptamers may include nucleic acid sequences suspected of binding to nuclear regulatory factors, and may even be a library of thioaptamers. More particularly, the two or more concatenated thioaptamers may include nucleic acid sequences suspected of binding. NF-κB, RBP-Jκ, AP-1, NF IL-6, SP-1, GRE, SRE and the like. In one example, one or more of the thioaptamers may be a library of aptamers that binds to one or more transcritption factors and includes sequences or sequence motifs for transcription factor binding, e.g., a NF-κB, a RBP-Jκ, an AP-1, an NF IL-6, an SP-1, a GRE, an SRE motif and/or mixtures thereof.

The complex combinatorial library made by a method that includes the steps of synthesizing an aptamer bead library having a first thioaptamer and concatenating to each of the first thioaptamers a second aptamer or thioaptamer suspected of binding to, e.g., a nuclear regulatory factor. In fact, the first and second thioaptamers may even be suspected of binding the same nuclear regulatory factor or a different nuclear regulatory factor. Yet another embodiment of the present invention is a method of identifying a thio-modified therapeutic agent that includes mixing a sample suspected of including a DNA binding protein with a concatenated first and second thioaptamer under binding conditions and isolating the one or more DNA binding proteins that bind specifically to the concatenated aptamers.

Another embodiment of the present invention is a composition, adjuvant, vaccine and method of modifying an immune response that includes providing a host cell with aptamers that suppress the activity of a nuclear regulatory factor critical for activation of an immune response. The immune response may be an innate immune response, a cytotoxic or a helper T cell immune response. In one embodiment the thioaptamer modified the immune response by shifting the helper 1-type (Th1) to T helper 2-type (Th2) ratio. The immune response that is modified may be to a virus, a bacteria, a fungus, a cancer, a self-antigen, a heterologous antigen, a retrovirus, a hemorraghic virus or a neuropathologic virus, e.g., West Nile Virus. The immune response that is modified may be modified in vivo, in vitro and/or ex vivo. The modification of the immune response may be an increase or decrease of the immune response as measured by, e.g., antibody production, cytotoxic T cell activation, cytokine release, apoptosis, cell proliferation, cell killing, chromium release, nucleic or amino acid uptake or release and other methods known to those skilled in the immunological arts.

In one specific embodiment, the type of helper T cell response may be modified by providing a host or target cell with one or more thioaptamers that suppress the activity of a nuclear regulatory factor critical for activation of, e.g., a helper T cell response. The T cell immune response may be to, e.g., a virus, a bacteria, a fungus, a cancer, a self-antigen, a heterologous antigen, a retrovirus, a hemorraghic virus or even a neuropathologic virus. The modification to the immune response may be to a challenge to the innate or the adaptive immune response. The helper T cell response may be a T helper 1-type response or a T helper 2-type response.

Another embodiment of the invention is a vaccine that includes an antigen and a thioaptamer. The vaccine may be to an antigen from, e.g., a virus, a bacteria, a fungus, a cancer, a self-antigen, a heterologous antigen, a xenoantigen, a retrovirus, a hemorraghic virus or a neuropathologic virus. The vaccine may be provided in a lyophilized, a particulate or even a dissolved form and may even include one or more pharmaceutically acceptable salts, diluents, preservatives and the like. The antigen may be, e.g., a live-attenuated antigen or a heat-inactivated antigen. Examples of viral antigens include: hemorrhagic fever viruses, which include viruses from different viral families, e.g., Ebola, Marburg, Lassa fever, New World Arenavirus, Rift Valley Fever, yellow fever, Omsk hemorrhagic fever and Kyasanur Forest Disease viruses. Four viral families are generally implicated in hemorrhagic fever infections, including: (1) Arenaviridae (Lassa, Junin, Machupo, Guanarito, and Sabia viruses, which are the causative agents of Lassa fever and Argentine, Bolivian, Venezuelan, and Brazilian hemorrhagic fevers, respectively); (2) Filoviridae (Ebola and Marburg); (3) Flaviviridae (yellow fever, Omsk hemorrhagic fever, and Kyasanur Forest disease viruses); (4) Bunyaviridae (Rift Valley fever (RFV), Congo-Crimean hemorrhagic fever. Another target viral family includes Hantaviruses. Another antigen for targeting includes neuropathologic viruses, e.g., St. Louis encephalitis, Western equine encephalitis, Eastern equine encephalitis, California encephalitis serogroup (e.g., LaCrosse, Jamestown Canyon, Snowshoe Hare, Trivittatus, Keystone, and California encephalitis viruses), Powassan encephalitis, Venezuelan equine virus, Argentine equine encephalitis virus, Cache Valley virus and West Nile virus. Neuropathologic viruses fall into various viral families and are characterized by symptoms that include: fever of variable severity associated with neurologic symptoms ranging from headache to aseptic meningitis or encephalitis, headache, confusion or other alteration of the senses, nausea and vomiting. Signs may include fever, meningismus, cranial nerve palsies, paresis or paralysis, sensory deficits, altered reflexes, convulsions, abnormal movements and coma of varying degree.

The thioaptamers of the present invention may be an adjuvant that forms part of a vaccine, such as a composition that includes one or more partially thio-modified or even concatenated aptamers that modulate an immune response. When used as a vaccine, that thioaptamer adjuvant may also include at least one antigen. In addition to the examples hereinabove, the antigen may be a pathogen-associated molecular pattern antigen, e.g., a CpG molecule, a saccharide, a lectin, a polysaccharide and the like. As with the thioaptamers described hereinabove the adjuvant thioaptamer may include sequences for specific recognition and binding to nuclear regulatory factors, e.g., NF-AT, NF-κB, RBP-Jκ, AP-1, NF IL-6, SP-1, GRE and SRE. Examples of partially thioaptamers include one or more of the aptamers of SEQ ID NOS.: 2, 3, 4, 5, 6, 7, 8 and 9.

The thioaptamer may an adjuvant that includes one or more partially thioaptamers that bind to, e.g., a DNA binding protein and modulate an immune response, e.g., an innate or an adaptive immune response. The adjuvant may be provided with a physiologically acceptable aqueous vehicle, in a lyophilized, a particulate or even a dissolved form with or without an antigen, e.g., the antigen described hereinabove. The thioaptamer may be specific for one or more downstream nuclear regulatory factors that transduce a intracellular signal from a Toll-Like receptor, e.g., a Toll-Like receptor 2, a Toll-Like receptor 4 or a pathogen-associated molecular pattern receptor. The adjuvant may be a partially thioaptamer selected from SEQ ID NOS.: 2, 3, 4, 5, 6, 7, 8, 9, 56 and/or 58. Another embodiment of the present invention is a T cell adjuvant that includes, e.g., a peptide antigen and an aptamer wherein at least a portion of at least one nucleotide in the thioaptamer is thiophosphate-modified.

The present invention also includes a method of treating a hemorraghic viral infection that includes the steps of identifying a patient suspected of being infected with a hemorraghic virus and providing the patient with a therapeutic amount of a thioaptamer specific for a transcription factor involved in viral propagation or the immune cell response related to the virus. The transcription factor may be, e.g., NF-κB, RBP-Jκ, AP-1, NF IL-6, SP-1, GRE, SRE, mixtures thereof and the like. The thioaptamer will generally bind specifically to a protein, e.g., a transcription factor and may also include one or more of the aptamers of SEQ ID NOS.: 2, 3, 4, 5, 6, 7, 8 and 9, e.g.,

```
XBY-6:
5'-CCAGGAGAT_{S2}T_{S2}CCAC-3'           SEQ ID NO.: 1
3'-GG_{S2}TCC_{S2}TC_{S2}TAAGG_{S2}TG-5'

XBY-S2:
5'-CCAGT_{S2}GACTS_{S2}CAGT_{S2}G-3'     SEQ ID NO.: 2
3'-GG_{S2}TCAC_{S2}TGAG_{S2}TCAC-5'

XBY-S1:
5'-T_{S2}T_{S2}GCGCGCAACAT_{S2}G-3'      SEQ ID NO.: 3
3'-AACGCGCG_{S2}T_{S2}TG_{S2}TAC-5'

XBY-C2:
5'-CCAGTGACTCAGTG-3'                     SEQ ID NO.: 4
3'-GGTCACTGAGTCAC-5'

XBY-C1:
5'-TTGCGCGCAACATG-3'                     SEQ ID NO.: 5
3'-AACGCGCGTTGTAC-5'

5'-tGTGcAGGGACTgAtGaCGGt-3',             SEQ ID NO.: 6

5'-CtGTGCatCGAaGTTtGCAtTt-3',            SEQ ID NO.: 7

5'-AtGcAcAtCtCaGgAtGaCGGt-3',            SEQ ID NO.: 8

5'-AGTTGcAGGtCaGgACCCAtTt-3',            SEQ ID NO.: 9
``` wherein the lowercase letters represent the thiophosphate 3' to the base. In one examples, the method of treatment may be directed to a neuropathologic viral infection and include the steps of identifying a patient suspected of being infected with a neuropathologic virus; and providing the patient with a therapeutic amount of a partially thioaptamer specific for transcription factor involved in immune cell activation. A thioaptamer for use in the method of treatment may be XBY-S2.

Yet another embodiment of the present invention is a method for modifying an immune response that includes administering a composition that includes an antigen and one or more partially thio-modified aptamers or thioaptamers. The modifications to the immune response include, e.g., activation or deactivation of the innate immune response and/or modifications to the type of immune response mounted (humoral versus cell-based) such as a change in the profile of helper T cell involved with or "lead" the immune response. The composition may also include cytokines, e.g., interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-10 (IL-10), interleukin-11 (IL-11), interleukin-12 (IL-12), interleukin-13 (IL-13), Type I Interferon, Type II Interferon, tumor necrosis factor alpha (TNF-alpha), transforming growth factor-beta (TGF-beta), lymphotoxin migration inhibition factor, granulocyte-macrophage colony-stimulating factor (GM-CSF), monocyte-macrophage CSF, granulocyte CSF, vascular epithelial growth factor (VEGF), angiogenin, transforming growth factor (TGF-alpha), fibroblast growth factor, angiostatin, endostatin, mixtures or combinations thereof. The composition may also include one or more antigens, e.g., lipid A, phospholipase A2, endotoxins, staphylococcal enterotoxin B, heat shock proteins (HSPs), carbohydrates, Rh factors, DNA, nucleotides, RNA, mRNA, MART, MAGE, BAGE, GAGE, DAGE, mutant p53, tyrosinase, or a combination thereof. The aptamer may stimulate specialized antigen presenting cells (APCs), e.g., macrophages, dendritic cells and B cells or non-specialized immune or even non-immune cells. The aptamer may activate an innate immune response, e.g., through Toll-Like receptors that stimulate lymphocytes such as APCs, B cells and T cells. In one example, the aptamer activates an innate immune response that includes the simultaneous activation of macrophages and dendritic cells and of B cells and T cells. The aptamer may stimulate or suppress the immune response.

In one specific embodiment, the present invention includes a method for enhancing vaccine efficacy by administering a composition that includes a partially thioaptamer specific for a DNA binding protein and an antigen to a subject animal. The aptamer may also include a carrier molecule, e.g., liposomes, microcapsules, microspheres, mixtures or combinations thereof. The target immune response may be, e.g., to a cancer or a pathogenic infection. Alternatively, the target immune response may be an anaphylactic shock, allergic rhinitis, eczema, urticaria, anaphylaxis, transplant rejection, systemic lupus erthymatosus, rheumatoid arthritis, seronegative spondyloarthritides, Sjogren's syndrome, systemic sclerosis, polymyositis, dermatomyositis, Type I Diabetes Mellitus, Acquired Immune Deficiency Syndrome, Hashimoto's thyroiditis, Graves' disease, Addison's disease, polyendocrine autoimmune disease, hepatitis, sclerosing cholangitis, primary biliary cirrhosis, pernicious anemia, coeliac disease, antibody-mediated nephritis, glomerulonephritis, Wegener's granulomatosis, microscopic polyarteritis, polyarteritis nodosa, pemphigus, dermatitis herpetiformis, psoriasis, vitiligo, multiple sclerosis, encephalomyelitis, Guillain-Barre syndrome, Myasthenia Gravis, Lambert-Eaton syndrome, sclera, episclera, uveitis, chronic mucocutaneous candidiasis, Bruton's syndrome, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, or non-Hodgkin's lymphoma. The partially thioaptamer may be specific for a DNA binding protein, a cellular protein, a cell surface protein, a saccharide or lipid or combinations thereof. When provided in vaccine form, the thioaptamer (thioaptamer) and an antigen may be provided in dry form or even be disposed in a vehicle suitable for oral, intramuscular, subcutaneous, intravenous or parenteral administration, e.g., in a sterile saline solution. The partially thioaptamer may be specific for AP-1, NF-κB, NF IL-6, or combinations thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
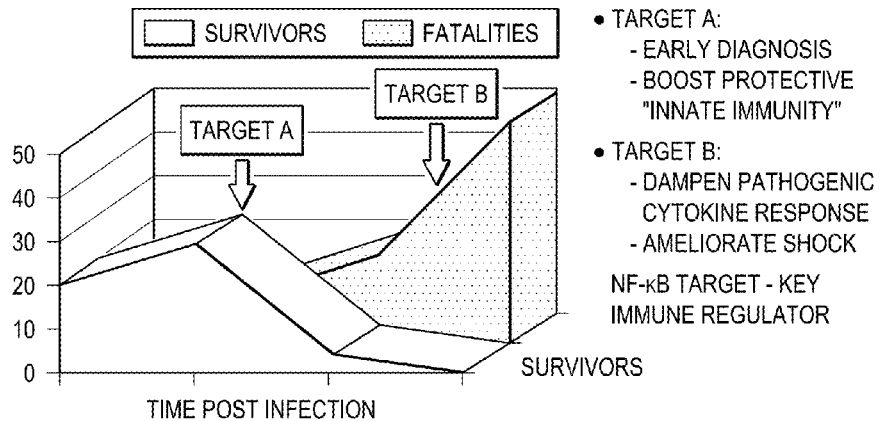
FIG. 1 is a schematic representation for immune responses post infection, in the left panel, Target A represents immune response clearing virus with patient survival, in the right panel Target B represents cytopathogenic immune response resulting in shock.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "synthesizing" of a random combinatorial library refers to chemical methods known in the art of generating a desired sequence of nucleotides including where the desired sequence is random. Typically in the art, such sequences are produced in automated DNA synthesizers programmed to the desired sequence. Such programming can include combinations of defined sequences and random nucleotides.

"Random combinatorial oligonucleotide library" means a large number of oligonucleotides of different sequence where the insertion of a given base at given place in the sequence is random. "PCR primer nucleotide sequence" refers to a defined sequence of nucleotides forming an oligonucleotide which is used to anneal to a homologous or closely related sequence in order form the double strand required to initiate elongation using a polymerase enzyme. "Amplifying" means duplicating a sequence one or more times. Relative to a library, amplifying refers to en masse duplication of at least a majority of individual members of the library.

As used herein, "thiophosphate" or "phosphorothioate" are used interchangeably to refer analogues of DNA or RNA having sulphur in place of one or more of the non bridging oxygens bound to the phosphorus. Monothiophosphates or phosphoromonothioates [αS] have only one sulfur and are thus chiral around the phosphorus center. Dithiophosphates are substituted at both oxygens and are thus achiral. Phosphoromonothioate nucleotides are commercially available or can be synthesized by several different methods known in the art. Chemistry for synthesis of the phosphorodithioates has been developed by one of the present inventors as set forth in U.S. Pat. No. 5,218,088 (issued to Gorenstein, D. G. and Farschtschi, N., Jun. 8, 1993 for a Process for Preparing Dithiophosphate Oligonucleotide Analogs via Nucleoside Thiophosphoramidite Intermediates), relevant portions incorporated herein by reference.

As used herein, the terms "thio-modified aptamer" and "thioaptamer" are used interchangeably to describe oligonucleotides (ODNs) (or libraries of thioaptamers) in which one or more of the four constituent nucleotide bases of an oligonucleotide are analogues or esters of nucleotides that normally form the DNA or RNA backbones and wherein such modification confers increased nuclease resistance. For example, the modified nucleotide aptamer can include one or more phosphorothioate or phosphordithioate linkages selected from dATP($\alpha$S), dTTP($\alpha$S), dCTP($\alpha$S) and dGTP ($\alpha$S), dATP($\alpha S_2$), dTTP($\alpha S_2$), dCTP($\alpha S_2$) and dGTP($\alpha S_2$). In another example, no more than three adjacent phosphate sites of the modified nucleotide aptamer are replaced with phosphorothioate groups. In yet another example, at least a portion of non-adjacent dA, dC, dG, or dT phosphate sites of the modified nucleotide aptamer are replaced with phosphorothioate groups. In another example of a thioaptamer, all of the non-adjacent dA, dC, dG, or dT phosphate sites of the modified nucleotide aptamer are replaced with phosphorothioate groups; all of the non-adjacent dA, dC, dG, and dT phosphate sites of the modified nucleotide aptamer are replaced with phosphorothioate groups; or substantially all non-adjacent phosphate sites of the modified nucleotide aptamer are replaced with phosphorothioate groups. In still another embodiment of the present invention, no more than three adjacent phosphate sites of the modified nucleotide aptamer are replaced with phosphorodithioate groups. The thioaptamers may be obtained by adding bases enzymatically using a mix of four nucleotides, wherein one or more of the nucleotides is a mix of unmodified and thiophosphate-modified nucleotides, to form a partially thiophosphate-modified thioaptamer library. In another example of "thioaptamers" these are made by adding bases to an oligonucleotide wherein a portion of the phosphate groups are thiophosphate-modified nucleotides, and where no more than three of the four different nucleotides are substituted on the 5'-phosphate positions by 5'-thiophosphates in each synthesized oligonucleotide are thiophosphate-modified nucleotides.

Thiophosphate nucleotides are an example of modified nucleotides. "Phosphodiester oligonucleotide" means a chemically normal (unmodified) RNA or DNA oligonucleotide. Amplifying "enzymatically" refers to duplication of the oligonucleotide using a nucleotide polymerase enzyme such as DNA or RNA polymerase. Where amplification employs repetitive cycles of duplication such as using the "polymerase chain reaction", the polymerase may be, e.g., a heat stable polymerase, e.g., of *Thermus aquaticus* or other such polymerases, whether heat stable or not.

"Contacting" in the context of target selection means incubating a oligonucleotide library with target molecules. "Target molecule" means any molecule to which specific aptamer selection is desired. "Essentially homologous" means containing at least either the identified sequence or the identified sequence with one nucleotide substitution. "Isolating" in the context of target selection means separation of oligonucleotide/target complexes, preferably DNA/protein complexes, under conditions in which weak binding oligonucleotides are eliminated.

By "split synthesis" it is meant that each unique member of the combinatorial library is attached to a separate support bead on a two (or more) column DNA synthesizer, a different thiophosphoramidite or phosphoramidite is first added onto both identical supports (at the appropriate sequence position) on each column. After the normal cycle of oxidation (or sulfurization) and blocking (which introduces the phosphate, monothiophosphate or dithiophosphate linkage at this position), the support beads are removed from the columns, mixed together and the mixture reintroduced into both columns. Synthesis may proceed with further iterations of mixing or with distinct nucleotide addition.

Aptamers may be defined as nucleic acid molecules that have been selected from random or unmodified oligonucleotides ("ODN") libraries by their ability to bind to specific targets or "ligands." An iterative process of in vitro selection may be used to enrich the library for species with high affinity to the target. The iterative process involves repetitive cycles of incubation of the library with a desired target, separation of free oligonucleotides from those bound to the target and amplification of the bound ODN subset using the polymerase chain reaction ("PCR"). The penultimate result is a sub-population of sequences having high affinity for the target. The sub-population may then be subcloned to sample and preserve the selected DNA sequences. These "lead compounds" are studied in further detail to elucidate the mechanism of interaction with the target.

Dosage forms. A dosage unit for use of the aptamers and partially thioaptamers of the present invention, may be a single compound or mixtures thereof with other compounds, e.g., a potentiator. The compounds may be mixed together, form ionic or even covalent bonds. The aptamers and partially thioaptamers of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the aptamers and partially thioaptamers of the present invention to a patient in need of therapy that includes the aptamers and partially thioaptamers. The aptamers and partially thioaptamers may also be administered as any one of known salt forms.

Aptamers and partially thioaptamers is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the aptamers and partially thioaptamers may be formulated to provide, e.g., maximum and/or consistent dosing for the particular form for oral, rectal, topical, intravenous injection or parenteral administration. While the aptamers and partially thioaptamers may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions incorporated herein by reference.

For example, the aptamers and partially thioaptamers may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

The aptamers and partially thioaptamers may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The aptamers and partially thioaptamers may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the aptamers and partially thioaptamers may be coupled one or more biodegradable polymers to achieve controlled release of the aptamers and partially thioaptamers, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the aptamers and partially thioaptamers and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions or even for delivery via a suppository. Solutions for parenteral administration include generally, a water soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

Intranasal and Nasal. For direct delivery to the nasal passages, sinuses, mouth, throat, esophagous, tachea, lungs and alveoli, the aptamers and partially thioaptamers may also be delivered as an intranasal form via use of a suitable intranasal vehicle. For dermal and transdermal delivery, the aptamers and partially thioaptamers may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of aptamers and partially thioaptamers may include the following forms.

Capsules. Capsules may be prepared by filling standard two-piece hard gelatin capsules each with 10 to 500 milligrams of powdered active ingredient, 5 to 150 milligrams of lactose, 5 to 50 milligrams of cellulose and 6 milligrams magnesium stearate.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

Effervescent tablets. To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration. Parenteral and intravenous forms may also include minerals and other materials to make them compatible with the type of injection or delivery system chosen.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Mini-tabs. For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

Kits. The present invention also includes pharmaceutical kits useful, for example, for the treatment of pathogenic infection or even a cancer. The kit will generally include one or more containers containing a pharmaceutical composition with a therapeutically effective amount of the aptamers and/or partially thioaptamers disclosed herein. Such kits may further include, one or more of various conventional pharmaceutical kit components, e.g., containers with one or more pharmaceutically acceptable diluents, as will be readily apparent to those skilled in the art. Printed instructions, either as inserts or as labels, indicating quantities of the components to be administered, guidelines for mixture and/or administration, may also be included in the kit.

The aptamers and partially thioaptamers and, optionally, one or more potentiators may be mixed with a pharmaceutically acceptable carrier. The carrier may be a solid or liquid and the type is generally chosen based on the type of administration being used. The active agent may be coadministered in the form of a tablet, capsule, liposome, as an agglomerated powder, in a liquid form or as a suppository.

Vaccines. The present invention includes vaccines for both active and passive immunization. Immunogenic compositions, suitable for use as a vaccine, include the modified thioaptamers of the present invention. The thioaptamers are prepared in a manner disclosed herein. The vaccines disclosed herein are not the antigenic material, that is, they are not intended to cause an immune response, but rather, are include either alone or in combination with an antigen to "drive" or modify an immune response by altering the activity of nuclear binding proteins, including, e.g.: NF-ATs, AP-1s, NF-IL6, NF-κB, HIV reverse transcriptase, Venezuelan Equine Encephalitis nucleocapsid (using an RNA thioaptamer), HepC IRES nucleic acid, protein(s) involved in CpG-induced "innate immunity," and the like. As known to those in the immunological arts, the type of immunity, e.g., innate and/or adaptive, that is activated (or deactivated) is a critical step in the immune response. As such, the thioaptamers may be under some circumstances acting as an adjuvant but in others will actually be a direct participant in the immune response alone, that is, without addition of an antigen. The thioaptamers may even be used to prime the immune system prior a challenge.

In operation, the thioaptamer will generally be extensively dialyzed to remove undesired small molecular weight molecules and/or lyophilized for more ready formulation into a desired vehicle. The preparation of vaccines that include normal antigens are generally well understood in the art, as exemplified by U.S. Pat. Nos. 4,608,251; 4,601,903; 4,599,231; 4,599,230; 4,596,792; and 4,578,770, relevant portions of these incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

In vaccine form the thioaptamer may be administered, e.g., parenterally, by injection, for example, either subcutaneously, intraperitoneally, intranasally or into the lungs or even intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, or even 1-2%. Oral formulations include such normally employed excipients as, for example, pharmaceutical grades of mannitol, lactose, starch, magnesium stearate, sodium saccharine, cellulose, magnesium carbonate, mixtures thereof and the like. These compositions take the form of solutions, suspensions, tablets, pills, capsules, sustained release formulations or powders and contain 10-95% of active ingredient, preferably 25-70%.

The thioaptamers may be administered directly to the aerodigestive system (the pulmonary system and/or digestive tract) of a patient by an inhaled aerosol. Delivery of drugs or other active ingredients directly to a patient's lungs provides numerous advantages including: providing an extensive surface area for drug absorption; direct delivery of therapeutic agents to the disease site in the case of regional drug therapy; reducing the possibility of drug degradation in the patient's intestinal tract (a risk associated with oral administration); and eliminating the need for repeated subcutaneous injections. Furthermore, delivery of the thioaptamers to the pulmonary system via aerosol inhalation may be used to deliver drugs systemically, as well as for targeted local drug delivery for treatment of respiratory ailments such as pathogenic infections (viral, bacterial and fungal) or even lung cancer or asthma. Aerosol devices for use with the present invention in the clinical context include metered dose inhalers, dry powder inhalers, nebulizers and the like.

The thioaptamers may be formulated into the vaccine as neutral or salt forms. Pharmaceutically acceptable salts include those that are formed with inorganic acid, e.g., sodium, potassium, ammonium, calcium, or ferric hydroxides, and such organic bases as isopropylamine, trimethylamine, 2-ethylamino ethanol, histidine, procaine, mixtures thereof and the like. The vaccines are administered in a manner compatible with the dosage formulation, and in such amount as will be therapeutically effective. The quantity to be administered depends on the subject to be treated, including, e.g., the capacity of the individual's immune system to activate an innate immune response, synthesize antibodies or mount an effective cytotoxic T cell response, and the degree of protection desired. Precise amounts of active ingredient required to be administered depend on the judgment of the practitioner, however, suitable dosage ranges are of the order of a few to several hundred micrograms active ingredient per vaccination. Suitable regimes for initial administration and booster shots are also variable, but are typified by an initial administration followed by subsequent inoculations or other administrations. The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving an additional or complementary adjuvant effect for the thioaptamer may include, e.g., aluminum hydroxide or phosphate (alum), commonly used as 0.05 to 0.1 percent solution in phosphate buffered saline, admixture with synthetic polymers of sugars (Carbopol) used as 0.25 percent solution. When provided with a antigenic protein, the thioaptamer may be aggregated with the antigen and other components of the vaccine by heat treatment with temperatures ranging between 70° to 101° C. for 30 second to 2 minute periods. Examples of aggregation include reactivating with pepsin treated (Fab) antibodies to albumin, mixture with bacterial cells such as C. parvum or endotoxins or lipopolysaccharide components of gramnegative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

The thioaptamers may be used as part of a vaccine to regulate the development of Th1 or Th2 subsets in a subject or patient. In addition to in vivo modulation, the thioaptamers may be used ex vivo to modify cells in vitro that are then administered to the subject. More particularly, the thioaptamers disclosed herein may be used to modulate the activity of a transcription factor (e.g., AP-1, NF-κB or NF-AT family members) that regulate innate or adaptive immune responses. In one example the thioaptamer modulates the development of Th1 or Th2 cells in the subject is modulated.

The thioaptamer vaccine may include more that one thioaptamer in order to modulate the activity of additional transcription factors that contribute to regulating the expression of Th1- or Th2-associated cytokines. In one embodiment, a stimulatory method includes a first thioaptamer that modulated the activity of an AP-1 protein and a second agent that modulates the activity of an NF-AT protein. The second agent may be a thioaptamer or even an antigen.

The thioaptamer and the methods disclosed herein may be used to manipulate Th1:Th2 ratios in a variety of clinical situations. For example, a thioaptamer may be provided that inhibits Th2 activation, which may be useful in allergic diseases, malignancies and infectious diseases. Conversely, the thioaptamer may be used to enhance Th2 activation for treatment of autoimmune diseases and/or to improve organ transplantation.

The present inventors recognized that it is not possible to simply replace thiophosphates in a sequence that was selected for binding with a normal phosphate ester backbone oligonucleotide. Simple substitution was not practicable because the thiophosphates can significantly decrease (or increase) the specificity and/or affinity of the selected ligand for the target. It was also recognized that thiosubstitution leads to a dramatic change in the structure of the aptamer and hence alters its overall binding affinity. The sequences that were thioselected according to the present methodology, using as examples of DNA binding proteins AP-1, NF-IL6 and NF-κB, were different from those obtained by normal phosphate ester combinatorial selection.

The present invention takes advantage of the "stickiness" of thio- and dithio-phosphate ODN agents to enhance the affinity and specificity to a target molecule. In a significant improvement over existing technology, the method of selection concurrently controls and optimizes the total number of thiolated phosphates to decrease non-specific binding to non-target proteins and to enhance only the specific favorable interactions with the target. The present invention permits control over phosphates that are to be thio-substituted in a specific DNA sequence, thereby permitting the selective development of aptamers that have the combined attributes of affinity, specificity and nuclease resistance.

In one embodiment of the present invention, a method of post-selection aptamer modification is provided in which the therapeutic potential of the aptamer is improved by selective substitution of modified nucleotides into the aptamer oligonucleotide sequence. An isolated and purified target binding aptamer is identified and the nucleotide base sequence determined Modified achiral nucleotides are substituted for one or more selected nucleotides in the sequence. In one embodiment, the substitution is obtained by chemical synthesis using dithiophosphate nucleotides. The resulting aptamers have the same nucleotide base sequence as the original aptamer but, by virtue of the inclusion of modified nucleotides into selected locations in the sequences, improved nuclease resistance and affinity is obtained.

RNA and DNA oligonucleotides (ODNs) can act as "aptamers," (i.e., as direct in vivo inhibitors selected from combinatorial libraries) for a number of proteins, including viral proteins such as HIV RT (Burke et al., 1996; Chen & Gold, 1994; Green et al., 1995; Schneider et al., 1995) and transcription factors such as human NF-κB (Bielinska et al., 1990; Lebruska & Maher, 1999; Lin et al., 1998; Morishita et al., 1997; Sharma et al., 1996). Decoy ODNs were developed to inhibit expression from CRE and AP-1 directed transcription in vivo and inhibit growth of cancer cells in vitro and in vivo (Park et al., 1999). These studies and others (Boccaccio et al., 1998; Cho-Chung, 1998; Eleouet et al., 1998; Jin & Howe, 1997; Mann, 1998; Morishita et al., 1995; Morishita et al., 1998; Osborne et al., 1997; Tomita et al., 1997) have demonstrated the potential of using specific decoy and aptamer ODNs to bind to various proteins, serve as therapeutic or diagnostic reagents, and to dissect the specific role of particular transcription factors in regulating the expression of various genes. In contrast to antisense agents, duplex aptamers appear to exhibit few if any non-specific effects.

Among a large variety of modifications, S-ODN and $S_2$-ODN render the agents more nuclease resistant. The first antisense therapeutic drug uses a modified S-ODN (CIBA Vision, A Novartis Company). The $S_2$-ODNs also show significant promise, however, the effect of substitution of more nuclease-resistant thiophosphates cannot be predicted, since the sulfur substitution can lead to significantly decreased (or increased) binding to a specific protein (Milligan, J. F. and Uhlenbeck, O. C. (1989) and King et al., 2002 as well as structural perturbations (Volk et al., 2002) and thus it is not possible to predict the effect of backbone substitution on a combinatorially selected aptamer. Hence, the present inventors recognized that selection should be carried out simultaneously for both phosphate ester backbone substitution and base sequence.

Phosphorodithioate analogs have been synthesized to produce an important class of sulfur-containing oligonucleotides, the dithiophosphate $S_2$-ODNs. These dithioates include an internucleotide phosphodiester group with sulfur substituted for both nonlinking phosphoryl oxygens, so they are both isosteric and isopolar with the normal phosphodiester link, and are also highly nuclease resistant. One group showed highly effective protection of the dithioate against degradation by endogenous nucleases after 58% backbone modification. Significantly, the $S_2$-ODNs, in contrast to the phosphoramidite-synthesized monothiophosphate (S-ODNs), are achiral about the dithiophosphate center, so problems associated with diastereomeric mixtures (Lebedev & Wickstrom, 1996) are completely avoided. The $S_2$-ODNs and the S-ODNs, are taken up efficiently by cells, especially if encapsulated in liposomes.

Thiophosphate aptamers or thioaptamers are capable of specifically and non-specifically binding to proteins. Importantly, it has been observed by the present inventors that sulfurization of the phosphoryl oxygens of oligonucleotides often leads to their enhanced binding to numerous proteins (Gorenstein, 1994). The dithioate agents, for instance, appear to inhibit viral polymerases at much lower concentrations than do the monothiophosphates, which in turn are better than the normal phosphates, with $K_d$'s for single strand aptamers in the nM to sub-nM range for HIV-1 RT (Marshall & Caruthers, 1993) and NF-κB (Yang et al., 2002, King et al. 2002). For HIV-1 RT, dithioates bind 28-600 times more tightly than the normal aptamer oligonucleotide or the S-analogue. Sequence is also important, as demonstrated by the observation that a 14-nt dithioate based on the 3' terminal end of human tRNA$^{Lys}$ (CTGTTCGGGCGCCA) (SEQ ID NO.: 10) complementary to the HIV primer binding site is a more effective inhibitor ($ID_{50}$=4.3 nM) than simply dithioate $dC_{14}$ ($ID_{50}$=62 nM) by an order of magnitude (Marshall & Caruthers, 1993).

Oligonucleotides with high monothio- or dithiophosphate backbone substitutions appear to be "stickier" towards proteins than normal phosphate esters, an effect often attributed to "non-specific interactions." One explanation for the higher affinity of the thiosubstituted DNAs is the poor cation coordination of the polyanionic backbone (Cho et al., 1993, Volk et al., 2002) sulfur, being a soft anion, does not coordinate as well to hard cations like Na$^+$, unlike the hard phosphate oxyanion. The thiosubstituted phosphate esters then act as "bare" anions, and since energy is not required to strip the cations from the backbone, these agents appear to bind even more tightly to proteins.

Even in specific protein-nucleic acid contacts, sulfurization of the internucleotide linkages can lead to enhanced binding (Marshall & Caruthers, 1993; Milligan & Uhlenbeck, 1989) (or to decreased affinity). The enhanced binding is very important, since most of the direct contacts between DNA-binding proteins and their binding sites are to the phosphate groups (Otwinowski et al., 1988) (Chen et al., 1998; Ghosh et al., 1995; Muller et al., 1995). The present invention takes advantage of this chemical "stickiness" to enhance the specificity and affinity of thio- and dithiophosphate agents for a protein target. It was necessary, however, to optimize the total number of thioated phosphates to decrease non-specific binding to non-target proteins and thus enhance only the specific favorable interactions with the target protein. Also, thiosubstitution can also perturb the structure of the duplex (Cho et al., 1993) (Volk et al, 2002) although monothiophosphates substituted in the DNA strand of DNA/RNA hybrids do not appear to have dramatically altered duplex structures (Bachelin et al., 1998; Gonzalez et al., 1995). The present invention uses sequence-based, structure-based and combinatorial methods to identify both sequences and thiophosphate substitution patterns to develop thioaptamers that retained the highest specificity and affinity in binding to target proteins. The use of partial thiophosphate substitution resulted in aptamer that were more stable in vivo.

In vitro combinatorial selection of thiophosphate aptamers may be used with the present invention. A recent advance in combinatorial chemistry has been the ability to construct and screen large random sequence nucleic acid libraries for affinity to proteins or other targets (Ekland et al., 1995; Gold et al., 1997; Tian et al., 1995). The aptamer nucleic acid libraries are usually selected by incubating the target (protein, nucleic acid or small molecule) with the library and then separating the non-binding species from the bound. The bound fractions may then be amplified using the polymerase chain reaction (PCR) and subsequently reincubated with the target in a second round of screening. These iterations are repeated until the library is enhanced for sequences with high affinity for the target. However, agents selected from combinatorial RNA and DNA libraries have previously always had normal phosphate ester backbones, and so would generally be unsuitable as drugs or diagnostics agents that are exposed to serum or cell supernatants because of their nuclease susceptibility. The effect of substitution of nuclease-resistant thiophosphates cannot be predicted, since the sulfur substitution can lead to significantly decreased (or increased) binding to a specific protein (Milligan & Uhlenbeck, 1989).

The present invention have described the combinatorial selection of phosphorothioate oligonucleotide aptamers from random or high-sequence-diversity libraries, based on tight binding to the target (e.g. a protein or nucleic acid) of interest, relevant portions of which are incorporated herein by reference. An in vitro selection approach for RNA thioaptamers has also been described Ellington and coworkers (Jhaveri et al., 1998).

One approach used by the inventors is a hybrid monothiophosphate backbone. Competition assay for binding CK-1 42-mer aptamers were conducted. In standard competitive binding assays, $^{32}$P-IgkB promoter element ODN duplex was incubated with recombinant p50 or p65 and competitor oligonucleotide. The reactions were then run on a nondenaturing polyacrylamide gel, and the amount of radioactivity bound to protein and shifted in the gel was quantitated by direct counting.

A combinatorial library was created by PCR, using an appropriate dNTP(αS) in the Taq polymerization step. A combinatorial thiophosphate duplex and single stranded (ss) libraries was screened successfully for binding to a number of different protein and nucleic acid targets, including NF-IL6, NF-κB, HIV reverse transcriptase, Venezuelan Equine Encephalitis nucleocapsid (using an RNA thioaptamer), HepC IRES nucleic acid, and others, including a protein involved in CpG-induced "innate immunity." Briefly, a filter binding method was used that was modified to minimize non-specific binding of the S-ODNs to the nitrocellulose filters. A column method may also be used in which the target is covalently attached to a column support for separation as well. The duplex, ssDNA and/or ssRNA S-ODN's are eluted from the filter under high salt and protein denaturing conditions. Subsequent ethanol precipitation and for the duplex DNA S-ODNs, another Taq polymerase PCR thiophosphate amplification provided product pools for additional rounds of selection (for RNA thioaptamers RT and T7 polymerase were used). To increase the binding stringency of the remaining pool of S-ODNs in the library and select higher-affinity members, the KCl concentration was increased and the amount of protein in subsequent rounds was reduced as the iteration number increased. After cloning, the remaining members of the library were sequenced, which allowed for "Thioselect"™ simultaneously for both higher affinity and more nuclease-resistant, "Thioaptamer"™ agents. The thioselect method has been used to isolate a tight-binding thioaptamer for 7 of 7 targets tested.

NF-κB thioaptamers were created using thioselect for both in vitro thioselection as well as rational design of thioaptamers against NF-κB (Gorenstein et al., 1999a,b; 2001, 2002; King et al., 2002). Sharma, et al. demonstrated previously effective aptamer inhibition of NF-κB activity.

They further achieved inhibition of NF-κB in cell culture using S-ODN duplex decoys with NF-κB binding consensus-like sequence (GGGGACTTCC). The present inventors used the "CK-1" 42-mer duplex oligonucleotide identified by Sharma et al. (note: both the present inventors and Sharma et al.'s S-ODN duplex was chemically synthesized by sulfur oxidation with phosphoramidite chemistry and thus contains in principle $2^{82}$ or $10^{24}$ different stereoisomers!). The wild-type CK-1 duplex sequence contains 3 tandem repeats of a 14-mer NF-κB consensus-like sequence (5'-CCA GGA GAT TCC ACC CAG GAG ATT CCA CCC AGG AGA TTC CAC 3') (SEQ ID NO.: 11).

S-ODN CK-1 monothioate aptamers were made because it was unlikely that the phosphodiester form is appropriate for therapeutics or diagnostics because of its short half-life in cells, cell extracts and serum. The phosphorothioate and dithioate internucleoside modifications are therefore needed. Using recombinant protein homodimers of p50, p65, and c-Rel, the present inventors confirmed that the CK-1 sequence could bind to and compete for binding to p65 homodimer, but not p50/p50, in standard electrophoretic mobility shift assays (EMSA) (data not shown). In contrast to the fully substituted phosphorothioate, the CK-1 aptamer inhibited p65/p65 and p50/p50 equally; confirming that S-ODNs with large numbers of phosphorothioate linkages are "sticky" and tend to bind proteins non-specifically. The present inventors also found that if the number of phosphorothioate linkages is decreased to only 2-4, specificity can be restored, but binding is not enhanced. Therefore, the original publications described only the specificity of the phosphodiester oligonucleotides and did not address the problem of altered specificity of the phosphorothioates.

Changing from purified recombinant proteins to cell culture and extracts, the situation is further complicated by the presence of the other cellular components, besides the presence of other naturally occurring NF-κB homo- and heterodimers. When the present inventors attempted to repeat the binding inhibition studies of others using cell extracts, unexpected difficulties were encountered. It was found that the diester form of the CK-1 aptamer does not compete effectively for NF-κB binding in cell extracts derived from two different cell lines: the 70Z pre-B cell line and the RAW 264.7 mouse macrophage-like line. The heterodimers in these cells either do not bind the CK-1 sequence tightly enough, or it is bound by other cellular components. Published reports describing CK-1 did not present data using cell extracts, perhaps due to similar difficulties (Sharma et al., 1996). Therefore, even sequences with good binding and specificity in the diester form, when fully thiophosphate-substituted, lose their sequence specificity. Thus, this stickiness makes the characterization of fully thioated aptamers in vitro not necessarily predictive of their activities in vivo.

TABLE 1

DNA Sequences from p50 Selection

| Group 1 Sequences (n = 16) | Number of Clones |
|---|---|
| CTG TGT TCT TGT GCC GTG TCC C (SEQ ID NO.: 12) | 6/22 |
| CTG TGT TCT TGT GTC GTG TCC C (SEQ ID NO.: 13) | 4/22 |
| CTG TGT TCT TGT GTC GTG CCC C (SEQ ID NO.: 14) | 3/22 |
| CCG TGT TCT TGT GCC GTG TCC C (SEQ ID NO.: 15) | 2/22 |
| CCG TGT TCT TGT GTC GTG TCC C (SEQ ID NO.: 16) | 1/22 |

TABLE 2

DNA Sequences from p65 Selection

| Group 1 Sequences (n = 8) | Number of Clones |
|---|---|
| CGG GGT GTT GTC CTG TGC TCT CC (SEQ ID NO.: 17) | 7/16 |
| CGG GGT GTT CTC CTG TGC TCT CC (SEQ ID NO.: 18) | 1/16 |

TABLE 2-continued

DNA Sequences from p65 Selection

| | Number of Clones |
|---|---|
| Group 2 Sequences (n = 4) | |
| CGG GGT GGT GTG GCG AGG CGG CC (SEQ ID NO.: 19) | 2/16 |
| CGG GGT GGT GCG GCG AGG CGG CC (SEQ ID NO.: 20) | 1/16 |
| CGG GGT GTG CTG CTG CGG GCG GC (SEQ ID NO.: 21) | 1/16 |
| CGG GGT GTG CTG CTG CGG GCG GC (SEQ ID NO.: 22) | 1/16 |

Thioselection against NF-κB (p50:p50, p65:p65). As described in King, et al. (2002) a unique thiophosphate duplex library was screened for binding to the p50 homodimer Thioselection was repeated through 15 rounds to enrich for sequences that bind to p50 with high affinity. DNA sequences of multiple clones were analyzed from the initial, 2nd, 6$^{th}$, 10$^{th}$ and 15$^{th}$ round libraries. A striking convergence of the DNA sequences was observed by round 15. Of the 22 clones analyzed, 16 had a highly similar sequence (Table 1). A thioaptamer representing this sequence was generated by PCR amplification using a biotinylated reverse primer. Binding studies were conducted using a chemiluminescent EMSA, which uses a biotinylated thioaptamer. The biotinylated thioaptamer binds tightly to p50; the sequences are different from those obtained for in vitro combinatorial selection against p65 homodimers (Table 2). The chemically synthesized phosphorothioate aptamers are a diastereomeric mixture of both Rp and Sp configurations. The thioaptamers bind and compete for the same NF-κB site as the known promoter element IgκB ($K_d$=78.9±1.9 nM for a Rel A-selected thioaptamer, and 19.6±1.25 nM for a p50-selected thioaptamer). The normal phosphate ester backbone version of the Rel A selected aptamer binds Rel A with a $K_d$ of 249.1±1.8 nM. The p50 dimer-selected chiral thioaptamer binds to p50 with affinities below 5 nM under conditions where no binding to p65 is observed. Similarly, the p65 dimer-selected chiral thioaptamer binds to p65 dimers with affinities below 5 nM under conditions where no binding to p50 is observed.

These EMSA binding studies demonstrated that the enhanced affinity can be attributed to the presence of sulfur. Collectively, these results further demonstrate the feasibility of the thioaptamer selection technology as a method for producing specific, high-affinity ligands to proteins. It was also demonstrated that the chemically synthesized (mixed diasteromer) thioaptamers bind tightly in cell nuclear extracts to both the p50:p65 heterodimer and p50:p50 homodimer However, the enzymatically synthesized, chiral thioaptamer selected against the p50 homodimer only binds to p50:p50 in nuclear extracts (Fennawald, et al, unpublished; King, et al., 2002; Gorenstein, patents pending, 1999 a, b, 2001). Remarkably, for the p50 homodimer the selection sequence appears to contain a pseudo-palindrome, suggesting that 2 dimers may be binding to the 22-mer sequence:

CTGTG PyT(CT)T G* T(G)TPy GTGTC CC (SEQ ID NO.: 23)

Dithiophosphate Aptamers Binding to Proteins. S$_2$-ODN CK-14 dithioate aptamers were also isolated. The CK-14 14-mer duplex was also synthesized with some strategically placed dithioate linkages (both of the non-bridging oxygens are replaced by sulfurs). As noted by the present inventors, strategic dithioate linkage ODNs have exhibit significant differences, as they have altered binding specificity, and lack the extreme "stickiness" of the fully thioated aptamer. With an increasing number of dithioate substitutions in the same sequence, binding by the S$_2$-ODN increases dramatically (data not shown). One of the tightest-binding dithioaptamer (XBY-6) contains 6 dithioate linkages on the two strands. Significantly, the XBY-6 aptamer also binds to a single NF-κB dimer in cell extracts (data not shown), while the standard phosphodiester ODN shows no NF-κB-specific binding in extracts. Thus, the present inventors succeeded in synthesizing a thioate backbone modification which for the first time increases the specific binding of the oligonucleotide to NF-κB above that to other cellular proteins (Yang et al., 1999). In standard competitive binding assays, the $^{32}$P-IgkB promoter element ODN was incubated with recombinant p65 and varying amounts of XBY decoy competitor. The relative binding ability of the unlabeled ODNs was determined by the concentration needed to compete effectively with the standard labeled ODN. XBY1 through 6 correspond to CK-14 aptamers with 1 though 6 dithiophosphate substitutions, respectively (Yang, et al., 1999).

ODN aptamer was incubated with 70Z/3 cell nuclear extract in the presence or absence of anti-p50 antibody. Protein-bound ODN duplex was separated on a standard gel. XBY-6 shifts one complex in nuclear extracts from a 70Z/3 pre-B cell line. By using specific antibodies to supershift the complex, p50 was identified as one component of the complex, which may be a complex that include a p50 or p105 dimer, or a p50 (or p105)-containing heterodimer. Since XBY-6 binds more tightly to p50/p50 than p65/p65, the shifted band is likely to represent the p50 homodimer. The band did not co-migrate with either the p50/p50 or p50/p65 bands, but the change in the altered chemical structure changes the mobility of the ODN. Only one major band is seen, however, even though the lysate contains at least two major distinguishable NF-κB complexes (p50 homodimers and p50/p65 heterodimers).

These results demonstrate the use of aptamers having altered binding specificity and affinity by substituting only a limited number of internucleoside linkages, that is, a portion of the internucleoside linkages. The partially-modified aptamer was used to distinguish among various NF-κB dimers within the cell. The IgκB standard ODN does not show such specificity. Therefore, this modified thioaptamer may be used to bind to a single NF-κB dimer within cell supernatants and even inactivate target dimers within whole cells and animals. It was also found that when guinea pigs were injected with LPS to induce inflammatory response and XBY-6, an increase in the levels of TNF-α was observed above that when the animals were injected with LPS alone. In animal macrophage extract studies, it was found that XBY-6 eliminated a single p50 (or p105) dimer band on EMSAs. Since the p50 homodimer appears to be a transcriptional inhibitor of the immune response, these data demonstrate the ability to target a single protein within live animals, and the feasibility of altering the binding specificity by substituting only a limited number of internucleoside linkages (Gorenstein, et al. patents pending, 1999 a, b; 2001, 2002). Using the modified thioaptamer a 1:1 binding stoichiometry of p65 to the 22mer binding site known as IgκB with a $K_d$ near 4 nM. For one dithiophosphate aptamer, XBY-6, a binding affinity to p65 homodimer of 1.4 nM vs. sub-nM to p50 was demonstrated.

Various thioaptamers have been made and isolated using the present invention that can distinguish among various NF-κB dimers within the cell. One of these decoys was able to bind to a single NF-κB dimer in cell extracts or within a cell in either cell culture or animal studies. These results point to the importance of using modified thiophosphate combinatorial selection methods to identify minimally substituted thioated oligonucleotides with high affinity, high binding specificity and increased nuclease resistance in vitro and in vivo.

Phosphorodithioate and phosphorothioate aptamers via split synthesis combinatorial selection. The identification of specific S-ODN and $S_2$-ODN thioaptamers that bind proteins based upon in vitro combinatorial selection methods is limited to substrates only accepted by polymerases required for reamplification of selected libraries by the polymerase chain reaction (PCR). Another disadvantage of using the polymerization of substituted nucleoside 5'-triphosphates into ODN aptamers are the restrictions on the choice of P-chirality by the enzymatic stereospecificity. For example, it is known that [$S_p$]-diastereoisomers of dNTP(αS) in Taq-catalyzed polymerization solely yield [Rp]-phosphorothioate stereoisomers (Eckstein, 1985). Therefore, using current methods it is not possible to select [Sp]-phosphorothioate stereoisomers along with achiral $S_2$-ODN analogous since both [Rp]-diastereoisomers of dNTP(αS) and nucleoside dNTP(α$S_2$) are not substrates of polymerases. Additionally, these in vitro combinatorial selection methods require many iterative cycles of selection and reamplification of the bound remaining members of the library by the PCR, which are quite time consuming, although automation of this in vitro selection is possible.

What is needed are methods that permit the isolation of, e.g., individual aptamer:protein complexes without the need for repeated iterative cycles of selection and reamplification of likely binding targets. Also needed are systems that permit the creation, isolation, sequencing and characterization of making [Sp]-phosphorothioate stereoisomers along with achiral $S_2$-ODN analogs. To overcome these limitations of the in vitro combinatorial selection methods, the present inventors developed a one-bead, one-compound library made by using a split synthesis method to create an alternative to in vitro combinatorial selection methods. One-bead library systems have been used for organic molecules (Felder, (1999)), peptides (Lam, et al., 1991, 1995; Lam, 1995), and oligosaccharide libraries (Zhu and Boom, 1998; Liang, et al., 1996; Hilaire and Meldal, 2000). A one-bead one-oligonucleotide (one-ODN) (e.g., O-ODN, S-ODN, $S_2$-ODN, both DNA or RNA) may be used in conjunction with combinatorial library selection methodology used to identifying a specific oligonucleotide aptamer that binds to specific proteins or other molecules (Yang, et al., 2002; Gorenstein, et al., U.S. patent applied).

Furthermore, the method may use $S_2$-ODN reagents with sulfurs replacing both of the non-bridging phosphate oxygens that are isosteric and isopolar with the normal phosphorodiester and are particularly advantageous for binding and screening. Importantly, $S_2$-ODNs are achiral about the dithiophosphate center, which eliminated problems associated with diastereomeric mixtures generally obtained for the chemically synthesized S-ODN. The split synthesis approach disclosed herein has been used for the construction of O-ODN, S-ODN, $S_2$-ODN and RNA bead-based aptamer and thioaptamer libraries (Gorenstein et al, US patents pending, 1999 a, b, 2001, 2002; awarded, 2002; Yang et al., 2002). In this procedure each unique member of the combinatorial library is attached to a separate support bead. Targets that bind tightly to only a few of the $10^4$-$10^8$ different support beads can be selected by binding the target protein to the beads and then identifying which beads have bound target by immunostaining techniques or direct staining of the target or SELDI MS (see below). The present methodology permits rapid screening and identification of modified thioaptamers that bind to proteins such as NF-κB using a novel PCR-based identification tag of the selected bead.

To introduce many copies of a single, chemically pure S-ODN thioaptamer onto each bead, a "mix and separate" split synthesis method was used. A two-column DNA synthesizer was used simultaneously for construction of the library. The normal phosphate backbone linkages were carried out using standard phosphoramidite monomers via oxidation in column 1, while the phosphorothioate linkages were carried out using standard phosphoramidite monomers via sulfurization in column 2 Dithioate are introduced by using thiophosphoramites with sulfur oxidation. Two sequences of the same length are programmed for each column and are designed such that the bases are different at every equal position not only for diversifying base compositions but also for coding a phosphate, phosphoromonothioate/dithioate.

For example, on an Expedite 8909 DNA synthesizer with dual columns, onto column 1 a phosphoramidite (for example: C) is coupled to the bead and after completion of oxidation, the resulting product is nucleotide (C) with a phosphotriester linkage. On column 2 a nucleoside phosphorothioate is introduced with a different base (T for example). The two columns are mixed and resplit and in the second cycle, additional phosphoramidites or phosphorothioamidites are introduced, followed by oxidation and sulfurization reactions individually in column 1 and column 2. After additional coupling steps and after split/pool synthesis is carried out, the end products comprise a combinatorial library of thioaptamers with varying monothioate, dithioate or normal phosphate ester linkages at varying positions along the ODN strand. On completion of the automated synthesis, the column is removed from the synthesizer and dried with argon. The bead bound fully protected ODNs are treated with 1 ml of concentrated ammonia for 1 h at room temperature, incubated in a 55° C. oven for 15-16 h, removed from the oven and cooled to room temperature. Importantly, after deprotection, with this coupling scheme with a non-cleavable hexaethyleneglycol linkers. Linker attaching the first phosphoramidite (15 or 70 μm beads provided by ChemGenes), the thioaptamers are still covalently attached to the beads after complete deprotection. Thus, each bead contains a single sequence with a specified backbone modification that is identified by the base.

For example, this scheme was used to synthesize libraries of 4096 (212) different thioaptamers attached to beads, each bead containing a unique thioaptamer. This library consisted of a 22-nucleotide "random" sequence (12 split/pool steps) flanked by 15 nucleotide defined primer regions at the 5' and 3' ends (Yang, et al., 2002). A phosphorothioate linkage was introduced on every other base in column 2, following the "split and pool" approach. The single-stranded 52-mer S-ODN random library was converted to double-stranded DNA by Klenow DNA polymerase I (Promega) reaction in the presence of DNA polymerase buffer, dNTP mix and downstream primer. Therefore, the one strand of the duplex potentially contained S-ODN modifications and the other complementary strand were composed of ODN. A duplex DNA library in which both strands contain S-ODN modifications could also be generated using a Klenow reaction with no more than three dNTP (α)S.

The dsDNA thioaptamer library beads were screened for the ability to bind the NF-κB p50/p50 dimer labeled with the Alexa Fluor 488 dye (Molecular Probes). After initial binding of protein, the beads were thoroughly washed with PBS with 0.1% Tween 20 to minimize nonspecific binding. Typically, a few positive beads were intensely stained when viewed by fluorescence, while the majority of the beads remained unstained as (data not shown). With the aid of a micropipette coupled to a micromanipulator, the intensely stained beads were retrieved. Only highly positive beads from several thousand were found using this method. As described below, multicolor flow cytometry and cell/bead sorting was used to automate the selection process to select the tightest binding thioaptamer-protein complexes.

Sequencing may also be obtained directly from the bead. Each individually selected bead was washed thoroughly with 8 M urea (pH 7.2) to remove the protein and was directly used for the "one-bead one-PCR" amplification using the 5' and 3' end primers. The PCR product was cloned using the TA Cloning procedure (Invitrogen) and sequenced on an ABI Prism 310 Genetic Analyzer (Applied Biosystems). The four thioaptamers listed in Table 3 were obtained from the library. For verification of these results, the S-ODN, 5'-CtGTGAGtCGACTgAtGaCGGt-3' (SEQ ID NO.: 7) (small letters represent location of 3'-monothiophosphates), was synthesized independently on the non-cleavable linker bead support, hybridized with its complementary ODN and then mixed again with the p50/p50 protein labeled with the Alexa Fluor 488 dye. The fluorescence intensity of all of the beads viewed under the fluorescence microscope was qualitatively similar to the intensity of the selected bead containing this sequence within the combinatorial library. These results demonstrate that the primer regions do not contribute to the binding of p50/50. Furthermore, it was found that not only normal monothio-ODN on the beads but also dithio-modified bead-bound sequences could be sequenced directly from the dithiophosphate combinatorial library. Thus, the split synthesis has been used to create a "one-bead-one sequence" ODN and that PCR can be used to identify an S-ODN bound to a bead (Yang et al., 2002; Gorenstein et al, US & Foreign Patents pending, 1999 a, b, 2001, 2002).

Bead-based thioaptamer library screen. Aliquots of S-ODN beads bound to NF-κB p50/p50 homodimer protein labeled with the Alexa Fluor 488 dye viewed under light microscopy. The same beads viewed under fluorescence microscopy, in which a positive green bead stained with Alexa Fluor 488 dye were easily identified in a background of many hundreds of nonreactive beads. Single positive bead can easily be retrieved with a handheld micropipette under fluorescence microscopy.

Although the beads were screened against a target protein labeled with a fluorescent dye, the beads have also been screened directly against cell extracts as well. The binding of the NF-κB to a specific sequence can be detected using a primary anti-NF-κB antibody such as anti-P50 (Rabbit IgG antibody, Santa Cruz Biotechnology, Inc.) followed by a secondary antibody conjugated with Alexa Fluor 488 (goat anti-rabbit IgG from Molecular Probes). Beads that included the XBY-6 oligonucleotide were screened against WI-38 VA13, an SV40 virus-transformed human fibroblastic cell line extract by similar fluorescent microscopy.

Other bead-based thioaptamer libraries. Combinatorial thioaptamer bead libraries of over $10^6$ different sequences have also been readily prepared. The present inventors have synthesized successfully a monothio RNA library ($2^{15}$=32768) (Gorenstein, et al., patent pending, 2002). Thus, standard phosphoramidite (DNA and RNA) chemistry was used for the thioaptamer RNA library. A 0.5 M 1H-tetrazole in acetonitrile was used as DNA activator. A 0.5 M solution of DCI (dicyanoimidazole) in acetonitrile was used as RNA activator. The libraries were prepared on a 1 µmole scale of polystyrene beads (66-70 µm). The downstream and upstream primers, 5'-d(GGATCCGGTGGTCTG)-3' and 5'-d(CCTACTCGCGAATTC)-3' were synthesized in parallel on a two-column DNA synthesizer (Expedite 8909, Applied Biosystems). Following the 5'-primer, the sequences programmed on the synthesizer for the combinatorial mono RNA library were 5'-r(GA*UC*CU*GA*AA*CU*GU*UU*UA*AG*GU*UG*GC*CG*AU*C)-3' (SEQ ID NO.: 24) on column 1 and 5'-r(cU*aG*gA*cU*uG*gC*aC*aA*cC*gU*cA*cA*cU*gC*uA*u) -3' (SEQ ID NO.: 25) on column 2 The 3'-primer sequence completed the 61-mer programmed on the synthesizer. A "split and pool" occurred at each position indicated by an asterisk in order to synthesize the combinatorial region for the monothio RNA. The lower case letter indicates a 3'-thioate linkage, the upper case letter indicates a 3'-phosphate linkage. The coupling yield was typically upwards of 98.5% as determined by the dimethoxytrityl cation assay (DNA couplings are typically >99%/nt). Sulfurization chemistry utilized the Beaucage reagent. The fully protected monothio RNA combinatorial library with the non-cleavable linker beads were treated with 4 ml of a mixture of 3:1 (v/v) (28%) $NH_3$: EtOH at 39° C. for 21 hrs. The beads were centrifuged, the supernatant was removed and the solid support was washed with double-distilled water. After lyophilization the solid support was treated with 2 ml of triethylamine trihydrofluoride (TEA-3HF) for 20 hrs at room temperature. Again, the beads were centrifuged, the supernatant was removed and the solid support was washed with double-distilled water. RT PCR and TA cloning confirmed the successful synthesis of the ssRNA thioaptamer library.

TABLE 3

Sequences of thioaptamers selected from split synthesis (small letters indicate thiophosphate 3' to base).

| | |
|---|---|
| 5'-tGTGcAGGGACTgAtGaCGGt-3' | (SEQ ID NO.: 6) |
| 5'-CtGTGCatCGAaGTTtGCAtTt-3' | (SEQ ID NO.: 7) |
| 5'-AtGcAcAtCtCaGgAtGaCGGt-3' | (SEQ ID NO.: 8) |
| 5'-AGTTGcAGGtCaGgACCCAtTt-3' | (SEQ ID NO.: 9) |

Flow cytometry sorting of thioaptamer bead-based library. The present inventors have also demonstrated the successful application of high throughput/multi-color flow cytometry and bead sorting to screen aptamer bead libraries for those beads which bind to, e.g., a target protein (Gorenstein, et al., patent pending, 2002). Modifications were made to a custom-built flow cytometer to make it more amenable to bead identification and isolation. For example, bead fluorescence and forward scatter were the two parameters chosen for real-time characterization of each aptamer bead passing the first sort point of the custom-built flow cytometer/sorter. Other scanning and sorting parameters may be used to select, isolate, view, designate, characaterize, etc. the beads through a flow cytometer.

In operation, "positive" beads (contain thioaptamer-bound target protein, the target protein was fluorescentlabelled with Alexa 488 dye) were easily sorted from negative beads. Flow cytometry may be used to replace, e.g., visual fluorescence microscope identification of beads containing bound target protein and the need to isolate the individual "positive" beads with the micromanipulator described previously. The flow-sorted "positive" beads can then be subjected to, e.g., one-bead PCR to identify the thioaptamer that binds the target protein.

TABLE 4

Population Statistics for bead sorting, WinList analyses (all data were color-compensated)

| Sample | Total | Region | % Gate |
|---|---|---|---|
| FIG. 6A: CONTROL.FCS | | | |
| R1: Autofluorescent Beads | 10000 | 9530 | 95.3 |
| FIG. 6B. FCS | | | |
| R2: p50 Alexa 488 Positive Beads | 10000 | 35 | 0.35 |
| FIG. 6C. FCS | | | |
| R3: p65 PE Positive Beads | 20000 | 3488 | 17.44 |
| FIG. 6D. FCS | | | |
| R1: Autofl. Beads & Carrier Beads | 1000000 | 963321 | 96.33 |
| R2: p50 Alexa 488 Positive Beads | 1000000 | 354 | 0.04 |
| R3: p65 PE Positive Beads | 1000000 | 935 | 0.09 |

Fluorescence sorting was also used to demonstrate the use of the one-bead, one-ODN:protein system using dual color sorting. The IgκB dsDNA consensus sequences were immobilized onto 15-20 micron polystyrene microspheres. The DNA bound beads were then incubated with purified p50 and p65 proteins, respectively. DNA transcription factor complexes were detected with primary antibodies specific for the p50 and p65 proteins followed by an additional incubation with Alexa 488-conjugated secondary antibody for p50 and PE-conjugated secondary antibody for p65. The beads were viewed by fluorescent microscopy and then analyzed on the MCU's HiReCS system. A Control Fluorescent Cell Sort (CONTROL.FCS) shows the autofluorescent microspheres in the negative control sample where the beads were unbound. The majority of the beads in the "debris" population were the 0.8 micron carrier beads that were used to bring up the volume of the samples since the beads were at a very low dilution.

Innate Immunity Toll-Like Receptor Signaling. In another embodiment of this invention, the present inventors developed thioaptamers that enhance the innate immune response by targeting the Toll-like receptor (TLR) family in mammals, which is a family of transmembrane proteins characterized by multiple copies of leucine rich repeats in the extracellular domain and IL-1 receptor motif in the cytoplasmic domain (Akira et al., 2001; Medzhitov, 2001). The TRL family is a phylogenetically conserved mediator of innate immunity that is essential for microbial recognition. Ten human homologs of TLRs (TLR1-10) have been described. By using a BLAST search, Hemmi et al., 2000, have identified and subsequently isolated a cDNA coding for TLR9. Gene knockout experiments suggest that TRL9 acts as a receptor for unmethylated CpG dinucleotides in the bacterial DNA. Human and mouse TLR9 share an overall amino-acid identity of 75.5%. TLR9 is highly expressed in spleen (Krieg, 2002).

The immunostimulatory properties of bacterial DNA appears to be related to short six base sequences called CpG motifs that have the general structure of two 5' purines, an unmethylated CpG motif, and two 3' pyrimidines (Krieg, 2002). Though such sequences rarely appear in mammalian DNA due to CpG suppression and methylation of cytosine nucleotides, they are relatively abundant in bacterial DNA, occurring at the expected frequency (1 in 16) and in unmethylated form. Indeed, studies have found ODNs containing these sequence motifs to be strongly immunostimulatory, resulting in the activation of B cells, NK cells, and antigen-presenting cells, and in the induction of a variety of cytokines including interleukin-12 (IL-12), IL-6, and tumor necrosis factor-α. CpG ODNs have also been found to be effective as adjuvants in inducing antigen-specific T-helper-1-like responses, and have been the focus of much interest for their inclusion in anti-tumor vaccinations and use in other therapeutic applications (Klinman et al., 1999; Krieg et al, 1999). Adjuvants enhance nonspecifically the immune response to an antigen. For example, pathogenic Arenaviruses appear to block or modify immunoregulatory cell signaling pathways (Peters & Zaki, 2002, Solomon and Vaughn, 2002; Fennewald et al., 2002). Using the present invention it was possible to disrupt Arenavirus and Flavivirus cell signals that contribute to immune evasion and pathogenesis. Using thioaptamers it was demonstrated that the thio-modified aptamers of the present invention could be used to counteract viral induced cellular perturbations and protect the infected host.

Viral Strategies to manage the host. During the co-evolution of viruses and their hosts, viruses have developed ingenious strategies to counteract the host defenses that normally control viral replication and spread. Similarly, viral strategies modify the cellular environment to promote viral macromolecular synthesis and viral replication. This highly ordered interation often has the unfortunate consequence of inducing disease in the host. Viruses have evolved mechanisms to interfere with major histocompatibility complex antigen presentation, block apoptosis, disrupt complement cascades and modulate multiple cytokine networks (Lalani & McFadden, 1999; Ploegh, 1998). Viruses have targeted cell-signaling pathways involved in cytokine and chemokine signaling, the regulation of apoptosis, and the cell cycle. Studies have revealed a number of instances of direct viral intervention in the receptor and receptor proximal signaling, as well as direct interaction with signaling kinase cascades and transcription factors (McFadden et al., 1998; Ploegh, 1998; Hiscott, 2001; Hiscott et al., 2001). Most examples have come from large DNA viruses with sufficient coding capacity to encode viral homologs of cellular proteins. These viruses use molecular mimicry to exploit the cellular environment to promote viral replication and antagonize the immune response to sustain their survival in an immunocompetent host (Cameron et al., 1999; Willer et al., 1999; Hiscott et al., 2001). Influencing key transcription factors that regulate pro or anti-inflammatory cytokines is an efficient means by which viruses could cripple multiple immune responses (Powell et al., 1996; Tait et al., 2000). The strategies employed by the smaller, less genetically complex viruses are equally elegant, and often even more of an enigma.

Pichinde infection of guinea pigs is particularly suited to studies on the immunomodulation by virus infection. There are two virus variants with minimal genomic differences but profoundly different effects on the animal. Infection by the P2 variant of virus results in mild illness from which the animal recovers. Infection by the P18 variant results in death. These two virus variants were used to distinguish an effective immune response against the P2 virus, from an ineffective response against the P18 virus.

Using the aptamers of the present invention, the differential effect of virus infection was identified as including a profound effect on the transcription factors NF-κB and RBP-Jκ. Data generated by the present inventors (Fennewald et al., 2002) showed differential alterations in the transcription factors NF-κB and RBP-Jκ in P2 and P18 virus-infected guinea pig peritoneal macrophages. The P2 variant shows less NF-κB present and a higher mobility RBP-Jκ complex. This observation was used in an animal model of arenavirus disease in which two virus variants differentially affect target cell signaling pathways. NF-κB and AP-1(CREB) family members are key regulators of the immune response and transcription factors involved interferon response to virus infection all are differentially induced in pathogenic Pichinde infections. Using the aptamers of the present invention infected hosts virulence was reduced by modulating virus induced alterations in cellular signal transduction.

Figure 2:
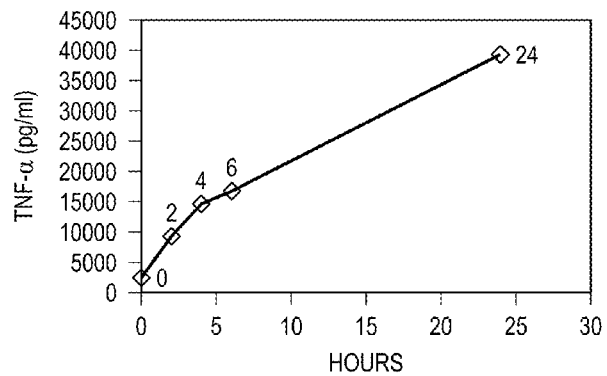
FIG. 2 is a graph that shows the production of TNF-α in P388D1 cells. Cells were treated with polyI/C (25 µg/ml) and media samples were taken at indicated times, the TNF-α levels in the media were determined using commercially available ELISA.
Figure 3A:
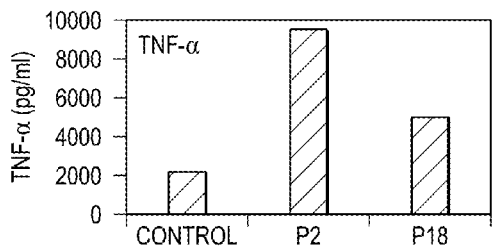
FIGS. 3A, 3B and 3C are bar graphs that show the production of by P388 cells infected with P2 or P18 taken three days post-infection and assayed for TNF-α (3A), IL-6 (3B) and IL-12 (3C)
Figure 3B:
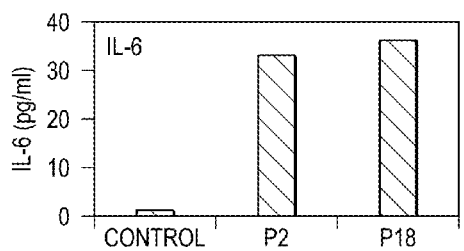
Figure 3C:
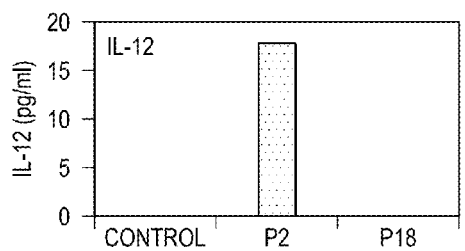

Many of the signaling pathways and transcription factors activated during immune system activation lead to the synthesis of the inflammatory cytokines. Certain pathways require the expression of various cytokines. The effect of the virus variants (and polyI/C) on the induction of cytokines was determined FIG. 2 is a graph that shows that polyI/C is an effective inducer of the proinflammatory cytokine TNF-α. Infection with P2 and P18 also alter the expression of this and other inflammatory cytokines. In particular, P2 and P18 induced equally cytokines such as IL-6; which are moderately different in their induction of TNF-α and substantially different in IL-12 induction (FIG. 3). Thus, differences in signaling and inflammatory responses are associated with immune activation by P2 virus and poor activation by the P18 virus. For example, IL-12 is especially important in directing the anti-viral immune response to the effective Th1 cytotoxic T cell response (Seow, 1998). In addition to supporting the association with the immune response, this data can be used to direct the transcription factors to target. For example, IL-6 induction is similar for both virus variants.

Figure 4:
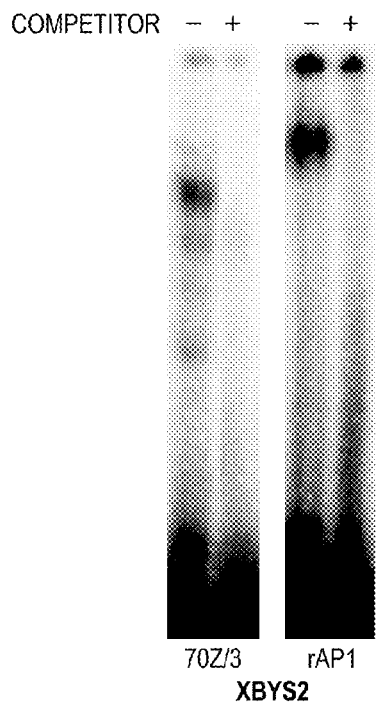
FIG. 4 is a gel that shows that the XBY-S2 aptamer binds specifically to proteins in 70Z/3 cell nuclear extracts and recombinant human AP-1.
Figure 5:
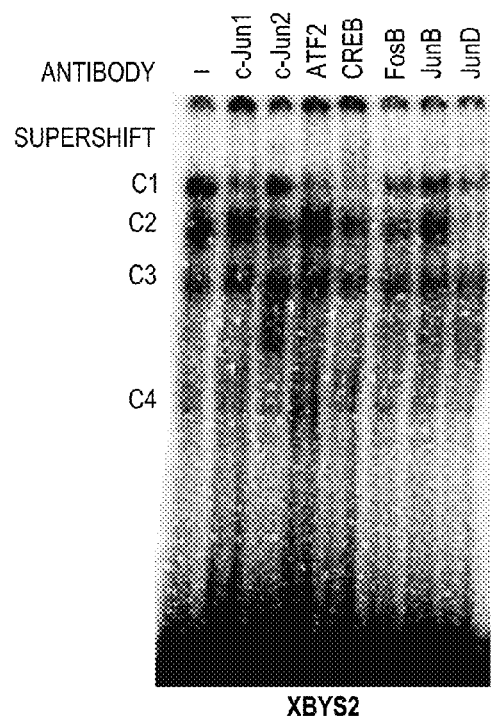
FIG. 5 is a gel that shows a supershift analysis using a variety of antibodies specific for various members of the AP-1 transcription factor family.
Figure 6:
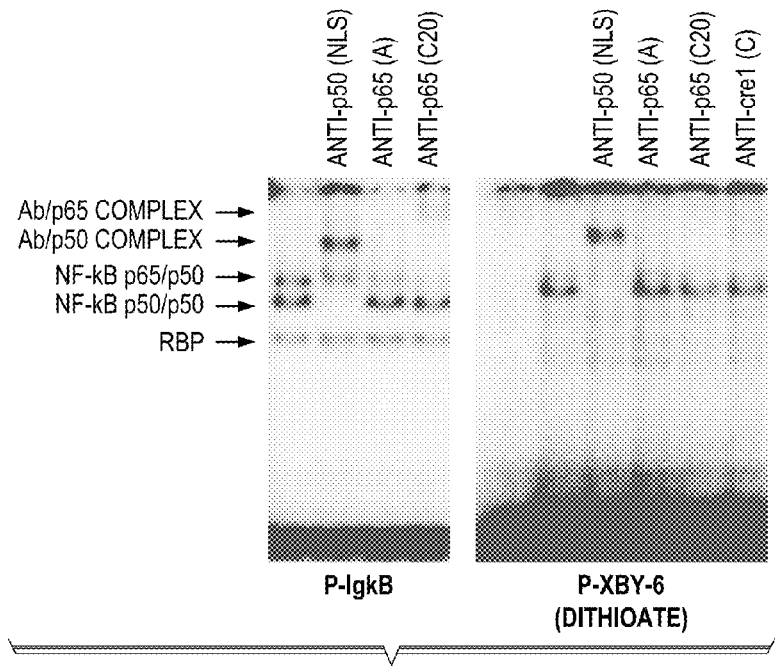
FIG. 6 is a gel with a comparison of XBY-6 and Igκ oligonucleotide binding to proteins in 70Z/3 cell nuclear extracts in which multiple NF-κB dimers are shown to bind the Igκ oligonucleotide, with specific binding of only p50 (or p105) containing dimers to XBY-6.
Figure 7:
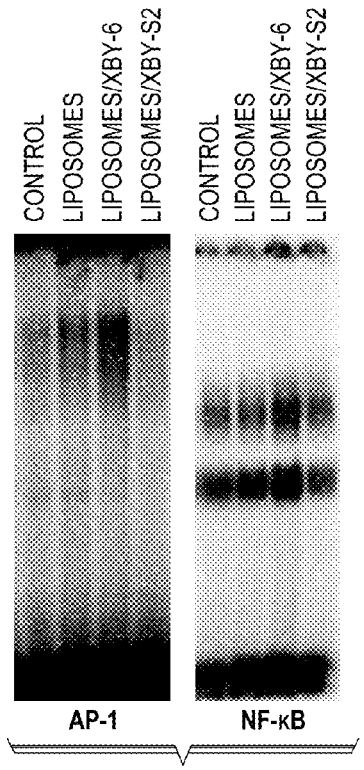
FIG. 7 is a gel that shows that XBY-S2 eliminates AP1 DNA binding activities in macrophages treated with liposomes with and without the indicated aptamers for 24 hours, wherein the nuclear extracts were analyzed by electrophoretic mobility shift assay (EMSA) with the AP-1 and NF-κB oligonucleotide probes.

To target transcription factors key in regulating TNFα and IL12 and other key mediators of the immune response two thioaptamers were produced, XBY-6 (SEQ ID NO.: 1) targeting NF-κB p50 homodimers and XBY-S2 targeting AP-1, both with six dithio residues. In FIG. 4, XBY-S2 (SEQ ID NO.: 2) is demonstrated to bind specifically to AP-1 proteins in pre-B cell nuclear extracts (70Z/3) and to human recombinant c-jun protein dimers (AP-1). In FIG. 5, supershift analyses indicate that XBY-S2 binds to several members of the AP-1 protein family including JunD, CREB and possibly ATF2, and c-Jun. The XBY-6 thioaptamer binds specifically to the NF-κB p50 (or p105) homodimer (FIG. 6). Macrophage cultures were treated with XBY-S2 and XBY-6 and nuclear extracts were produced to assay the effects of these thioaptamers on the DNA binding activities of the transcription factors to which they are targeted. In FIG. 7, macrophage cultures were treated with liposomes, and liposome containing the indicated thioaptamers overnight and nuclear extracts produced and assayed using the indicated oligonucleotides. The XBY-S2 thioaptamer efficiently eliminated transcription factor binding to the AP-1 oligonucleotide. In contrast, treatment with XBY-6 resulted in an increase in the NF-78 B DNA binding activity.

Figure 8:
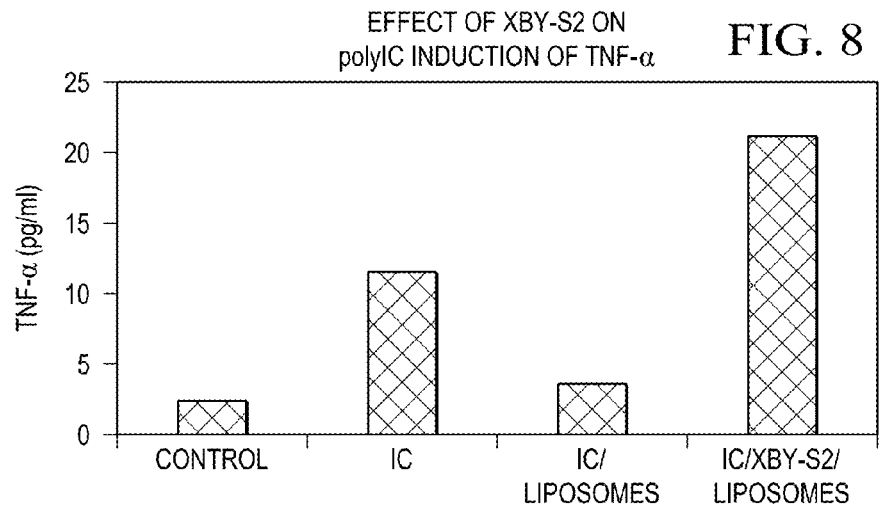
FIG. 8 is a graph that shows the secretion of TNFα as measured by ELISA of Mouse P388D1 macrophage cultures were treated with XBY-S2 for 12 hours followed by stimulation with PolyI/C and harvested at 24 hrs.
Figure 9:
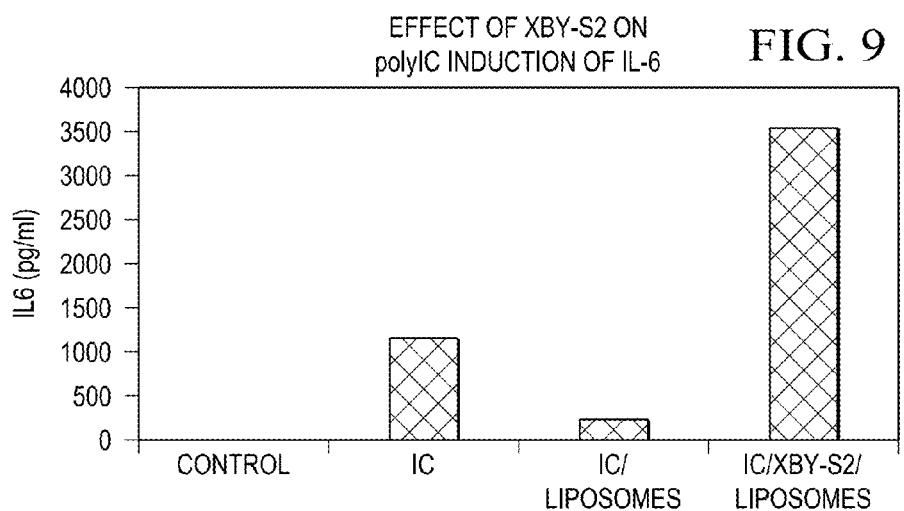
FIG. 9 is a graph of IL-6 production assayed by ELISA of mouse P388D1 macrophage cultures treated with XBY-S2 for 12 hours followed by stimulation with PolyI/C and harvested at 24 hrs.

In order to determine the consequence of the elimination of AP-1 DNA binding activity by XBY-S2, stimulated macrophage cultures were incubated with the thioaptamer with PolyI/C and measured the elaboration of TNFα and IL-6 into culture media. The expression of both TNFα and IL-6 are increased in response to polyI/C (FIGS. 8 and 9). Pretreatment of cultures with XBY-S2 thioaptamer increases the amount of both cytokines produced in response to poly I/C. These results indicate that elimination of AP-1 from cells by the XBY-S2 decoy thioaptamer increases the production of cytokines.

Figure 10:
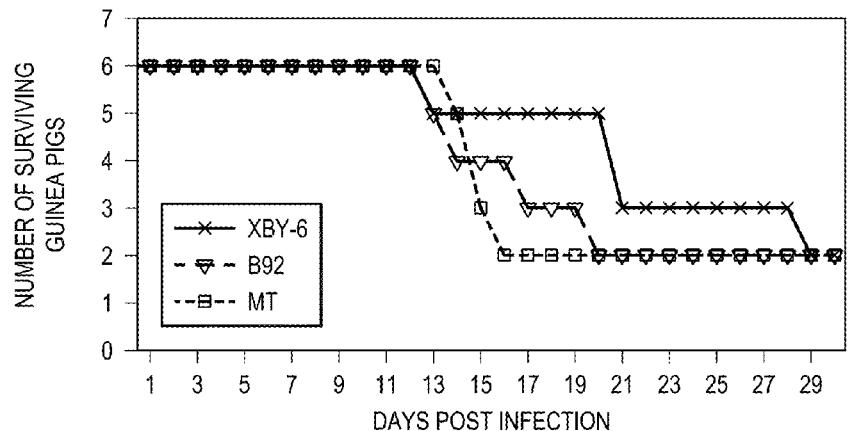
FIG. 10 is a graph that shows survival curves following Pichinde P18 infection in guinea pigs treated with the NF-κB aptamer, XBY-6, the scrambled control, B92, or vehicle, MT, of animals infected by injection of 1000 pfu of Pichinde P18 at day 0, treatment consisted of intraperitoneal injections at days 0, 1 and 2.

It has been suggested that arenaviral and West Nile pathogenesis is the result of viral perturbation of the immune response resulting in the inappropriate expression of cytokines. Therefore, modulation of cell signaling by appropriate thioaptamers could reverse the inappropriate gene expression and help to alleviate the symptoms and perhaps prevent host death. Guinea pigs were treated with the XBY-6 thioaptamer targeting NF-κB p50 homodimers at days 0, 1, and 2 day relative to time of infection with a lethal dose of Pichinde virus. FIG. 10 demonstrates that the thioaptamer prolongs the survival of Arenavirus infected animals. A thioaptamer of the same base content but scrambled in sequence and containing CpG islands did not prolong survival (B92; FIG. 10). Using the XBY-S2 thioaptamer, 50-80% protection of mice from a lethal West Nile virus infection was demonstrated (Tables 5 and 6) as well as prolongation of Pichinde virus survival similar to XBY-6 (data not shown).

TABLE 5

Female 3-4 week-old NIH Swiss mice were given aptamers at one day before and 90 minutes before administration of 10 LD$_{50}$ WN virus strain USA99b by the ip route.

| Group | # surviving [%] | AST (days ± SD) |
|---|---|---|
| PBS only | 0/5 [0] | 7.2 ± 0.4 |
| Liposomes only | 0/5 [0] | 8.0 ± 0.7 |
| XBY-S2 | 4/5 [80] | 9 |
| XBY-6 | 4/5 [80] | 11 |

Based on the preliminary results obtained with XBY-6 thioaptamer and Pichinde virus, it was determined if XBY-6 or XBY-S2 would have any antiviral activity against flaviviruses. West Nile virus was selected as a model system due to its high virulence in the mouse model. Mice were challenged with a low dose of virus (i.e., 30 pfu≈10 LD$_{50}$). The thioaptamers (10 μg) were delivered IP in Tfx50 liposomes and administered in two doses (one day before and 90 minutes before virus challenge). Control mice given PBS or liposomes succumbed to WN virus infection, while 80% of thioaptamer XBY-S2 treated animals survived challenge and remained healthy (Table 5). It was noted that both thioaptamers had antiviral activity. These results suggested that while the mechanism of protection may involve binding of XBY-6 to NF-κB or XBY-S2 to AP-1.

In previous studies with West Nile virus the present inventors had observed that animals had a brief viremia that peaked on day 3 μl prior to viral brain invasion. As such, three animals from each test group were sacrificed on days 3 and 6 post infection to determine viremias and virus infectivity levels in the brain. Accordingly, the protocol from the first study was repeated with increased group sizes of 16 mice (of which 6 would be sampled) and increasing the virus challenge to 100 LD$_{50}$ virus. As shown in Table 6, the initial results were reproducible. Both control groups (PBS and liposomes) succumbed to challenge with WN virus while the thioaptamer-treated mice survived and remained healthy. The proportion of mice treated with XBY-S2 thioaptamer who survived challenge was the same in both studies (80%) while XBY-6 treatment protected 50% of mice in the second study as compared to 80% of mice in the first study. These differences were not statistically significant given the small sample sizes.

To obtain fundamental information on the mechanism of protection, viremias and brain infectivity titers were measured in three mice sampled from each group on days 3 and 6 post infection (Table 7). As expected, viremias and brain infectivity titers in the control (PBS and liposome) groups detected on day 3 prior to invasion of the brain and virus detectable in the brains on day 6 post infection. The thioaptamer treated mice had reduced or undetectable viremias on day 3 post infection and no detectable virus infectivity in brains on day 6 post infection. These data indicate that the thioaptamer causes a reduction in the extraneuronal replication of the virus (as seen in the reduced viremias) and that there is insufficient virus to invade the central nervous system and cause encephalitic disease. The difference between virulent neuroinvasive strains of WN virus and poorly neuroinvasive attenuated WN strains may be explained by these results. Two mechanisms seem possible, although the invention is in no way limited by hypothesis: 1) first, the thioaptamer induces an immune response against WN virus; or 2) the thioaptamer blocks the WN virus replication. The thioaptamer may be inducing localized interferon (or other mediators of the innate immune response) that inhibits replication of the virus since the thioaptamer includes double-stranded DNA while double-stranded RNA is known to be an efficient inducer of interferon.

TABLE 6

Study 2: Female 3-4 week-old NIH Swiss mice were given aptamers at one day before and 90 minutes before administration of 100 $LD_{50}$ WN virus strain USA99b by the ip route.

| Group | # surviving [%] | AST(days ± SD) |
|---|---|---|
| PBS only | 0/10 [0] | 8.3 ± 0.8 |
| Liposomes only | 0/10 [0] | 7.7 ± 1.1 |
| XBY-S2 | 8/10 [80] | 8.5 ± 0.7 |
| XBY-6 | 5/10 [50] | 8.0 ± 0.7 |

To investigate the activity of the modified thioaptamers and the antiviral mechanism of action of the thioaptamers, the susceptibility of thioaptamer-protected mice virus to challenge was tested. Thioaptamer-treated mice from the second study who survived WN virus infection were challenged at 21 days post-infection with $100LD_{50}$ of WN virus. All mice, including mock-infected controls from study 2 succumbed to virus challenge. This result indicates that there was insufficient virus replication in thioaptamer-treated mice to induce an adaptive immune response. This would suggest that the mechanism of action of the thioaptamer is either innate immunity or direct antiviral activity of the thioaptamer.

Whether thioaptamers exhibited direct antiviral activity in cell culture was also determined. The direct antiviral activity of the thioaptamer was investigated in cell culture.

Using six-well dishes containing Vero cells, duplicate wells were treated with one of the following samples:

TABLE 7

Viremia and brain infectivity titers for Study 2 (see Table 6)

| | Day 3 | | Day 6 | |
|---|---|---|---|---|
| Sample | Serum titer (pfu/mL) | Brain titer (pfu/brain) | Serum titer (pfu/mL) | Brain titer (pfu/brain) |
| XBY-6 #1 | 30,000 | —* | — | — |
| XBY-6 #2 | — | — | — | — |
| XBY-6 #3 | 700 | — | — | — |
| XBY-S2 #1 | 100 | — | — | — |
| XBY-S2 #2 | — | — | — | — |
| XBY-S2 #3 | — | — | — | — |
| Lipo #1 | 2,000 | — | — | 500,000 |
| Lipo #2 | 2,500 | — | — | 6,500,000 |
| Lipo #3 | 15,000 | — | — | 3,500 |
| PBS #1 | 25,000 | — | 100 | 5,500,000 |
| PBS #2 | 20,000 | — | — | 180,000,000 |
| PBS #3 | 4,500 | — | — | 2,500,000 |

*— indicates no virus detected; limits of detection were 50 pfu/ml of serum and 25 pfu/brain 1. Liposomes + xbyc2 (10 µg/well)   2. Liposomes + xbys1 (10 µg/well)
3. Liposomes + XBY-S2 (5 µg/well)   4. Liposomes + XBY-S2 (10 µg/well)
4. Liposomes only                    5. Buffer only Wells were incubated for 12 hours with the samples above and then challenged with WN virus at a multiplicity of infection (MOI) of 0.1. Samples were harvested from each well at 0, 14, 24, 34 and 48 hours. No cytopathic effect was seen until 48 hours post virus infection. Each well was assayed at each time point by hemagglutination (HA) assay to detect the presence of virus particles. All samples showed no detectable HA (i.e., ≤4 HAU) except for the samples at 48 hours post virus infection when all wells had 32-64 HAUs. These results demonstrate that the thioaptamers have no direct antiviral activity.

One potential explanation for the antiviral activity of thioaptamers is induction of interferon. This hypothesis was investigated by taking groups of four 3-4 week-old female NIH Swiss and treat them with either 10 ug of XBY-S2 in liposomes, liposomes only, or buffer only on day 0 and day 1 post infection, followed by sacrificing mice on day 2 post infection. Serum samples were diluted 1 in 3 and run in ELISAs to detect mouse interferon-α/β, interferon-γ, or TNF-α. None of these cytokines was detected in the serum of any of the 12 mice sampled suggesting that interferon was not involved in the antiviral activity induced by thioaptamer XBY-S2.

FIG. 10 and Tables 5 and 6 demonstrate that the survival of P18 virus infected animals can be prolonged using thioaptamers and thioaptamers can protect the majority of the animals infected with West Nile virus. These results demonstrate that modified thioaptamers alter the outcome of in vivo viral infections by Category A and B agents by the manipulation of transcription factors involved in the immune response.

Figure 11:
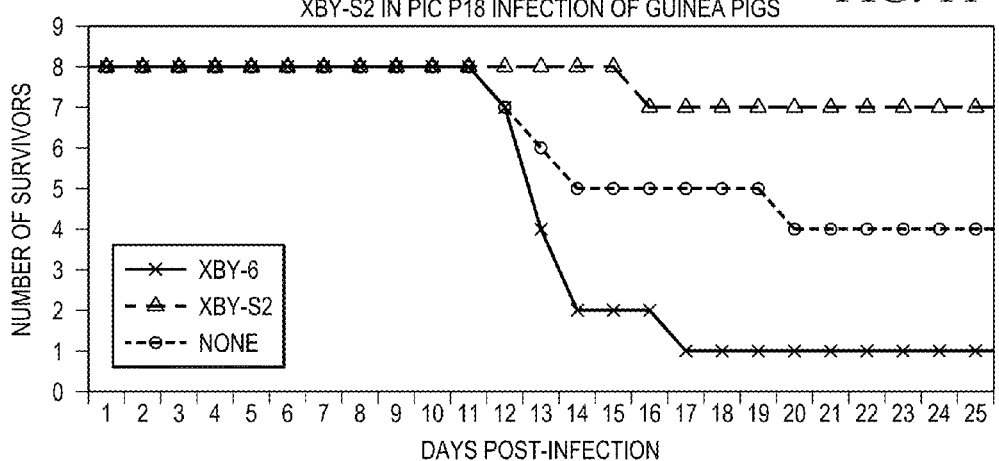
FIG. 11 is a graph that shows survival curves of guinea pigs with thioaptamers for infection by arenavirus.
Figure 12:
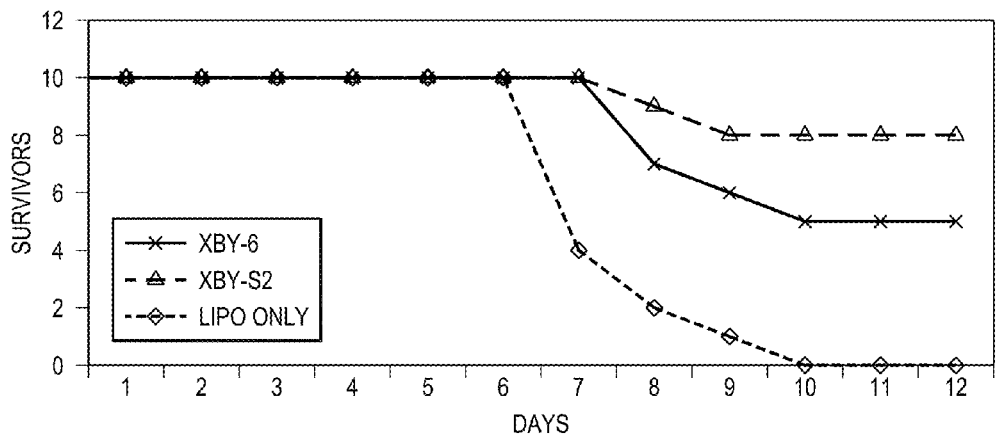
FIG. 12 is a graph that shows survival curves following West Nile Virus infection in guinea pigs treated with the NF-κB aptamer XBY-6, the AP-1 aptamer XBY-S2, or the liposome vehicle of animals infected by injection with lethal doses of West Nile Virus.
Figure 13:
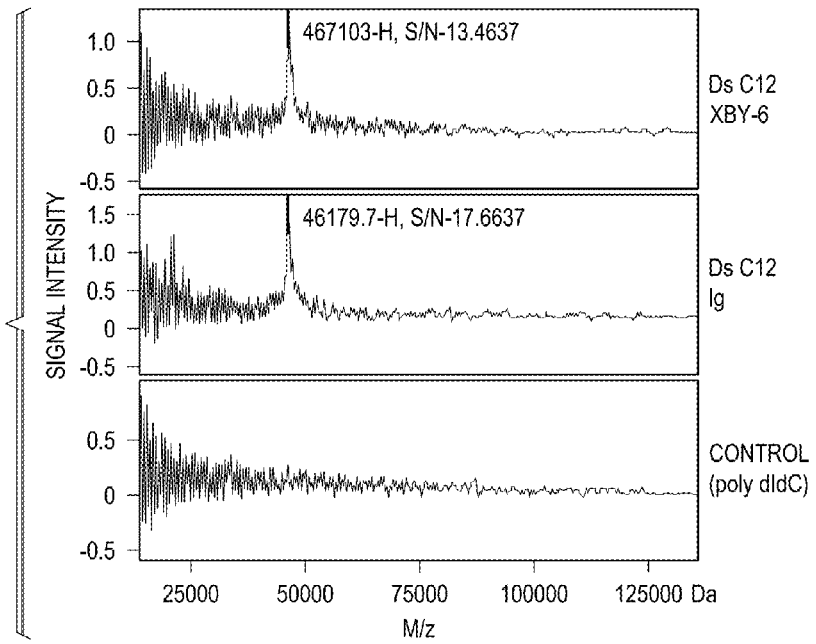
FIG. 13 are graphs that show SELDI detection of recombinant p50 using Epoxy-activated ProteinChip Arrays with XBY-6 (top), IgκB 22-mer duplex (middle) or control, poly (dI.dC) (bottom) covalently linked to surfaces.
Figure 14:
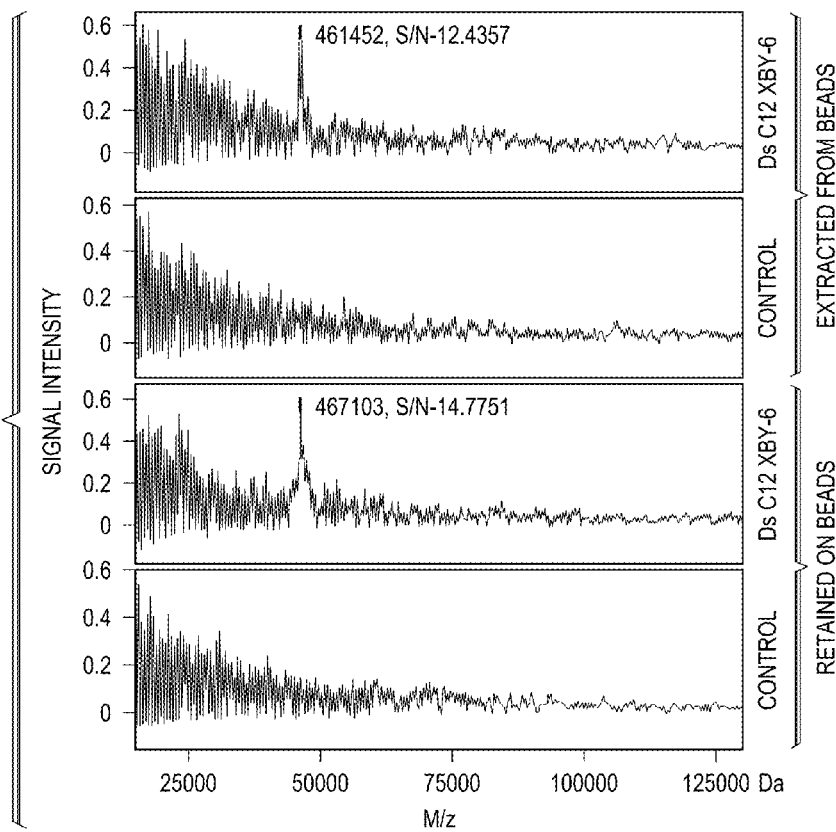
FIG. 14 are graphs that show the detection of recombinant p50 on gel beads using XBY-6. Top two SELDI MS extract from beads spotted onto NP20 ProteinChip. Bottom two SELDI spectra taken on beads themselves, in which the control is no XBY-6 covalently attached to beads with aminolinker.
Figure 15:
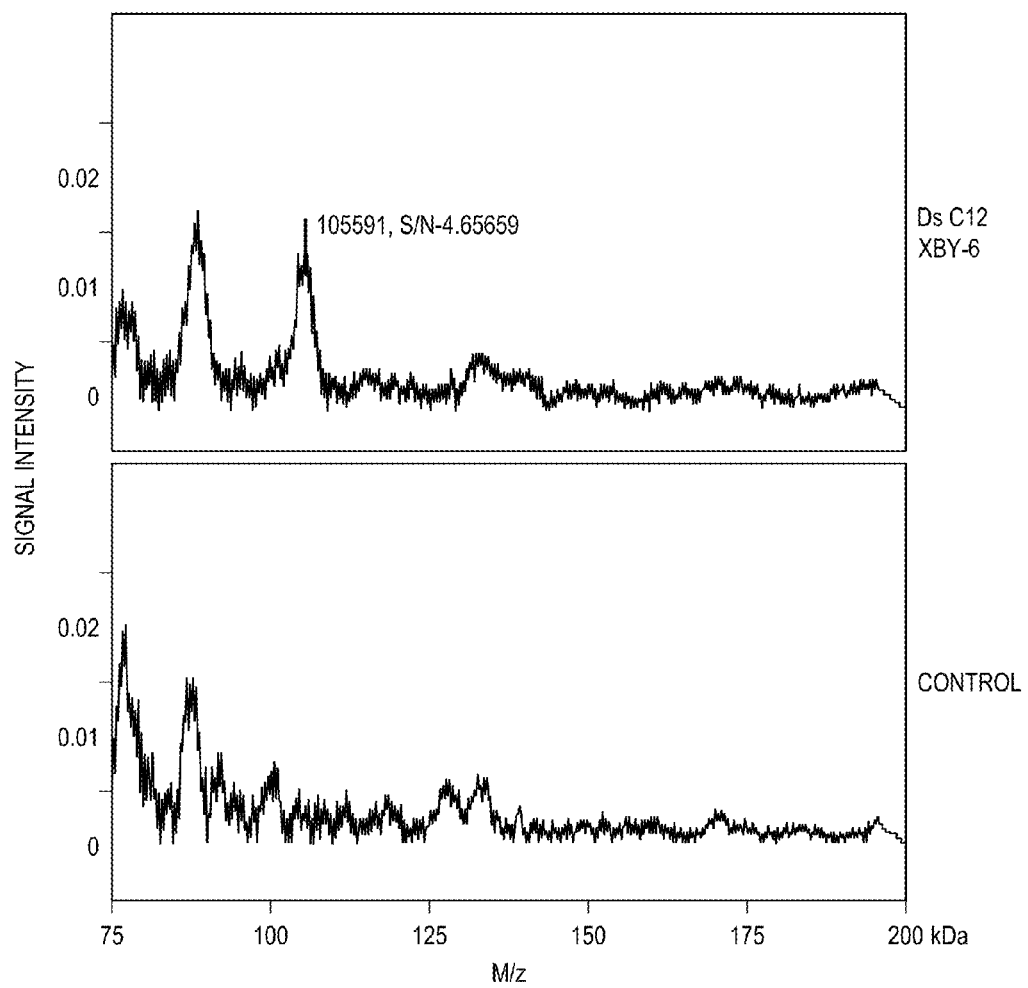
FIG. 15 is a graph that shows the SELDI MS capture of endogenous p50 (p105) from nuclear extracts on Ciphergen PS20 Proteinchip Arrays, the topgraph shows covalently linked XBY-6 to array surface, in the bottom, control no XBY-6 linked to surface.

FIG. 10 is a graph that shows survival curves following Pichinde P18 infection in guinea pigs treated with the NF-κB aptamer, XBY-6, the scrambled control, B92, or vehicle, MT, of animals infected by injection of 1000 pfu of Pichinde P18 at day 0, treatment consisted of intraperitoneal injections at days 0, 1 and 2;

FIG. 11 is a graph that shows survival curves of guinea pigs with thioaptamers for infection by arenavirus. FIG. 12 is a graph that shows survival curves following West Nile Virus infection in guinea pigs treated with the NF-κB aptamer XBY-6, the AP-1 aptamer XBY-S2, or the liposome vehicle of animals infected by injection with lethal doses of West Nile Virus.

SELDI MS Detection of NF-κB bound to Thioaptamer Surfaces and Beads. The present inventors have demonstrated that thioaptamers bind both purified, recombinant NF-κB p50 and nuclear extracts on either beads (or Ciphergen PBSII ProteinChip surfaces). FIGS. 13A-C are SELDI MS of p50 binding to various ProteinChips and beads. In FIG. 13A, Ciphergen's SELDI mass spectrometric methods were used to detect recombinant p50 with using epoxy-activated ProteinChip Arrays. Duplex aptamers with a 5'-amino terminus linked to a 12 carbon chain were synthesized. These duplex aptamers were the dithioate 14-mers XBY-6 (C12-XBY-6), the normal phosphate backbone 22-mer NF-κB binding site with the C12 5'-amino linker (C12-IgκB) or a non-specific, non-covalently linked duplex (polydIdC) as a control. These aptamers were spotted individually onto spots of a preactivated ProteinChip Array (PS20) in 2 μl of 25 mM $NaHCO_3$ (pH 9) and incubated overnight at room temperature and high humidity. Following incubation, excess aptamer was removed by washing 2 times in 5 μl 25 mM PBS, 0.1% Triton X-100 (pH 7.2) and the surface was blocked to limit non-specific binding with 1 μl of 100 μM bovine serum albumin for 4 hrs. After blocking, excess BSA was washed away as above. Next, 4.3 μmol recombinant p50 was spiked into 100 μmol BSA in 5 μl of optimized EMSA buffer containing 20 mM DTT, 0.01 μM polydIdC and incubated on each of the aptamer/thioaptamer surfaces for 2 hrs at room temperature and high humidity. Following incubation, each spot was washed with 5 μl of 50 mM Tris buffer (pH 7.2), 0.1% CHAPS, 1 M urea, 0.5 M NaCl, followed by a water wash to remove all non-specific binding components. 0.8 μl Sinapinic acid (saturated solution in 50% acetonitrile, 0.5% trifluoroacetic acid) was added to each spot, dried and the array analyzed in the mass reader. As shown in FIG. 13, the p50 (MW 46,200) on either the XBY-6 or IgκB bound surfaces was detected, but not the control. In other spectra with more stringent washing, the XBY-6 spot, but not the IgκB spot, was shown to retain the bound p50 (spectra not shown), confirming the tighter binding of p50 to XBY-6 (sub-nM) relative to IgκB ($K_D$ 4 nM).

FIG. 14 shows that the XBY-6 thioaptamer can also capture recombinant p50 (MW 46,200) on gel beads to which the 5'amino-C12 linked XBY-6 is coupled to 20 ul (1:1) AminoLink® Plus Coupling gel (Pierce, Immunoprecipitation kit, cat #45335). In this study, 3 μg of C12-XBY-6 was coupled overnight at 4° C. following the kit protocol. After quenching the gel, 6 μg of p50 in 1×EMSA buffer with polydIdC was added to the gel and incubated for 2 hrs with shaking at room temperature. The gel was washed to remove nonspecifically bound proteins, followed by one quick rinse with water. Protein bound to the gel was extracted with 5 μl of organic solvent (50% AcN and 0.01% TFA) with shaking for 20 min. All of the extracts were spotted onto NP20 ProteinChips, dried, followed by addition of saturated SPA and read on the Ciphergen PBSII MS (top two spectra). After extraction, 1 μl of the gel was loaded onto NP20 chip (bottom two spectra). Proteins still bound to the gel was analyzed using saturated SPA on the PBSII. Once again it was found that p50 can be identified by SELDI, both in the extract and retained directly on the beads.

FIG. 15 shows the capture of nuclear extracts onto Ciphergen's PS20 ProteinChip Arrays: Either 0.5 μg of C12-XBY-6, 0.25 pm of C12-IgκB or 0.5 μg of poly dIdC were incubated on PS20 chip overnight. The chips were blocked with 7 mg/ml BSA in PBS/0.1% Tween-20. Following blocking, 49 μg of nuclear extract in optimized EMSA buffer were incubated on each spot for 2 hr with shaking. Each spot was washed with PBS/0.1% Triton three times, followed by one quick wash with water. Proteins bound on each spot were analyzed using saturated SPA on the PBSII. These results indicate that a protein was bound with a MW ~105,591, which may represent p105, the precursor to p50 or the p50/p50 homodimer.

Bead-based phosphorodithioate and phosphorothioate thioaptamer combinatorial libraries and high throughput sorting against targeted proteins. The one-bead, one-aptamer split synthesis method disclosed herein was used to identify a specific ODN aptamer that targets proteins or other biomolecules. In combination with the split and pool synthesis combinatorial chemistry method for creating a combinatorial library of oligonucleotide agents (either phosphate, monothiophosphate or dithiophosphate; Gorenstein et al, U.S. patent issued, 2002 and pending, 1999 a,b, 2001, 2002; Yang et al., 2002, relevant portions incorporated herein by reference) both monothiophosphate and dithiophosphate combinatorial libraries attached to individual support beads were shown to produce aptamers that demonstrate target-specific binding Proteins that bind tightly to only a few of the $10^4$-$10^8$ different support beads may be selected by binding either purified proteins, nuclear or cytoplasmic extracts or pools of proteins to the beads and then identifying which beads have bound target protein by immunostaining, fluorescent staining techniques or MS (SELDI). Thus, the methods and compositions created and isolated thereby allow for rapid screening, isolation and identification of specific thioaptamers that bind to proteins such as NF-κB and AP-1 using the PCR-based identification tag of the selected bead disclosed herein.

Preparation and composition of the thioaptamer libraries and libraries of libraries. Depending on the nature of the targeted protein, thioaptamer combinatorial libraries were created that cover appropriate sequence space relative to the targeted protein. For transcription factors duplex thioaptamers were create that have a significant population of sequences similar to the consensus sequence. In the case of the in vitro combinatorial selection approach disclosed herein, the complexity of the library can be as large as $10^{14}$ different sequences and thus can cover all sequence space for a small (<22 nt) duplex. For the bead-based thioaptamer libraries, complexity is limited to the number of different beads $-10^6$-$10^8$, depending on their size.

To increase the complexity of the libraries one may also use a novel iterative approach in which a bead-based library of libraries of thioaptamers is made in which as many as $10^6$ different thioaptamers are attached to a single bead and thus have a total complexity of as many as $10^{12}$-$10^{14}$ sequences in the library of library. For example, a library of libraries was prepared on a 1 μmole scale of polystyrene beads (60-70 μm). The downstream and upstream primers, 5'-d(GGATCCGGTGGTCTG)-3' (SEQ ID NO.: 26) and 5'-d (CCTACTCGCGAATTC)-3' (SEQ ID NO.: 27) were synthesized in parallel on a two-column DNA synthesizer (Expedite 8909, Applied Biosystems). Following the 5'-primer, the sequences programmed on the synthesizer for the combinatorial library were 5'-AT*GN*GA*AT*TT*NC*CA 3' (SEQ ID NO.: 28) on column 1 and 5'-GG*AG*NG*CN*CA*GG*AC-3' (SEQ ID NO.: 29) on column 2 The 3'-primer sequence completed the 44-mer programmed on the synthesizer. A "split and pool" was used at each position indicated by an asterisk in order to synthesize the combinatorial region for the library of libraries. The letter N indicates a mixture of four bases (A, C, G and T). Five of the beads were randomly selected from the library and "one bead one PCR" was run, cloned and sequenced. The results listed below indicated the successful construction of the library of libraries.

```
E45-2-1:
5'-GG AG GA CT TT CC AC-3'     (SEQ ID NO.: 30)

E45-2-2:
5'-GG AG GA CA TT GC AC-3'     (SEQ ID NO.: 31)

E45-2-4:
5'-GG AG GA CC TT CC AC-3'     (SEQ ID NO.: 32)

E45-2-5:
5'-GG AG GA CC TT GC AC-3'     (SEQ ID NO.: 33)

E45-2-11:
5'-GG AG GA CN TT TC AC-3'     (SEQ ID NO.: 34)

E45-2-12:
5'-GG AG GA CC TT TC AC-3'     (SEQ ID NO.: 35)

E45-3-1:
5'-GG GA TG GT CA GG AC-3'     (SEQ ID NO.: 36)

E45-3-3:
5'-GG GC GG AT CA GG AC-3'     (SEQ ID NO.: 37)

E45-3-5:
5'-GG GA AG AT CA GG AC-3'     (SEQ ID NO.: 38)

E45-3-6:
5'-GG GG TG AT CA GG AC-3'     (SEQ ID NO.: 39)

E45-3-11:
5'-GG AG TG CT CA GG CA-3'     (SEQ ID NO.: 40)

E45-6-1:
5'-GG AG CG GT GT CC AC-3'     (SEQ ID NO.: 41)

E45-6-2:
5'-GG GA GG GA TT AC CA-3'     (SEQ ID NO.: 42)

E45-6-3:
5'-GG AG CG GT TT GC CA-3'     (SEQ ID NO.: 43)

E45-6-10:
5'-GG AG CG AT TT CC CA-3'     (SEQ ID NO.: 44)

E45-6-11
5'-GG AG AG GT TT TC CA-3'     (SEQ ID NO.: 45)

E45-7-1:
5'-AT AG GG CA CA GG AC-3'     (SEQ ID NO.: 46)

E45-7-2:
5'-AT AG NG CC CA GG AC-3'     (SEQ ID NO.: 47)

E45-7-5:
5'-AT AG GG CG CA GG AC-3'     (SEQ ID NO.: 48)

E45-8-1:
5'-GG AG GG CC CA GC AC-3'     (SEQ ID NO.: 49)

E45-8-2:
5'-GG AG AG CA CA TC AC-3'     (SEQ ID NO.: 50)

E45-8-3:
5'-GG AG CG CG CA CC AC-3'     (SEQ ID NO.: 51)

E45-8-4:
5'-GG AG CG CG CA GC AC-3'     (SEQ ID NO.: 52)

E45-8-5:
5'-GG AG GG CT CA GC AC-3'     (SEQ ID NO.: 53)

E45-8-6:
5'-GG AG AG CA CA AC AC-3'     (SEQ ID NO.: 54)

E45-8-10:
5'-GG AG CG CG CA TC AC-3'     (SEQ ID NO.: 55)

E45-8-11:
5'-GG AG AG CG CA CC AC-3'     (SEQ ID NO.: 56)
```

For proteins in which there are no known sequence to design the library, the user of the present invention begins with a single-strand (ss) DNA or RNA thioaptamers with at least 30 nts in the randomized or combinatorial regions. Using the methodology created and developed by the present inventors for creating both duplex and ss DNA and RNA thioaptamer libraries by both enzymatic and bead-based methods. One such technique is the one-bead, one-ODN library ligation reaction in which short (15 nucleotides) 5'- and 3'-sequences are sufficient to serve as primers for bead-based PCR (Yang et al., 2002). To achieve even longer combinatorial segments, it is possible to eliminate entirely one of the primer segments. High quality one-bead one-oligo libraries were contructed by join two pieces of DNA based on an enzymatic ligation reaction or using highly active phosphorothioate towards 5'-iodo groups on the ODN. Standard phosphoramidite chemistry was used for synthesis of 5' monophosphate ODN (5'-P(o)CCAGGAGATTCCAC-GGATCCGGTGGTCTGT-bead) (SEQ ID NO.: 57). The fully protected ODN with the non-cleavable linker beads were treated with concentrated ammonia at 37° C. for 21 hours to remove the protecting groups while allowing the ODN to remain attached to the beads. A selected single bead was mixed with the following components: 3 µl of 40 µM 15 mer oligonucleotide (5'-CCTACTCGCGAATTC-3', (SEQ ID NO.: 58) 3 µl of 10× ligation buffer, 3 µl of DMSO, 2 µl of T4 RNA ligase and 19 µl of ddH$_2$O. The reaction was performed at 5° C. for 17 hrs. The supernatant was removed carefully and washed with water. The single bead PCR reaction was run under established conditions. The PCR products were analyzed on a 15% native polyacrylamide gel. The PCR product was cloned using the TA Cloning procedure (Invitrogen) and sequenced on an ABI Prism 310 Genetic Analyzer (Applied Biosystems). The desired sequence (5'-CCTACTCGC-GAATTC-P(o)CCAGGAGATTCCAC-GGATCCGGTGGTCTGT-bead) (SEQ ID NO.: 58) was obtained.

These results show that the additional nucleic acid sequences may be added to the one-bead, one-ODN library with high quality and efficiency while maintaining the integrity of the library. The ligation reaction allows longer random regions of aptamers to be synthesized on the beads with higher yield since a primer region does not have to be stepwise synthesized onto the bead sequence. The beads were screened for the ability to bind the appropriate protein (such as the various NF-κB dimers or AP1 dimers) labeled with the Alexa Fluor 488 dye (Molecular Probes) or by binding fluorophor labeled antibodies as previously described. After thoroughly washing the protein-bound beads with PBS and 0.1% Tween 20 to minimize nonspecific binding, the beads are sorted using a multicolor flow cytometry and cell/bead sorting to visualize and sort the protein-bound thioaptamer beads and select the tightest binding thioaptamer-protein complexes as shown in FIG. 6. The most intensely stained beads will be retrieved. Initially, the inventors concentrated on the NFκB and AP-1 dimers, but these methods may be applied by to other proteins involved in the immune response. Multicolor flow cytometry was capable of sorting at speeds of $10^8$ beads per hour or viewed in terms of assays for thioaptamers binding to target proteins, $10^8$ assays per hour.

High throughput sorting (HTS) of homo- and heterodimers to thioaptamers by multi-color flow cytometry using multi-color flow cytometry HTS may be used to select thioaptamers that bind preferentially to heterodimers of proteins. As described above, one monomer is tagged fluorescently (A) with a dye (cy3 for example) and a different monomer (B) with another dye (cy5 for example). Both proteins are mixed together and allowed to bind to the bead thioaptamer library. Next, two-color flow cytometry is used to compare cy3/cy5 color levels of each bead. To select homodimers that have high affinity for homodimer A.A, beads that have high cy3 levels and low cy5 levels are selected. Conversely, high cy5/low cy3 indicates a thioaptamer sequence with selectivity for the B.B dimer For heterodimers, beads are selected for cy3/cy5 levels close to 1. SELDI MS may be used to determine which proteins have been bound to selected combinatory thioaptamer beads and also used with single bead PCR to identify which bead(s) in the combinatorial library have bound to protein(s).

More than 2 dyes and multi-color flow cytometry may be used to select various multimers. Thus, for NF-κB, at least 3 of the 5 different monomeric forms of the protein are combined, each with a different fluorphor and use 3-color flow cytometry to select thioaptamers that have high affinity and selectivity to homodimers A.A, B.B, C.C and various heterodimeric forms from the libraries. In principle, there are few limits to the number of detectable markers (e.g., fluorochromes) that may be used with the present invention, e.g., 5-color flow cytometry may be used.

Sequencing may also be performed directly on the bead. Each individually selected bead is washed thoroughly with 8 M urea (pH 7.2) to remove the protein and directly used for "one-bead one-PCR" amplification using the 5' and 3' end primers (Yang, et al. 2002). The PCR products are TA cloned and sequenced as previously described to create hybrid thioaptamers with normal phosphate, monothiophosphate, and dithiophosphate mixed backbones as well, keeping the total thiophosphate backbone below 80% to minimize "non-specific" sticking.

The current approach demonstrated in the above examples requires a different nucleotide sequence to identify a backbone modification. Thioaptamer libraries were also created that only differ in the position of phosphate or dithioate but not in its base sequence. It has been shown that the positions of thiophosphates in a mixed backbone S-ODN can be determined by reaction of the S-ODN with iodoethanol followed by base catalyzed cleavage of the thiophosphate triester. This approach was used to identifying the location of monothio- and dithiophosphate linkages, independent of base sequence.

Massively parallel, thioaptamer bead-based hts of the host and pathogen proteome may be used with the thioselection technology (both enzymatic [S]-ODN and synthetic [S]-ODN/[S$_2$]-ODN) to develop thioaptamers targeting very important proteins (e.g., NF-κB and AP-1) to identify promising therapeutic leads. Up to 1000's of different proteins in human and pathogen proteomes by using a massively parallel, thioaptamer bead-based HTS of the proteomes with specialized high-throughput multicolor flow cytometry/bead sorting in conjunction with SELDI™ mass-spectrometric methods to identify potential new therapeutic targets both of proteins involved in the immune response to BT viruses as well as viral proteins. Thioaptamers may be identified to inhibit the differentially expressed proteins in host-pathogen interactions as well as underlying immune response processes and so ameliorate cytopathological immune responses resulting in shock or to enhance "innate immunity" to help mount a more effective immune response.

Mass spectrometric protein detection technology can be used to identify bound proteins using HTS of thioaptamer beads. This approach has significant advantages, since MS is more sensitive than fluorescent imaging and will be very useful for low-abundance proteins. In addition, if more than one protein binds to a given thioaptamer bead, then it will be possible to identify and quantify these proteins by SELDI. This is particularly helpful for identifying non-covalent dimers such as NF-κB or AP-1 (there are 22 different monomeric forms of AP-1 and thus in principle 100's of different combinations of dimers possible).

Thioaptamer proteomic arrays were used to demonstrate the use of ProteinChip array technology (e.g., Ciphergen) for protein identification of modified thioaptamer beads or surfaces. SELDI MS combines the well-established principles of solid-phase extraction and time-of-flight mass spectrometry in a process known as surface enhanced laser desorption/ionization time-of-flight mass spectrometry. ProteinChip Arrays may be customized by covalently attaching affinity reagents such as the modified thioaptamers to the spot surface. If the biological marker to be detected is known and thioaptamer affinity reagents are available, affinity surfaces can be designed to make use of this specific thioaptamer-protein interaction. Also, because SELDI uses mass spectrometric detection, several assays can be multiplexed easily by taking advantage of the unique masses of each bound protein.

High-throughput screening (HTS) of thioaptamer libraries by flow cytometry and SELDI. Bead-based methods were used to identify both thioaptamer sequences and binding proteins in parallel, without the need to select one thioaptamer for each purified protein. A number of [S]-ODN or [S$_2$]-ODN combinatorial libraries are synthesized, each containing $10^6$ to $10^9$ different, but related members (or a library of library with up to $10^{14}$ sequences). The solid-phase split synthesis described herein may be used to create thioaptamer-bound bead libraries (one bead, one sequence or one library) as above. Each library can be sufficiently different to provide high affinity and selectivity to a small number of cellular proteins (such as AP-1 or NF-κB-type sequences). One or more of the thioaptamer library beads are incubated with cellular extracts, washed thoroughly to remove weakly bound proteins and the bound proteins visualized by direct fluorescent staining with cy3, cy5, SYPRO Ruby, or other newer dyes for high sensitivity (sub-nanogram). Fluorescently stained beads can be sorted in the high-speed cell/bead sorter for the top $10^2$ or more beads which have the highest amount of bound protein. The beads selected with the greatest amount of protein bound will then be analyzed by SELDI MALDI-TOF mass spectrometric techniques determine which proteins are bound to each bead; even if more than one protein binds to the bead, the thioaptamer may be used to identify a select group of proteins in cell extracts. The beads selected are then analyzed by SELDI methods to identify if a fairly limited number of different proteins are bound to the specific bead. Alternatively, proteolysis of the proteins on the bead with trypsin and analysis of the peptide fragments by LC MS/MS QTOF2 can be used to identify the proteins on each bead. After removal of protein from the beads by detergent and urea, the thioaptamer sequence on the bead can be determined by the PCR "one bead sequencing" method disclosed herein. Thus, a random library of "sticky beads" is selected and an extract containing the complete proteome to identify both the thioaptamer sequence on the single beads and the protein(s) bound.

HTS of combinatorial libraries to protein mixtures. Besides using cell extracts, known mixtures of hundreds of commercially available proteins (cytokines, transcription factors, etc.) may be applied to the mixture of thioaptamer bead libraries. HTS cell/bead sorting is used followed by MS identification of bound proteins. This involves direct SELDI determination of the protein or peptide fragmentation methods followed by MS identification of bound proteins. A major advantage in using thioaptamers rather than beads with proteins or monoclonal antibodies attached to them is that proteolysis and MS peptide identification is not complicated by proteolysis of bait proteins or Mab's. This approach can be used in parallel with other commercially available antibodies for virtually any protein (particularly AP-1), and serves as an alternative to the more general screening of the complete proteome and identification by SELDI MS methods alone. Once the sequences of the thioaptamers are identified, these are synthesized in larger quantities as reagents for diagnostics and therapeutics.

HTS of Thioaptamers Targeting Differentially Expressed Proteins in the Proteome in virus infected cells. The thioaptamer-based multi-color flow cytometry HTS may also be used for targeting differentially expressed proteins within the host and pathogen proteomes, combined with MS detection (SELDI). The thioaptamer bead-based combinatorial library can be used in conjunction with fluorescent tagging of proteins followed by SELDI MS to identify proteins differentially expressed in control vs. virus infected cells. In this simple two-color assay, a combinatorial library (or a combinatorial library of libraries) of thioaptamer beads may be synthesized, each bead with a single thioaptamer sequence (or a combinatorial library of thioaptamer sequences on each bead). Up to $10^8$ beads can be created with a single thioaptamer sequence on each bead. Cell extracts of a sample such as uninfected cells is labeled fluorescently with a dye (cy3 for example) as carried out previously and a virus-infected cell extract is then labeled fluorescently with another dye (cy5 for example). Both cell extracts are mixed together and allowed to bind to the bead thioaptamer library. Next, two-color flow cytometry is used to compare cy3/cy5 color levels of each bead. If cy3/cy5 level differs significantly (>2-fold) from 1, then the bead was captured. To determine which protein(s) have been bound to selected thioaptamer bead, SELDI MS will be used to characterize the bound target further. SELDI MS can be used to determine which proteins have been bound to selected combinatory thioaptamer libraries and also used with single bead PCR to identify which bead(s) in the combinatorial library have bound to protein(s). As shown above, Ciphergen's ProteinChip epoxy modified surfaces may be used to covalently attach 5'-amino-linker thioaptamers to beads. Ciphergen's ProteinChip array technology allows for solid-phase extraction to desorb more weakly bound proteins to thioaptamer surfaces, followed by surface enhanced laser desorption/ionization time-of-flight mass spectrometry (SELDI-MS). Other diseases besides viral infections may be similarly targeted using the thioaptamers, systems and methods disclosed herein.

HTS of thioaptamers targeting differentially expressed proteins in the proteome in virus infected cells relative to treated cells ("High Throughput Pharmacoproteomics"). In this embodiment, three-color thioaptamer library bead sorting is used. In this three-color assay, a combinatorial library (or a combinatorial library of libraries) of thioaptamer beads is synthesized, each bead with a single thioaptamer sequence (or a combinatorial library of thioaptamer sequences on each bead). Up to $10^8$ beads with a single thioaptamer sequence on each bead (or $10^{14}$ sequences on the library of libraries) are made. Uninfected cell extracts (or control extracts) are labeled fluorescently with a cy3 for example. A virus-infected cell extract (or any disease cell extract such as cancerous cells) is labeled fluorescently with cy5, and then a thioaptamer therapeutic treated, virus infected (or other disease) cell culture is labeled with a third dye. The three proteome cell extracts are mixed together in equal total protein quantities and allowed to bind to the bead thioaptamer library (or library of libraries). Three-color flow cytometry is used to compare cy3/cy5/dye 3 color levels of each bead. If cy3/cy5 level differs from 1 (uninfected vs. infected) and cy5/Sypro Ruby differs from 1 (infected vs. infected and treated) differs from 1, then the bead can be captured. Such a control assures that the thioaptamer drug previously identified as a promising lead does affect specific protein levels. To determine which protein(s) have been bound to selected thioaptamer beads, SELDI MS can be used to characterize the proteins bound to the target bead.

In one embodiment of the invention a complex of combinatorial libraries are created in which multiple transcription factor-like sequences with varying thiophosphate substitution patterns are concatenated in a single long sequence so that it can bind to multiple transcription factors such as NF-κB, AP-1, SP-1, GRE, SRE, etc., requiring a thioaptamer sequence of at least 20-40-mers. These embodiments provide an attractive approach to defining therapeutic strategies in which multiple proteins can be targeted with multiple thioaptamers. Such a combination (adjuvant) of drug therapeutics is needed to improve immune responses in cancer, AIDS, etc. Mammalian protein signaling pathways are often redundant so that if one pathway is affected, another can take over control. By perturbing multiple, highly interwoven pathways, a greater opportunity to modulate the immune response network is made available.

HT flow cytometry and bead selection. High-throughput screening (HTS) of thioaptamer beads using high-speed multicolor flow cytometry/cell sorting is used. In principle, more than $10^{10}$ beads could be screened within a single day, and specific bead subpopulations could be sorted for subsequent proteomics analysis. This group also has considerable experience in HTS of cells and bacteria (as well as beads) for subsequent molecular characterizations by PCR and gene expression microarray analysis.

Advanced HTS technologies may be used for large library screening and functional genomics. Single-cell (or bead) sorting of rare subpopulations may be used to isolate single beads from combinatorial libraries. A special high speed sorter uses a unique two-stage signal processing system, configured in hardware as a single layer neural network, which allows for sophisticated cell or bead classifications based on multivariate statistics or learning through neural networks.

A 6-color high-speed flow cytometer/cell sorter is configured in hardware and software as a single-layer neural network that can also be used to generate real-time sort decisions on the basis of multivariate statistical classification functions. While it can perform the usual two-way sorts it is commonly used in "straight-ahead" sorting mode to allow for extremely high sort recovery and purity at high throughput rates or to efficiently sort single cells for cloning or for subsequent molecular characterizations by PCR.

Multi-color flow cytometry as a quantitation and validation tool for proteomics. These capabilities can also be used to sort for thioaptamers that bind heterodimers or more complex protein mixtures. By using different fluorescently labeled dyes bound to specific proteins, beads are sorted simultaneously that bind homodimers and heterodimers. A covalently labeled p50 with Alexa-Fluor 488 dye was isolated (data not shown) and carried out 1- and 2-color thioaptamer bead sorting.

Production of large quantities of hybrid dithiophosphate aptamer. Using chemistry developed independently in both Caruthers' and Gorenstein's laboratory, the most promising dithioate hybrid backbone aptamers show good in vitro and in vivo binding to the targets will be synthesized (Cho et al., 1993; Farschtschi & Gorenstein, 1988; Gorenstein et al., 1990; Gorenstein et al., 1992; Piotto et al., 1991) on a 5-10 μmole scale and purified (Mono Q; Yang et al., 1999; 2002).

Preparation of nuclear and cytoplasmic extracts was conducted at various times after virus infection, and parallel uninfected control cultures of $5 \times 10^7$ cells are harvested and collected by centrifugation. Cell pellets are resuspended and washed in phosphate buffered saline (PBS). Next, cells are lysed and the cytoplasmic and nuclear fractions isolated. The nuclei are purified by centrifugation through a cushion of 2M sucrose before protein extraction. The protein content in all fractions will be determined by BCA Assay according the manufacturer's directions (Pierce, Rockford, Ill.).

Mass spectrometric identification of bound proteins. As demonstrated above, sorted "positive" beads can be subjected to SELDI-MS analysis to confirm the identity of the proteins bound to the thioaptamer beads of the present invention (via MALDI MS molecular ion characterization). In cases where the "positive" bead's thioaptamer might have bound not only the target protein but other proteins in a sample, e.g., a secondary or even tertiary, etc. protein, SELDI-MS may be used to identify this event through the detection of multiple molecular ions.

Liquid Chromatography/Tandem Mass Spectrometry (LC/MS/MS). For proteins which cannot be identified from the MI, proteolysis and multidimensional LC applying 2D chromatographic separation of peptides is used on-line with MS analysis (Link et al., 1999; Washburn et al., 2001). This LC tandem MS approach is carried out using strong cation exchange (SCX) chromatography combined with reversed-phase (RP) chromatography. Using a salt step gradient, tryptic peptides of complexes are eluted from the SCX column onto the RP column, and contaminants of salts and buffers are washed to waste using a diverter valve. Peptides are subsequently eluted from the RF column directly into the MS, either for mass fingerprinting, or for MS/MS sequence analysis. This LC tandem MS procedure is very useful for small amounts (femtomol) of complex. Yet another procedure is tandem LC/tandem MS. The proteomes can be either human, GP, hampster or mouse—human and mouse genome databases are available.

LC or 2D SDS-PAGE and MS. These techniques are currently the major analytical tools used to identify proteins in the proteome. Thioaptamer bead libraries may be used to differentially screen the proteomes, using 2D gel analysis for differential analysis of protein expression. To improve the comparative analysis of gel imaging imaging software may be used to improve result resolution, e.g., using Nonlinear USA, Inc. (Progenesis). The automated imaging features of this 2D imaging software reduce gel evaluation times substantially and are an important step towards hands-free analysis.

2D gel electrophoresis. 2D PAGE can be conducted essentially as first described by (O'Farrell, 1975). High-throughput may be employed Pharmacia's IPGphor multiple sample IEF device or the first dimension, and Biorad's multiple gel SDS-PAGE systems (Protean Plus and Criterion dodeca cells) for the second. Gels will be stained with either SYPRO Ruby for high sensitivity (sub-nanogram) or Coomassie Blue when less sensitivity is required. Image analysis of gels will be achieved with a Perkin Elmer (PE) ProEXPRESS Proteomic Imaging System using Nonlinear's Progenesis imaging software. A Genomic Solutions' robotics recently purchased is utilized for protein spot picking and for sample trypsin hydrolysis (Proteomic Protein Picker), and sample clean-up, and sample application to MALDI plates (ProPrep 4 Block System). Mass fingerprinting for protein identification may use an Applied Biosystems (AB) matrix-assisted laser desorption/ionization (MALDI) time-of-flight (TOF) Voyager DE STR MS. Proteins will be identified with the Voyager's Prospector software. De novo sequencing and analysis of posttranslational modifications can be achieved by electrospray (ESI) MS/MS (capillary LC nanoflow option).

Isotope-coded affinity tags (ICAT). Some differential protein expression use isotope-coded affinity tags (ICATs) for quantitative analysis of complex protein mixtures (Gygi et al., 1999). In this procedure, there is an option to fractionate proteins before to proteolysis decreases the complexity of proteins analyzed.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

REFERENCE LIST

Aronson, J. F., Herzog, N. K., & Jerrells, T. R. (1994) "Pathological and virological features of arenavirus disease in guinea pigs: Comparison of two Pichinde virus strains," *Am. J. Patholo* 145, 228-235.

Aronson, J. F., Herzog, N. K., & Jerrells, T. R. (1995) "Tumor Necrosis Factor (TNF) Plays a Role in the Pathogenesis of Guinea Pig Arenavirus Disease," *Amer. J. Trop. Med. Hygien* 52, 262-269.

Bachelin, M., Hessler, G., Kurz, G., Hacia, J. G., Dervan, P. B., & Kessler, H. (1998) "Structure of a stereoregular phosphorothioate DNA/RNA duplex," *Nature Struct. Biol.* 5, 271-276.

Berglund, J. A., Charpentier, B., & Rosbash, M. (1997) "A High Affinity Binding Site for the HIV-1 Nucleocapsid Protein," *Nucleic Acid Res.* 25(5): 1042-1049.

Bielinska, A., Shivdasani, R. A., Zhang, L. Q., & Nabel, G. J. (1990) "Regulation of Gene Expression with Double-Stranded Phosphorothioate Oligonucleotides," *Science* 250, 997-1000.

Boccaccio, C., Ando, M., Tamagnone, L., Bardelli, A., Michieli, P., Battistini, C., & Comoglio, P. M. (1998) "Induction of Epithelial Tubules by Growth Factor HGF Depends on the STAT Pathway," *Nature* 391, 285-288.

Brill, W. K. D., Nielsen, J., & Caruthers, M. H. (1988) "Synthesis of Dinucleoside Phosphorodithioates via Thioamidites," *Tetrahedron Lett.* 29, 5517-5520.

Brill, W. K. D., Tang, J. Y., Ma, Y. X., & Caruthers, M. H. (1989) "Synthesis of Oligodeoxynucleoside Phosphorodithioates via Thioamidites," *J. Am. Chem. Soc.* 111, 2321-2322.

Burke, D. H., Scates, L., Andrews, K., & Gold, L. (1996) "Bent Pseudoknots and Novel RNA Inhibitors of Type 1 Human Immunodeficiency Virus (HIV-1) Reverse Transcriptase," *J. Mol. Biol.* 264, 650-666.

Carteau, S., Batson, S. C., Poljak, L., Mouscadet, J. F., Derocquigny, H., Darlix, J. L., Kas, E., & Auclair, C. (1997) "Human Immunodeficiency Virus Type 1 Nucleocapsid protein Specifically Stimulates MG2+-Dependent DNA Inegration in vitro," *J. Virol.* 71, 6225-6229.

Chen, F. E., Huang, D. B., Chen, Y. Q., & Gosh, G. (1998) "Crystal Structure of P50/P65 Heterodimer of Transcription Factor NF-κB Bound to DNA," *Nature* 5, 391-410.

Chen, H. & Gold, L. (1994) "Selection of high-affinity RNA ligands to reverse transcriptase: Inhibition of cDNA synthesis and RNase H activity," *Biochemistry* 33, 8746-8756.

Chen, Y. Q., Ghosh, S., & Ghosh, G. (1998) "A novel DNA Recognition Mode by the NK-κB P65 Homodimer," *Nat. Struct. Biol.* 5, 67. Cho-Chung, Y. S. (1998) "CRE-Palindrome Oligonucleotide as a Transcription Factor Decoy and an Inhibitor of Tumor Growth," *Antisense & Nucleic Acid Drug Development* 8, 167-170.

Cho, Y. S., Zhu, F. C., Luxon, B. A., & Gorenstein, D. G. (1993) "2D H-1 and P-31 NMR Spectra and Distorted A-DNA-Like Duplex Structure of a Phosphorodithioate Oligonucleotide," *J. Biomol. Struct. Dyn.* 11, 685-702.

Ciafre, S. A., Rinaldi, M., Gasparini, P., Seripa, D., Bisceglia, L., Zelante, L., Farace, M. G., & Fazio, V. M. (1995) "Stability and functional effectiveness of phosphorothioate modified duplex DNA and synthetic 'mini-genes'," *Nucleic Acids Research* 23, 4134-4142.

Cummins, D. (1990) "Lassa fever.," *Br. J. Hosp. Med.* 43, 186-192.

Dyer, R. B. & Herzog, N. K. (1995) "Immunodepletion EMSA: A Novel Method to Identify Proteins in a Protein/DNA Complex," *Nucleic Acids Res.* 23, 3345-3346.

Dyer, R. B. and Herzog, N. K. (1995). Isolation of Intact Nuclei for Nuclear Extract Preparation from Fragile B-Lymphocyte Cell Lines. *Biotechniques* 19, 192-195.

Dyer, R. B., Collaco, C., Niesel, D. W., and Herzog, N. K. (1993). *Shigella flexneri* invasion of HeLa cells induces B DNA-binding activity. *Infection and Immunity* 61, 4427-4433.

Eckstein, F. (1985) "Nucleoside Phosphorothioates," *Ann. Rev. Biochem.* 54, 367-402.

Ekland, E. H., Szostak, J. W., & Bartel, D. P. (1995) "Structurally complex and Highly Active RNA Ligases Derived from Random RNA Sequences," *Science* 269, 364-370.

Eleouet, J. F., Chilmonczyk, S., Besnardeau, L., & Laude, H. (1998) "Transmissible Gastroenteritis Coronavirus Induces Programmed Cell Death in Infected Cells through a Caspase-Dependent Pathway," *J. Virol.* 72, 4918-4924.

Farschtschi, N. & Gorenstein, D. G. (1988) "Preparation of a Deoxynucleoside Thiophosphoramidite Intermediate in the Synthesis of Nucleoside Phosphorodithioates," *Tetrahedron Lett.* 29, 6843-6846.

Felder, E. R. (1999) Resins, Linkers And Reactions For Solid-Phase Synthesis Of Organic Libraries. In Miertus, S. (ed.), In *Combinatorial Chemistry and Technology, Principles, Methods and Applications*. Marcel Dekker, Inc., NY, pp. 35-51.

Fennewald, S. M., Aronson, J. F., Zhang, L., and Herzog, N. K. (2002). Alterations in NF-κB and RBP-Jκ by arenavirus infection of macrophages in vitro and in vivo. *Journal of Virology* 76, 1154-1162.

Ghosh, G., Van Duyne, G., Ghosh, S., & Sigler, P. B. (1995) "Structure of NF-κB P50 Homodimer Bound to NF-κB Site," *Nature* 373, 303-310.

Gold, L., Brown, D., He, Y. Y., Shtatland, T., Singer, B. S., & Wu, Y. (1997) "From Oligonucleotide Shapes to Genomic Selex—Novel Biological Regulatory Loops," *Proc. Natl. Acad. Sci. U.S.A.* 94, 59-64.

Gold, L., Polisky, B., Uhlenbeck, O., & Yarus, M. (1995) "Diversity of oligonucleotide functions," *Annu. Rev. Biochem.* 64, 763-797.

Goldfeld, A. E., Doyle, C., & Maniatis, T. (1990) "Human tumor necrosis factor alpha gene regulation by virus and lipopolysaccharide.," *Proceedings of the National Academy of Sciences of the USA* 87, 9769-9773.

Gonzalez, C., Stec, W., Reynolds, M. A., & James, T. L. (1995) "Structure and dynamics of a DNA center dot RNA hybrid duplex with a chiral phosphorothioate moiety: NMR and molecular dynamics with conventional and time-averaged restraints," *Biochemistry* 34, 4969-4982.

Gorenstein, D. G. (1994) "Conformation and Dynamics of DNA and Protein-DNA Complexes by $^{31}$P NMR," *Chem. Rev.* 94, 1315-1338.

Gorenstein, D. G. and Farschtschi, N., U.S. Pat. No. 5,218,088, Process for Preparing Dithiophosphate Oligonucleotide Analogs via Nucleoside Thiophosphoramidite Intermediates (Awarded, Jun. 8, 1993; Applied 1989).

Gorenstein, D. G., Fanni, T., Taira, K., & Farschtshi, N. (1990) "Stereoelectronic Effects in the Hydrolysis of Phosphonium Ions from Acyclic and Bicyclic Phosphates and Phosphorothionates," *Phosphorus, Sulfur, and Silicon* 47, 93-104.

Gorenstein, D. G., Karslake, C., Granger, J. N., Cho, Y., & Piotto, M. E. (1992) in *Phosphorus Chemistry (ACS Symposium Series)* (Walsh, E. N., Griffith, E. J., Parry, R. W., & Quin, L. D., Eds.) pp 202-217, American Chemical Society, Washington, D. C.

Gorenstein, D. G, King, D. J., Ventura, and D. A., Brasier, A. R. U.S. patent "Combinatorial Selection of Oligonucleotide Aptamers" (Applied October, 1998).

Gorenstein, D. G., Herzog, N., Aronson, J., and Luxon, B., U.S. patent pending, "Thio-modified Aptamer Synthetic Methods and Compositions" (Applied October, 1999).

Gorenstein, D. G., Herzog, N., Aronson, J., and Luxon, B., Foreign patent pending, "Thio-modified Aptamer Synthetic Methods and Compositions" (Applied October, 1999).

Gorenstein, D. G., Luxon, B., Herzog, N. and Yang, X. B., patent application, "Phosphoromonothioate and Green, L., Waugh, S., Binkley, J. P., Hostomska, Z., Hostomsky, Z., & Tuerk, C. (1995) "Comprehensive chemical modification interference analysis of an RNA pseudoknot inhibitor to HIV-1 reverse transcriptase," *J. Mol. Biol.* 247, 60-68.

Hilaire, P. M. St. and Meldal, M. (2000) Glycopeptide and oligosaccharide libraries. *Angew. Chem. Int. Ed.*, 39, 1162-1179.

Holland, J. H. (1994) in AnonymousMIT Press, Cambridge, Mass.

Jahrling, P. B., Hesse, R. A., Rhoderick, J. B., Elwell, M. A., & Moe, J. B. (1981) "Pathogenesis of a Pichinde virus strain adapted to produce lethal infections in guinea pigs," *Infect. Immun.* 32, 872-880.

Jhaveri, S., Olwin, B., & Ellington, A. D. (1998) "In Vitro Selection of Phosphorothiolated Aptamers," *Bioorganic and Medicinal Chemistry Letters* 8, 2285-2290.

Jin, G. & Howe, P. H. (1997) "Regulation of Clusterin Gene Expression by Transforming Growth Factor b," *J. Biol. Chem.* 272, 26620-26626.

King, D. J., Ventura, D. A., Brasier, A. R. and Gorenstein, D. G., "Novel Combinatorial Selection of Phosphorothioate Oligonucleotide Aptamers," *Biochemistry*, 37,16489-16493 (1998).

King, D. J., Bassett, S. E., Li, X., FennewaldS. A., Herzog, N. K., Luxon, B. A., Shope, R., & Gorenstein, D. G. (2002) "Combinatorial selection and binding of phosphorothioate aptamers targeting human NF kappa B Rel A and p50.," *Biochemistry*, in press.

Lackey, D. B. & Patel, J. (1997) "Biomedical Synthesis of Chirally Pure RP Oligonucleotide Phosphorothioates," *Biotechn. Lett.* 19, 475-478.

Lam, K. S., et al., (1991) "A new type of synthetic peptide library for identifying ligand-binding activity. *Nature*, 354, 82-84.

Lam, K. S. (1995) Synthetic peptide libraries. In Molecular Biology and Biotechnology: A Comprehensive Desk Reference. Meyer, R. A. (ed.) p. 880. VCH Publisher: NY.).

Leary J F, Schmidt D F, Gram J G, McLaughlin S R, Dalla T C, Burde S: High-speed flow cytometric analysis and sorting of human fetal cells from maternal blood for molecular characterization. *Annals of the New York Academy of Sciences* 1994, 731:138-141.

Leary, J. F., Corio, M. A., McLaughlin, S. R. System for High-Speed Measurement and Sorting of Particles U.S. Pat. Nos. 5,204,884 (1993) and 5,804,143 (1998)

Leary, J. F. Strategies for Rare Cell Detection and Isolation In: *Methods in Cell Biology: Flow Cytometry* (Edited by Z. Darzynkiewicz, J. P. Robinson, H. A. Crissman) vol. 42: pp. 331-358 (1994).

Leary, J. F., Schmidt, D., Gram, J. G., McLaughlin, S. R., DellaTorre, C., Ellis, S. P. Isolation of Rare Cells by High-Speed Flow Cytometry and High-Resolution Cell Sorting for Subsequent Molecular Characterization-Applications in Prenatal Diagnosis, Breast Cancer and Autologous Bone Marrow Transplantation In: Basic and Clinical Applications of Flow Cytometry. F. A. Valeriote, A. Nakeef, M. Valdivieso, Eds., Kluwer Academic Publishers, Boston, 1996, pp. 271-318.

Leary, J. F., McLaughlin, S. R., Kavanau, K. New Methods for Detection, Analysis and Isolation of Rare Cell Populations *SPIE* 2982: 240-253, 1996.

Leary, J. F., He, F., Reece, L. N. Detection and Isolation of Single Tumor Cells Containing Mutated DNA Sequences *SPIE* 3603: 93-101, 1999.

Lebedev, A. V. & Wickstrom, E. (1996) "The Chirality Problem in P-Substituted Oligonucleotides," *Perspectives in Drug Discovery & Design* 4, 17-40.

Lebruska, L. L. & Maher, I. L. J. (1999) "Selection and Characterization of an RNA Decoy for Transcription Factor NF-κB.," *Biochemistry* 38, 3168-3174.

Liang, R., Yan, L., Loebach, J., Ge, M., Uozumi, Y., Sekanina, K., Horan, N., Gildersleeve, J., Thompson, C., Smith, A., Biswas, K., Still, W. C., & Kahne, D. (1996) "Science," *Science* 274, 1520-1522.

Liang, R., et al., (1996) Parallel synthesis and screening of a solid phase carbohydrate library. *Science*, 274, 1520-1522.

Lin, K. I., DiDonato, J. A., Hoffmann, A., Hardwick, J. M., & Ratan, R. R. (1998) "Suppression of steady-state, but not stimulus-induced NF-κB activity inhibits alphavirus-induced apoptosis," *J. Cell. Biol.* 141, 1479-1487.

Mann, M. J. (1998) "E2F Decoy Oligonucleotide for Genetic Engineering of Vascular Bypass Grafts," *Antisense & Nucleic Acid Drug Development* 8, 171-176.

Marshall, W. S. & Caruthers, M. H. (1993) "Phosphorodithioate DNA as a potential therapeutic drug. [Review]," *Science* 259, 1564-1570.

Milligan, J. F. & Uhlenbeck, O. C. (1989) "Determination of RNA-protein contacts using thiophosphate substitutions," *Biochemistry* 28, 2849-2855.

Morishita, R., Gibbons, G. H., Horiuchi, M., Ellison, K. E., Nakama, M., Zhang, L., Kaneda, Y., Ogihara, T., & Dzau, V. J. (1995) "A Gene Therapy Strategy Using a Transcription Factor Decoy of the E2F Binding Site Inhibits Smooth Muscle Proliferation in Vivo," *Proc. Natl. Acad. Sci. USA.* 92, 5855-5859.

Morishita, R., Higaki, J., Tomita, N., & Ogihara, T. (1998) "Application of Transcription Factor "Decoy" Strategy as means of Gene Therapy and Study of Gene Expression in Cardiovascular Disease," *Circulation Research* 82, 1023-1028.

Morishita, R., Sugimoto, T., Aoki, M., Kida, I., Tomita, N., Moriguchi, A., Maeda, K., Sawa, Y., Kaneda, Y., Higaki, J., & Ogihara, T. (1997) "In vivo Transfection of cis Element "Decoy" against Nuclear Factor-κB Binding Site Prevents Myocardial Infarction.," *Nature Medicine* 3, 894-899.

Muller, C. W., Rey, F. A., Sodeoka, M., Verdine, G. L., & Harrison, S. C. (1995) "The NK-κB P50 Homodimer Bound to DNA," *Nature* 1995, 311-317.

Murphy, K., Haudek, S. B., Thompson, M., & Giroir, B. P. (1998) "Molecular biology of septic shock," *New Horizons* 6, 181-193.

Nakamaye, K. L., Gish, G., Eckstein, F., & Vosberg, H. P. (1988) "Direct sequencing of polymerase chain reaction amplified DNA fragments through the incorporation of deoxynucleoside alpha-thiotriphosphates," *Nucleic Acids Res.* 16, 9947-9959.

Osborne, S. E., Matsumara, I., & Ellington, A. D. (1997) "Aptamers as Therapeutic and Diagnostic Reagents: Problems and Prospects," *Current Opinion in Chem. Biol.* 1, 5-9.

Otwinowski, Z., Schevitz, R. W., Zhang, R. G., Lawson, C. L., Joachimiak, A., Marmorstein, R. Q., Luisi, B. F., & Sigler, P. B. (1988) "Crystal structure of trp repressor/operator complex at atomic resolution," *Nature* 335, 321.

Park, Y. G., Nesterova, M., Agrawal, S., & Cho-Chung, Y. S. (1999) "Dual Blockade of Cyclic AMP Response Element-(CRE) and AP-ldirected Transcription by CRE-transcription Factor Decoy Oligonucleotide," *J. Biol. Chem.* 274, 1573-1580.

Peters, C. J., Jahrling, P. B., Liu, C. T., Kenyon, R. H., McKee, Jr. K. T., & Barrera-Oro, J. G. (1987) "Experimental studies of arenavirus hemorrhagic fevers," *Current Topics in Microbiol. and Immunol.* 134, 5-68.

Schneider, D. J., Feigon, J., Hostomsky, Z., & Gold, L. (1995) "High-affinity ssDNA inhibitors of the reverse transcriptase of type 1 human immunodeficiency virus," *Biochemistry* 34, 9599-9610.

Sharma, H. W., Perez, J. R., Higgins-Sochaski, K., Hsiao, R., & Narayanan, R. (1996) "Transcription factor decoy approach to decipher the role of NF-kappa B in oncogenesis," *Anticancer Res.* 16, 61-69.

Stec, W. J., Grajkowski, A., Koziolkiewicz, M., & Uznanski, B. (1991) "Novel Route to Oligo(Deoxyribonucleoside Phosphorothioates)-Stereocontrolled Synthesis of P-Chiral Oligo (Deoxy-ribonucleoside Phosphorothioates)," *Nucleic Acids Res.* 19, 5883-5888.

Sterner, J. M. & Leary, J. F. (1989) "Use of biocarrier beads and flow cytometry for single-cell studies of fibronectin gene regulation in dibutyrl cyclic AMP reverse transformed CHO-K1 cells," *Cell Biophysics* 15, Tian, Y., Adya, N., Wagner, S., Giam, C. Z., Green, M. R., & Ellington, A. D. (1995) "Dissecting protein:protein interactions between transcription factors with an RNA aptamer," *RNA.* 1, 317-326.

Tomita, N., Morishita, R., Higaki, J., & Ogihara, T. (1997) "A Novel Strategy for Gene Therapy and Gene Regulation Analysis Using Transcription Factor Decoy Oligonucleotides," *Exp. Nephrol.* 5, 429-434.

Velasco, M., Diaz-Guerra, M. J. M., Martin-Sanz, P., Alvarez, A., & Bosca, L. (1997) "Rapid up-regulation of IκBb and abrogation of NF-κB activity in peritoneal macrophages stimulated with lipopolysaccharide," *J. Biol. Chem.* 272, 23025-23030.

Volk, D., Yang, X.-B., Fennewald, S. M., Bassett, S., Venkitachalam, S., Herzog, N., Luxon, B., & Gorenstein, D. *Bioorganic Chemistry* (in press).

Wang, S., Lee, R. J., Cauchon, G., Gorenstein, D. G. and Low, P. S. "Delivery of Antisense Oligonucleotides against the Human Epidermal Growth Factor Receptor into Cultured KB Cells with Liposomes Conjugated to Folate via polyethylene glycol," *Proc. Natl. Acad. Sci., U.S.A.,* 92 3318-3322 (1995).

Yang, X., Fennewald, S., Luxon, B. A., Aronson, J., Herzog, N. K., & Gorenstein, D. G. (1999) "Aptamers containing thymidine 3'-0-phosphorodithioates: synthesis and binding to nuclear factor-κB," *Bioorganic & Med. Chem. Lett.* 9, 3357-3362.

Yang, X., Bassett, S. E., Li, X., Luxon, B. A., Prow, R. K. T. W., Leary, J. F., Ellington, A., & Gorenstein, D. G. (2002a) "Construction and selection of bead bound combinatorial oligonucleoside phosphorothioate and phosphorodithioate aptamer libraries designed for rapid PCR-based sequencing," Nucleic Acids Res. 30, 1-8.

Yang, X-B., Hodge, R., Luxon, B. A., Shope, R., Gorenstein, D. G. 2002b), "Separation of Synthetic Oligonucleotide Dithioates from Monothiophosphate Impurities by Anion-exchange Chromotography on a Mono Q Column, Analyt. Biochem., 306, 92-99.

Zhu, T., and Boom, G. J. (1998) A two-directional approach for the solid-phase synthesis of trisaccharide libraries. *Angew. Chem. Int. Ed.,* 37, 1898-1900.

What is claimed is:

1. A system for identifying one or more proteins that interact with a specific oligonucleotide on a bead comprising:
   - an oligonucleotide-bead library for binding one or more proteins, wherein each bead of the oligonucleotide-bead library comprises more than one copy of a unique oligonucleotide having a unique sequence, wherein the unique oligonucleotides are attached to the beads by a hexaethyleneglycol linker, and wherein the oligonucleotides attached to the bead are not released during phosphoroamidite deprotection; and
   - a bead separator wherein the one or more beads of the bead library to which protein has bound are separated by the bead separator.

2. The system of claim 1, further comprising a nucleic acid sequencer to determine the sequence of the oligonucleotide.

3. The system of claim 1, wherein the sequence of the oligonucleotides on the one or more beads that bind to known proteins is determined.

4. The system of claim 1, wherein the one or more proteins bound to the oligonucleotide are extracted, separated and identified by liquid chromatography, mass spectrometry, or liquid chromatography and time of flight (TOF) mass spectrometry (MS) MALDI-TOF.

5. The system of claim 1, further comprising a mass spectrometer to identify the proteins that have bound to the one or more oligonucleotide-beads.

6. The system of claim 1, wherein the oligonucleotide is defined further as comprising an at least partially thio-modified oligonucleotide.

7. The system of claim 1, wherein the one or more proteins is further defined as being a protein extracted from a cell.

8. The system of claim 1, wherein the one or more proteins is further defined as being a protein extracted from a virally infected cell.

9. The system of claim 1, wherein the one or more proteins is further defined as being a protein extracted from a diseased cell.

10. The system of claim 1, wherein the bead library is substantially protein-free.

11. The system of claim 1, wherein the bead library comprises an [S]-oligonucleotide or an [S$_2$]-oligonucleotide combinatorial bead library.

12. The system of claim 1, wherein the oligonucleotides of the bead library are single stranded.

13. The system of claim 1, wherein the oligonucleotides of the bead library comprises RNA.

14. The system of claim 1, wherein the bead library comprises sequence motifs for high affinity with cellular proteins selected from the group consisting essentially of proteins that are members of the AP-1, RBP-Jκ, NF-κB, NF IL-6, CREB and GRE protein families, and combinations thereof.

* * * * *

SEQUENCE LISTING

```
<160> NUMBER OF SEQ ID NOS: 58

<210> SEQ ID NO 1
<211> LENGTH: 34
<212> TYPE: DNA
<213> ORGANISM: Artificial Sequence
<220> FEATURE:
<223> OTHER INFORMATION: Synthetic oligonucleotide.

<400> SEQUENCE: 1
ccaggagats tsccacggst ccstcstaag gstg                                  34

<210> SEQ ID NO 2
<211> LENGTH: 34
<212> TYPE: DNA
<213> ORGANISM: Artificial Sequence
<220> FEATURE:
<223> OTHER INFORMATION: Synthetic oligonucleotide.

<400> SEQUENCE: 2
ccagtsgact scagtsgggs tcacstgags tcac                                  34

<210> SEQ ID NO 3
<211> LENGTH: 34
<212> TYPE: DNA
<213> ORGANISM: Artificial Sequence
<220> FEATURE:
<223> OTHER INFORMATION: Synthetic oligonucleotide.

<400> SEQUENCE: 3
tstsgcgcgc aacatsgaac gcgcgststg stac                                  34

<210> SEQ ID NO 4
<211> LENGTH: 28
<212> TYPE: DNA
<213> ORGANISM: Artificial Sequence
<220> FEATURE:
<223> OTHER INFORMATION: Synthetic oligonucleotide.

<400> SEQUENCE: 4
```

```
ccagtgactc agtgggtcac tgagtcac                                              28

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide.

<400> SEQUENCE: 5
ttgcgcgcaa catgaacgcg cgttgtac                                              28

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 6
tgtgcaggga ctgatgacgg t                                                     21

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 7
ctgtgcatcg aagtttgcat tt                                                    22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 8
atgcacatct caggatgacg gt                                                    22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 9
agttgcaggt caggacccat tt                                                    22

<210> SEQ ID NO 10
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 10
ctgttcgggc gcca                                                             14

<210> SEQ ID NO 11
<211> LENGTH: 42
<212> TYPE: DNA
<213> ORGANISM: Artificial Sequence
```

<220> FEATURE:
<223> OTHER INFORMATION: Synthetic oligonucleotide.

<400> SEQUENCE: 11
ccaggagatt ccacccagga gattccaccc aggagattcc ac                              42

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 12
ctgtgttctt gtgccgtgtc cc                                                    22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 13
ctgtgttctt gtgtcgtgtc cc                                                    22

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 14
ctgtgttctt gtgtcgtgcc cc                                                    22

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 15
ccgtgttctt gtgccgtgtc cc                                                    22

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 16
ccgtgttctt gtgtcgtgtc cc                                                    22

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 17
cggggtgttg tcctgtgctc tcc                                                   23

-continued

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 18
cggggtgttc tcctgtgctc tcc                                              23

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 19
cggggtggtg tggcgaggcg gcc                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 20
cggggtggtg cggcgaggcg gcc                                              23

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 21
cggggtgtgc tgctgcgggc ggc                                              23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 22
cggggtgtgc tgctgcgggc ggc                                              23

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 23
ctgtgytctt gtgtygtgtc cc                                               22

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 24
rgaccgaaac gaagggccg ac                                         22

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide.

<400> SEQUENCE: 25
rcaggacggc acaaccgcac acgca                                     25

<210> SEQ ID NO 26
<211> LENGTH: 15
<212> TYPE: DNA
<213> ORGANISM: Artificial Sequence
<220> FEATURE:
<223> OTHER INFORMATION: Synthetic oligonucleotide.

<400> SEQUENCE: 26
ggatccggtg gtctg                                                15

<210> SEQ ID NO 27
<211> LENGTH: 15
<212> TYPE: DNA
<213> ORGANISM: Artificial Sequence
<220> FEATURE:
<223> OTHER INFORMATION: Synthetic oligonucleotide.

<400> SEQUENCE: 27
cctactcgcg aattc                                                15

<210> SEQ ID NO 28
<211> LENGTH: 14
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 28
atgngaattt ncca                                                 14

<210> SEQ ID NO 29
<211> LENGTH: 14
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 29
ggagngcnca ggac                                                   14

<210> SEQ ID NO 30
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 30
ggaggacttt ccac                                                   14

<210> SEQ ID NO 31
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 31
ggaggacatt gcac                                                   14

<210> SEQ ID NO 32
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 32
ggaggacctt ccac                                                   14

<210> SEQ ID NO 33
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 33
ggaggacctt gcac                                                   14

<210> SEQ ID NO 34
<211> LENGTH: 14
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (8)..(8)
<223> OTHER INFORMATION: n is a, c, g, or t

<400> SEQUENCE: 34
ggaggacntt tcac                                                   14

<210> SEQ ID NO 35
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 35
ggaggacctt tcac                                                   14

```
<210> SEQ ID NO 36
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 36
gggatggtca ggac                                                      14

<210> SEQ ID NO 37
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 37
gggcggatca ggac                                                      14

<210> SEQ ID NO 38
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 38
gggaagatca ggac                                                      14

<210> SEQ ID NO 39
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 39
ggggtgatca ggac                                                      14

<210> SEQ ID NO 40
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 40
ggagtgctca ggca                                                      14

<210> SEQ ID NO 41
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 41
ggagcggtgt ccac                                                      14

<210> SEQ ID NO 42
<211> LENGTH: 14
<212> TYPE: DNA
<213> ORGANISM: Artificial Sequence
<220> FEATURE:
<223> OTHER INFORMATION: Synthetic oligonucleotide.
```

```
<400> SEQUENCE: 42
gggagggatt acca                                                14

<210> SEQ ID NO 43
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 43
ggagcggttt gcca                                                14

<210> SEQ ID NO 44
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 44
ggagcgattt ccca                                                14

<210> SEQ ID NO 45
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 45
ggagaggttt tcca                                                14

<210> SEQ ID NO 46
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 46
atagggcaca ggac                                                14

<210> SEQ ID NO 47
<211> LENGTH: 14
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (5)..(5)
<223> OTHER INFORMATION: n is a, c, g, or t

<400> SEQUENCE: 47
atagngccca ggac                                                14

<210> SEQ ID NO 48
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 48
atagggcgca ggac                                                14
```

<210> SEQ ID NO 49
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 49
ggagggccca gcac                                                      14

<210> SEQ ID NO 50
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 50
ggagagcaca tcac                                                      14

<210> SEQ ID NO 51
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 51
ggagcgcgca ccac                                                      14

<210> SEQ ID NO 52
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 52
ggagcgcgca gcac                                                      14

<210> SEQ ID NO 53
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 53
ggagggctca gcac                                                      14

<210> SEQ ID NO 54
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 54
ggagagcaca acac                                                      14

<210> SEQ ID NO 55
<211> LENGTH: 14
<212> TYPE: DNA
<213> ORGANISM: Artificial Sequence
<220> FEATURE:

```
<223> OTHER INFORMATION: Synthetic oligonucleotide.

<400> SEQUENCE: 55
ggagcgcgca tcac                                                    14

<210> SEQ ID NO 56
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 56
ggagagcgca ccac                                                    14

<210> SEQ ID NO 57
<211> LENGTH: 30
<212> TYPE: DNA
<213> ORGANISM: Artificial Sequence
<220> FEATURE:
<223> OTHER INFORMATION: Synthetic oligonucleotide.

<400> SEQUENCE: 57
ccaggagatt ccacggatcc ggtggtctgt                                   30

<210> SEQ ID NO 58
<211> LENGTH: 15
<212> TYPE: DNA
<213> ORGANISM: Artificial Sequence
<220> FEATURE:
<223> OTHER INFORMATION: Synthetic oligonucleotide.

<400> SEQUENCE: 58
cctactcgcg aattc                                                   15
```